US012682200B2

(12) United States Patent
Cortese et al.

(10) Patent No.: US 12,682,200 B2
(45) Date of Patent: *Jul. 14, 2026

(54) WIRELESS, OPTICALLY-POWERED OPTOELECTRONIC SENSORS

(71) Applicant: Cornell University, Ithaca, NY (US)

(72) Inventors: Alejandro J. Cortese, Ithaca, NY (US);
Alyosha C. Molnar, Ithaca, NY (US);
Paul L. McEuen, Newfield, NY (US);
Sunwoo Lee, Ithaca, NY (US)

(73) Assignee: CORNELL UNIVERSITY, Ithaca, NY
(US)

( * ) Notice: Subject to any disclaimer, the term of this
patent is extended or adjusted under 35
U.S.C. 154(b) by 0 days.

This patent is subject to a terminal dis-
claimer.

(21) Appl. No.: 19/048,612

(22) Filed: Feb. 7, 2025

(65) Prior Publication Data

US 2025/0190738 A1 Jun. 12, 2025

Related U.S. Application Data

(63) Continuation of application No. 18/771,767, filed on
Jul. 12, 2024, now Pat. No. 12,271,775, which is a
(Continued)

(51) Int. Cl.
*G06K 19/07* (2006.01)
*A61B 5/00* (2006.01)
(Continued)

(52) U.S. Cl.
CPC ........ *G06K 19/0728* (2013.01); *A61B 5/0017*
(2013.01); *H04B 10/116* (2013.01);
(Continued)

(58) Field of Classification Search
CPC ... G06K 19/0728; H10F 71/00; H10F 77/955;
H10F 55/18; A61B 5/0017;
(Continued)

(56) References Cited

U.S. PATENT DOCUMENTS

| | | | | |
|---|---|---|---|---|
| 12,039,389 B2 * | 7/2024 | Cortese | .............. | G06K 19/0728 |
| 12,271,775 B2 * | 4/2025 | Cortese | ................ | A61B 5/6826 |

(Continued)

FOREIGN PATENT DOCUMENTS

| | | |
|---|---|---|
| JP | 2004-179646 | 6/2004 |
| JP | 2008-98442 | 4/2008 |

(Continued)

OTHER PUBLICATIONS

The International Search Report, dated Apr. 20, 2019 in connection
with PCT International Application No. PCT/US2019/17377, 22
pages.
Haydaroglu et al. "Optical Power Delivery and Data Transmission
in a Wireless and Batteryless Microsystem Using a Single Light
Emitting Diode", Journal of Microelectromechanical Systems, vol.
24, No. 1, Feb. 2015, 11 pages.
Kim et al. "Injectable, Cellular-Scale Optoelectronics with Appli-
cations for Wireless Optogenetics", Science 340, 211, Apr. 12, 2013
(Apr. 12, 2013), 49 pages.
(Continued)

*Primary Examiner* — Daniel A Hess
(74) *Attorney, Agent, or Firm* — MARSHALL,
GERSTEIN & BORUN LLP

(57) ABSTRACT

The technology disclosed in this patent document can be
used to construct devices with opto-electronic circuitry for
sensing and identification applications, to provide unteth-
ered devices for deployment in living objects and other
applications, and to provide fabrication techniques for mak-
ing such devices for commercial production. As illustrated
by specific examples disclosed herein, the disclosed tech-
nology can be implemented to provide fabrication methods,
substrates, and devices that enable wireless, inorganic cell-
scaled sensor and identification systems that are optically-
powered and optically-readout.

17 Claims, 44 Drawing Sheets

Related U.S. Application Data continuation of application No. 16/947,626, filed on Aug. 10, 2020, now Pat. No. 12,039,389, which is a continuation of application No. PCT/US2019/017377, filed on Feb. 8, 2019.

(60) Provisional application No. 62/628,190, filed on Feb. 8, 2018, provisional application No. 62/740,326, filed on Oct. 2, 2018.

(51) Int. Cl.

| | |
|---|---|
| *H04B 10/116* | (2013.01) |
| *H10F 55/00* | (2025.01) |
| *H10F 71/00* | (2025.01) |
| *H10F 77/00* | (2025.01) |
| *A01K 11/00* | (2006.01) |
| *A01K 29/00* | (2006.01) |

(52) U.S. Cl.

CPC .............. *H10F 55/18* (2025.01); *H10F 71/00* (2025.01); *H10F 77/955* (2025.01); *A01K 11/006* (2013.01); *A01K 29/005* (2013.01); *A61B 5/0031* (2013.01)

(58) Field of Classification Search

CPC .. A61B 5/0031; H04B 10/116; A01K 11/006; A01K 29/005

USPC ........................................................ 235/454

See application file for complete search history.

(56) References Cited

U.S. PATENT DOCUMENTS

| | | |
|---|---|---|
| 2008/0154101 A1 | 6/2008 | Jain et al. |
| 2010/0096447 A1 | 4/2010 | Kwon et al. |
| 2014/0228660 A1 | 8/2014 | Mujeeb-U-Rahman et al. |
| 2015/0112160 A1 | 4/2015 | Gazdzinski |
| 2015/0265182 A1 | 9/2015 | Jain et al. |
| 2017/0100056 A1 | 4/2017 | Zhu et al. |
| 2017/0109557 A1 | 4/2017 | Otis et al. |

FOREIGN PATENT DOCUMENTS

| | | |
|---|---|---|
| JP | 2017-505648 | 2/2017 |
| KR | 2015-0030552 | 3/2015 |

OTHER PUBLICATIONS

Lu et al. Wireless optoelectronic photometers for monitoring neuronal dynamics in the deep brain, Proceedings of the National Academy of Sciences 115.7 (2018), 10 pages.

Extended Search Report for EP App. No. 19751894.7, dated Jan. 14, 2022, 12 pages.

Article 94 Communication for co-pending EP App. No. 19751894.7, dated Mar. 22, 2024, 4 pages.

Japanese Office Action for co-pending application No. JP 2020-542832, filed Feb. 8, 2019, dated Feb. 2, 2023 10 pages with unofficial translation.

Japanese Penultimate Office Action for co-pending application No. JP 2020-542832, filed Feb. 8, 2019, office action dated Oct. 31, 2023 17 pages with unofficial translation.

Korean Office Action for co-pending application No. KR 10-2020-7025896, filed Feb. 8, 2019, office action dated Nov. 15, 2023 16 pages with unofficial translation.

Korean Office Action for co-pending application No. KR 10-2020-7025896, filed Feb. 8, 2019, office action dated Mar. 28, 2024, 10 pages with machine translation.

Song, et al. "Active Microelectronic Neurosensor Arrays for Implantable Brain Communication Interfaces," IEEE Transactions on Neural Systems and Rehabilitation Engineering, vol. 17, No. 4, Aug. 2009, 7 pages.

Png, et al. "Optical Infrastructure for Visible Light Communication for Public Housing and Commercial Buildings," 2013 IEEE Symposium On Computers And Communications (ISCC), IEEE, Jul. 7, 2013, 6 pages.

Partial Search Report for EP App. No. 19751894.7, dated Oct. 6, 2021, 16 pages.

Japanese Final Office Action and Decision of Dismissal for co-pending application No. JP 2020-542832, filed Feb. 8, 2019, office action dated Aug. 1, 2024, 10 pages with machine translation.

EPO, Summons to attend oral proceedings pursuant to Rule 115(1) EPC for European Application No. 19 751 894.7, mailed on Sep. 30, 2025, 10 pages.

JPO, Office Action for Japanese Application No. 2024-59041, mailed on May 8, 2025, 4 pages with unofficial English translation.

Japanese Penultimate Office Action for co-pending application No. JP 2024-059041, office action dated Aug. 26, 2025, 8 pages with Google translation.

* cited by examiner

| Material | Thickness(nm) | Dopant | Concentration |
|---|---|---|---|
| GaAs | 50 | P-type, C | 1E19 |
| Al₀.₁₅Ga₀.₈₅As | 200 | P-type, C | 1E18 |
| Al₀.₂₅Ga₀.₇₅As | 30 | Intrinsic | - |
| GaAs | 7 | Intrinsic | - |
| Al₀.₂₅Ga₀.₇₅As | 30 | Intrinsic | - |
| GaAs | 7 | Intrinsic | - |
| Al₀.₂₅Ga₀.₇₅As | 30 | Intrinsic | - |
| GaAs | 7 | Intrinsic | - |
| Al₀.₂₅Ga₀.₇₅As | 30 | Intrinsic | - |
| Al₀.₁₅Ga₀.₈₅As | 200 | N-type, Si | 1E17 |
| GaAs | 300 | N-type, Si | 1E18 |
| Al₀.₉₅Ga₀.₀₅As (release) | 300 | - | - |
| GaAs (Substrate) | | | |

FIG. 2A

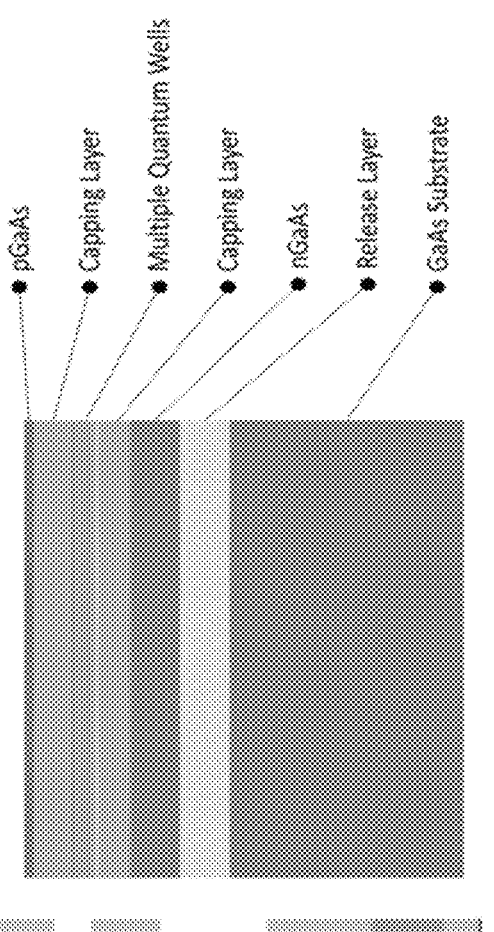

- pGaAs
- Capping Layer
- Multiple Quantum Wells
- Capping Layer
- nGaAs
- Release Layer
- GaAs Substrate

FIG. 2B

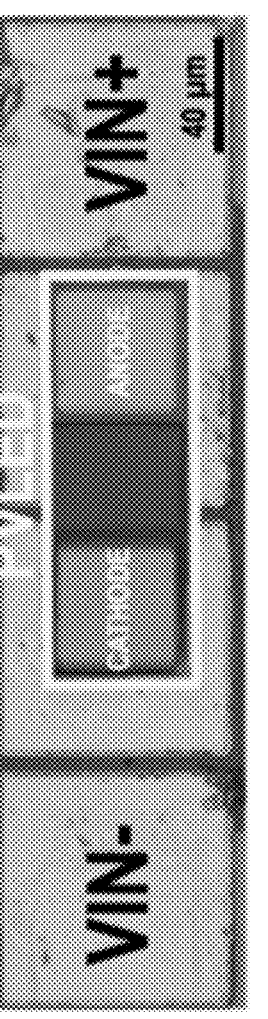
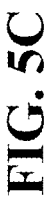
FIG. 5C
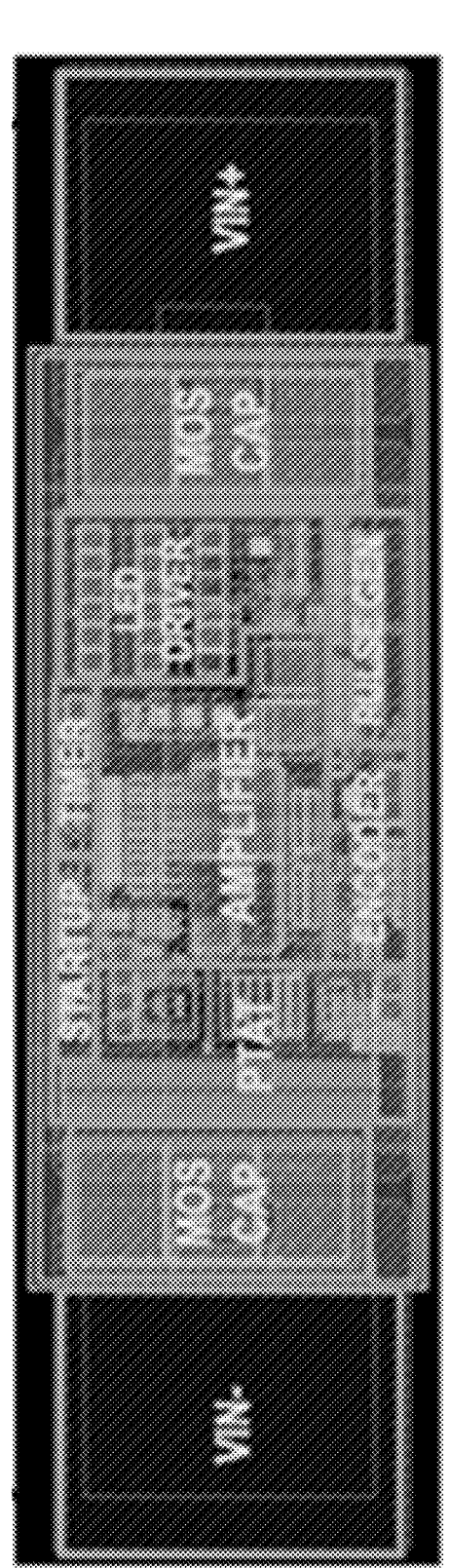
FIG. 5D

Si NMOS
MOSFET
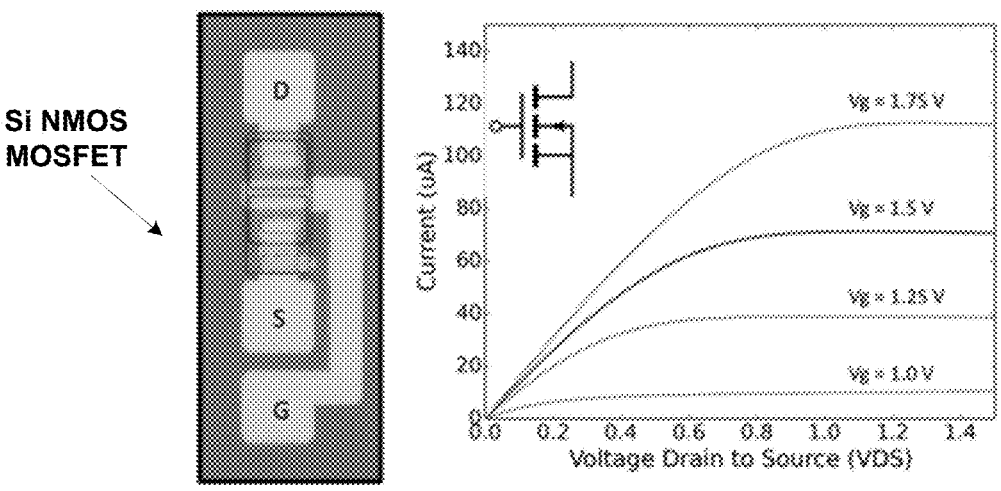
FIG. 7B
Si Photovoltaic
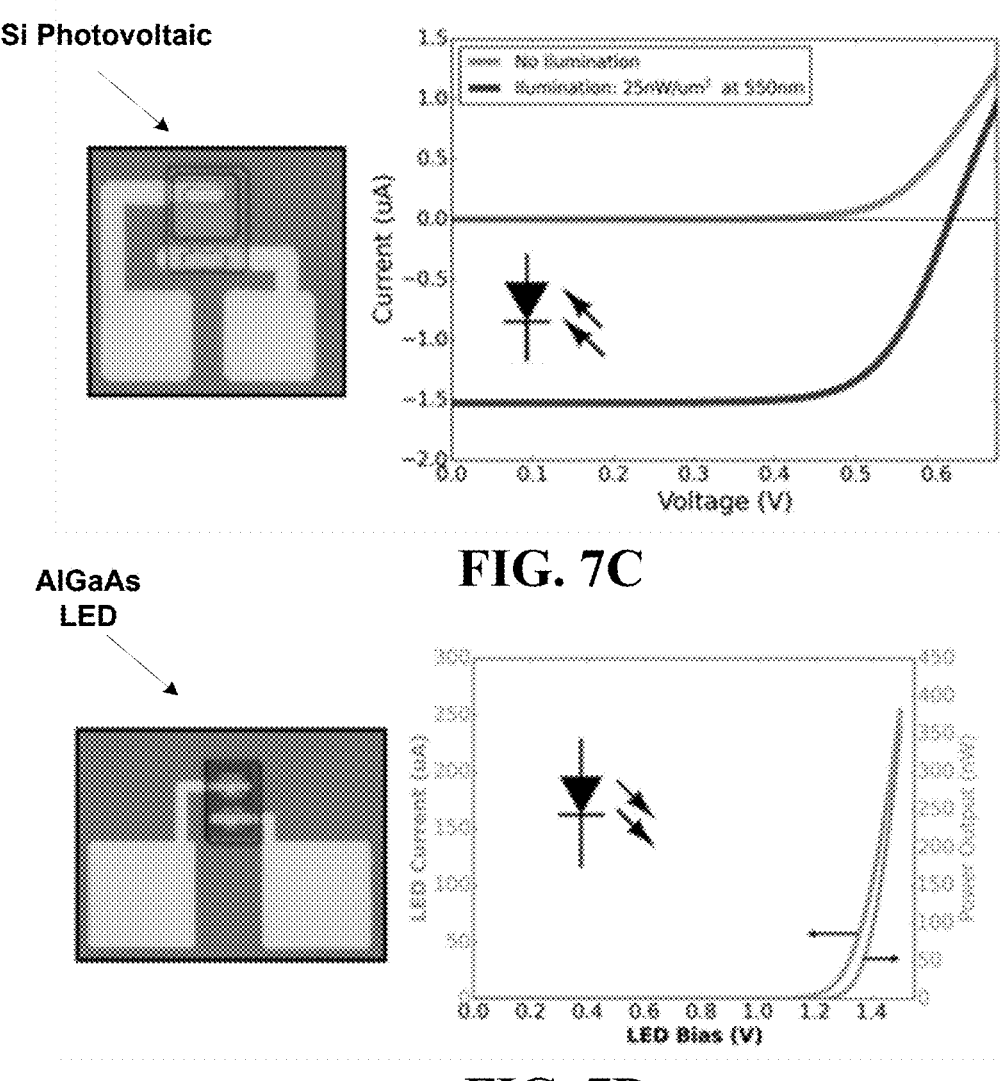
FIG. 7C
AlGaAs
LED
FIG. 7D

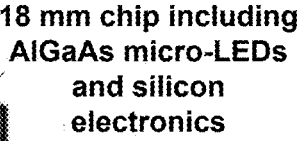
18 mm chip including AlGaAs micro-LEDs and silicon electronics
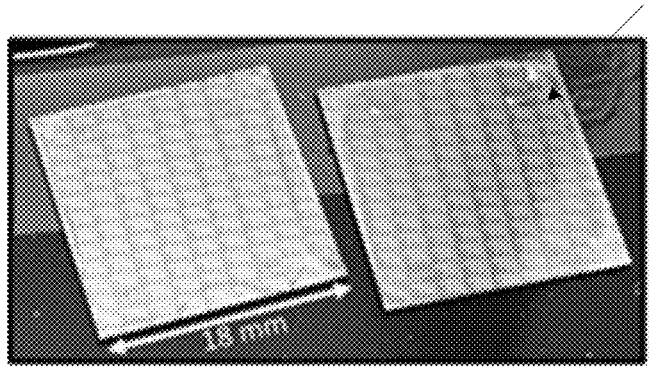
FIG. 10A
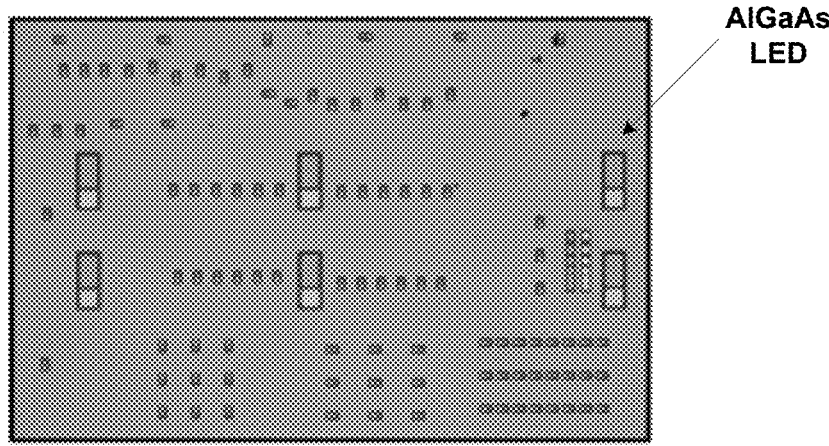
AlGaAs LED
FIG. 10B

Silicon
electronics

AlGaAs
LED

Si
Photovoltaic

Interconnect

GaAs LED

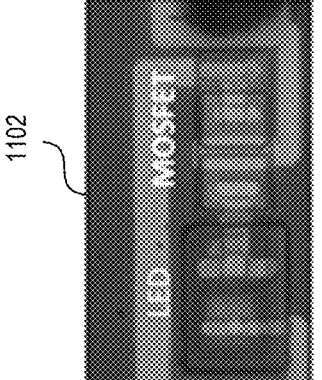
1102
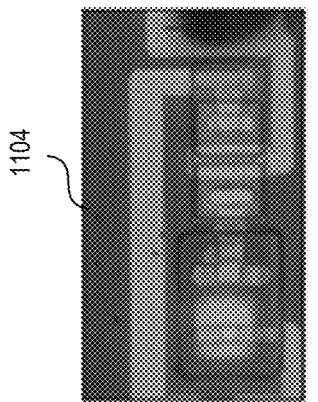
1104
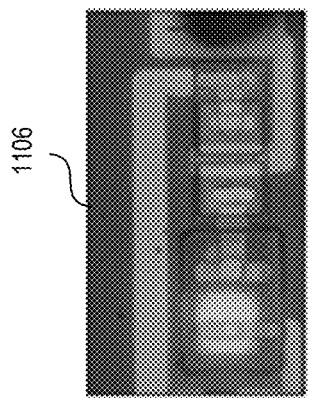
1106
Increasing Gate-Source Bias
FIG. 11D

Wireless
Sensors

Mouse's
brain

Brain
Tissue

Blood
Vessel

Wireless
Sensor

Human
Finger

Optically
powered
optoelectronic
device

Optically
powered
optoelectronic
device

| | Integrated Neural Interface [1] | Neural Dust [5] | This Work |
|---|---|---|---|
| Wireless Power Source | RF Coil | Ultrasonic | Optical |
| Gain (dB) | 60 | N/A | 24 |
| Bandwidth (KHz) | 5 | > 30 | 10 |
| Noise Floor ($\mu V_{RMS}$) | 5.1 | 180 | 21 |
| No. of Channels | 100 | 1 | 1 |
| Power per Channel | 135 $\mu$W | 0 | < 1 $\mu$W |
| Volume per Channel (mm³) | > 10 | 2.4 | < 0.01 |

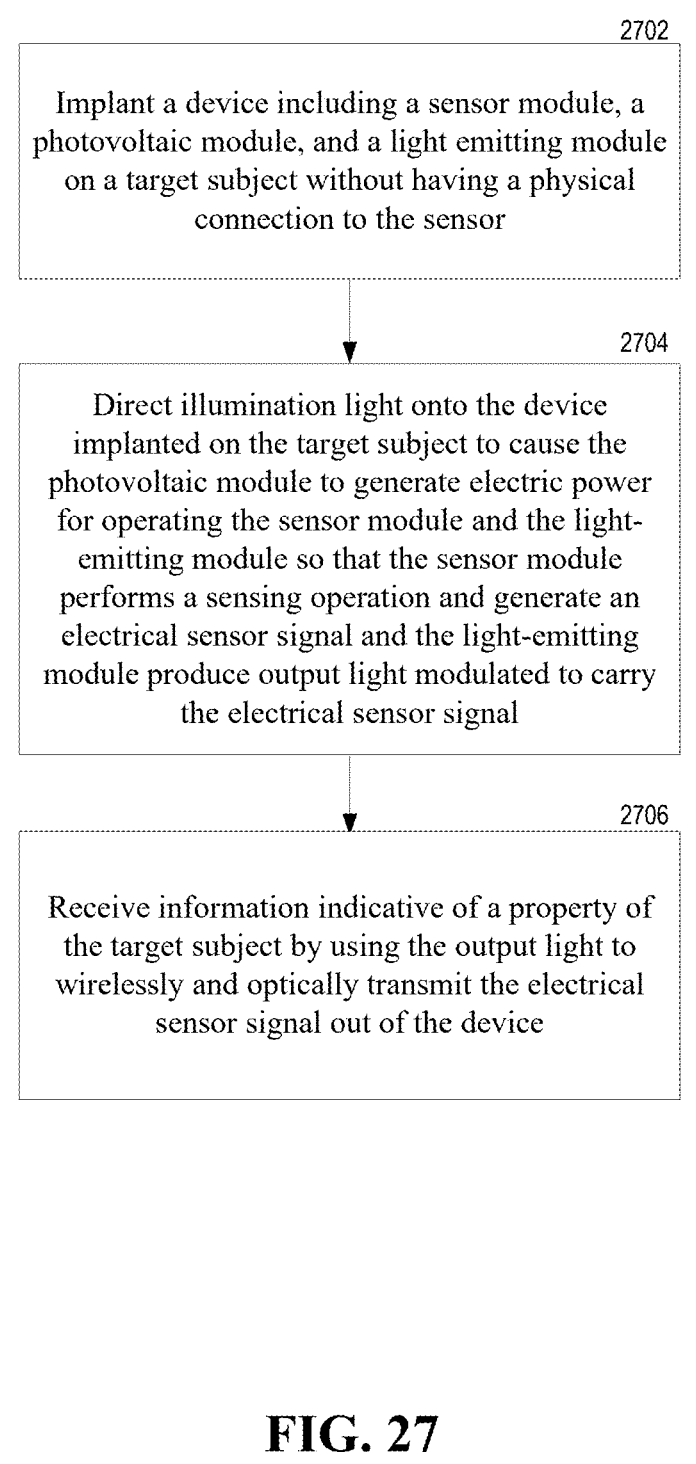

2702

Implant a device including a sensor module, a photovoltaic module, and a light emitting module on a target subject without having a physical connection to the sensor

2704

Direct illumination light onto the device implanted on the target subject to cause the photovoltaic module to generate electric power for operating the sensor module and the light-emitting module so that the sensor module performs a sensing operation and generate an electrical sensor signal and the light-emitting module produce output light modulated to carry the electrical sensor signal

2706

Receive information indicative of a property of the target subject by using the output light to wirelessly and optically transmit the electrical sensor signal out of the device

FIG. 27

WIRELESS, OPTICALLY-POWERED OPTOELECTRONIC SENSORS

PRIORITY CLAIMS AND RELATED PATENT APPLICATIONS

This patent document is a continuation application of, and claims benefits of priority to, U.S. patent application Ser. No. 18/771,767, filed Jul. 12, 2024 which is a continuation application of, and claims benefits of priority to, U.S. patent application Ser. No. 16/947,626, filed Aug. 10, 2020 and issued as U.S. Pat. No. 12,039,389B2 which is a continuation application of, and claims benefits of priority to, International Application No. PCT/US2019/017377, filed Feb. 8, 2019, entitled "WIRELESS, OPTICALLY POWERED OPTOELECTRONIC SENSORS AND DEVICES, which further claims the priorities and benefits of (1) U.S. Provisional Patent Application No. 62/628,190 entitled "WIRELESS, OPTICALLY-POWERED OPTOELECTRONIC SENSORS and filed on Feb. 8, 2018, and (2) U.S. Provisional Application No. 62/740,326 entitled "WIRELESS, OPTICALLY-POWERED OPTOELECTRONIC SENSORS" and filed on Oct. 2, 2018. The entirety of the disclosures of the above applications is incorporated by reference as part of the disclosure of this patent document.

TECHNICAL FIELD

This patent document relates to sensing technology and opto-electronic devices, systems and applications.

BACKGROUND

Sensors for sensing chemical or biological substances can be designed in various configurations. In some designs, sensors can include electrodes to be tethered to electronic devices or processors via conductive wiring. Such wiring may have undesired effects. For example, tethered implants for monitoring neural activities can cause residual motion between neurons and electrodes as the brain moves and accordingly may limit the ability to measure from peripheral nerves in moving animals, especially in smaller organisms such as zebra fish or fruit flies. Un-tethered wireless sensors are desirable for those and other applications.

SUMMARY

The technology disclosed in this patent document can be implemented to construct devices with opto-electronic circuitry for sensing and identification applications, to provide untethered devices for deployment in living objects and other applications, and to provide fabrication techniques for making such devices for commercial production. As illustrated by specific examples disclosed herein, the disclosed technology can be implemented to provide fabrication methods, substrates, and devices that enable wireless, inorganic cell-scaled systems that are optically powered and optically readout.

In one aspect, for example, the disclosed technology can be implemented to provide a device with opto-electronic circuitry to include a substrate; a photovoltaic module engaged to the substrate and structured to convert light into electricity; and a sensor module engaged to the substrate and coupled to receive power from the electricity generated by the photovoltaic module, the sensor module structured to include a sensing element that is responsive to a target substance to produce a response. The sensor module is further configured to generate, based on the response from the sensing element, an electrical sensor signal indicative of a property of the target substance. This device includes a light-emitting module engaged to the substrate and coupled to receive power from the electricity generated by the photovoltaic module and to receive the electrical sensor signal from the sensor module. The light-emitting module is structured to produce output light that is modulated to carry the electrical sensor signal to wirelessly and optically transmit the electrical sensor signal out of the device.

In another aspect, for example, the disclosed technology can be implemented to provide method for sensing a target subject. This method includes implanting a sensor on a target subject without having a physical connection to the sensor; directing illumination light onto the sensor implanted on the target subject to cause a photovoltaic module in the sensor generate electric power for operating the sensor so that the generated electric power powers (1) a sensor module which performs a sensing operation on the target subject to generate an electrical sensor signal indicative of a property of the target subject, and (2) a light-emitting module coupled to receive the electrical sensor signal from the sensor module and operable to produce output light that is modulated to carry the electrical sensor signal; and using the output light to wirelessly and optically transmit the electrical sensor signal out of the device.

In another aspect, for example, the disclosed technology can be implemented to provide a device with opto-electronic circuitry to include a substrate; a photovoltaic module engaged to the substrate and structured to convert light into electricity; and an identification module engaged to the substrate and coupled to receive power from the electricity generated by the photovoltaic module, the identification module configured to generate an electrical sensor signal indicative of an identity. This device includes a light-emitting module engaged to the substrate and coupled to receive power from the electricity generated by the photovoltaic module and to receive the electrical sensor signal from the identification module. The light-emitting module is structured to produce output light that is modulated to carry the electrical sensor signal to wirelessly and optically transmit the electrical identification signal out of the device.

In yet another aspect, for example, the disclosed technology can be implemented to provide a method for constructing a device with opto-electronic circuitry. This method includes forming a semiconductor release layer over a semiconductor substrate; fabricating photoelectronic semiconductor structures over the semiconductor release layer; forming a polymer layer over the fabricated photoelectronic semiconductor structures over the semiconductor release layer to embed the fabricated photoelectronic semiconductor structures in the formed polymer layer; performing an etching process to remove the semiconductor release layer to isolate the polymer layer and the fabricated photoelectronic semiconductor structures that are embedded in the polymer layer; and transferring the polymer layer and the fabricated photoelectronic semiconductor structures that are embedded in the polymer layer to a new substrate.

In yet another aspect, for example, the disclosed technology can be implemented to provide a device with opto-electronic circuitry that includes a substrate and a heterostructure module formed on the substrate to include patterned semiconductor layers to convert incident light at an incident optical wavelength into electricity and emits output light an output optical wavelength different from the incident optical wavelength. A sensor module is engaged to the substrate and coupled to receive power from the electricity generated by the heterostructure module, the sensor module structured to include a sensing element that is responsive to a target substance to produce a response and the sensor module is further configured to generate, based on the response from the sensing element, an electrical sensor signal indicative of a property of the target substance. This device further includes circuitry coupled to the heterostructure module and the sensor module operable to supply power from the electricity generated by the heterostructure module back to the heterostructure module to cause emission of the output light and to receive the electrical sensor signal from the sensor module and the heterostructure module is structured to produce that output light that is modulated to carry the electrical sensor signal to wirelessly and optically transmit the electrical sensor signal out of the device.

In yet another aspect, for example, the disclosed technology can be implemented to provide a device with opto-electronic circuitry that includes a substrate, a photovoltaic module engaged to the substrate and structured to convert light into electricity, a sensor module engaged to the substrate and coupled to receive power from the electricity generated by the photovoltaic module, the sensor module structured to include a sensing element that is responsive to a target substance to produce a response, wherein the sensor module is further configured to generate, based on the response from the sensing element, an electrical sensor signal indicative of a property of the target substance, and a light-emitting module photolithographically formed to the substrate to have a dimension less than 40 microns and coupled to receive power from the electricity generated by the photovoltaic module and to receive the electrical sensor signal from the sensor module, the light-emitting module structured to produce output light that is modulated to carry the electrical sensor signal to wirelessly and optically transmit the electrical sensor signal out of the device.

In yet another aspect, the disclosed technology can be implemented to provide an optical wireless sensor device that includes a photovoltaic module structured to convert electromagnetic radiation into electricity, a sensor module coupled to the photovoltaic to receive the electricity generated by the photovoltaic module and structured to include a sensing element and a communication element, the sensing element being responsive to a target substance to produce a response, the communication element being configured to generate, based on the response from the sensing element, an electrical sensor signal indicative of a property of the target substance, and a light-emitting module coupled to the photovoltaic module to receive the electricity and coupled to the sensor module to receive the electrical sensor signal and convert the electrical sensor signal to output electromagnetic radiation indicative of the property of the target substance.

In yet another aspect, the disclosed technology can be implemented to provide a device with opto-electronic circuitry, comprising: a substrate; a photovoltaic module engaged to the substrate and structured to convert light into electricity; an identification module engaged to the substrate and coupled to receive power from the electricity generated by the photovoltaic module, the identification module configured to generate an electrical identification signal indicative of an identity of the device; and a light-emitting module engaged to the substrate and coupled to receive power from the electricity generated by the photovoltaic module and to receive the electrical identification signal from the identification module, the light-emitting module structured to produce output light that is modulated to carry the electrical identification signal to wirelessly and optically transmit the electrical identification signal out of the device.

yet another aspect, the disclosed technology can be implemented to provide a device with opto-electronic circuitry, comprising: a substrate; a photo-electronic module engaged to the substrate and structured to convert light into electricity; and an identification module engaged to the substrate and coupled to receive power from the electricity generated by the photo-electronic module, the identification module configured to generate an electrical identification signal indicative of an identity of the device, wherein the photo-electronic module is configured to receive the electrical identification signal from the identification module and produce output light that is modulated to carry the electrical identification signal to wirelessly and optically transmit the electrical identification signal out of the device.

yet another aspect, the disclosed technology can be implemented to provide a device with opto-electronic circuitry, comprising: a substrate; a photovoltaic module engaged to the substrate and structured to convert input light into electricity, the photovoltaic module structured to include a sensing element that is responsive to a target substance to produce a response, wherein the photovoltaic module is further configured to generate, based on the response from the sensing element, an electrical sensor signal indicative of a property of the target substance; and a light-emitting module engaged to the substrate and coupled to receive power from the electricity generated by the photovoltaic module and to receive the electrical sensor signal from the photovoltaic module, the light-emitting module structured to produce output light that is modulated to carry the electrical sensor signal to wirelessly and optically transmit the electrical sensor signal out of the device.

yet another aspect, the disclosed technology can be implemented to provide a device with opto-electronic circuitry, comprising: a substrate; a photovoltaic module engaged to the substrate and structured to convert input light into electricity; and a light-electrical signal conversion module engaged to the substrate and structured to receive power from the electricity generated by the photovoltaic module, the light-electrical signal conversion module being responsive to a target substance to produce an electrical sensor signal indicative of a property of the target substance, the light-electrical signal conversion module being structured to produce output light that is modulated to carry the electrical sensor signal to wirelessly and optically transmit the electrical sensor signal out of the device.

The above and other aspects and implementations of the disclosed technology are described in more detail in the drawings, the description and the claims.

BRIEF DESCRIPTION OF THE DRAWINGS

FIGS. 2A-2B show examples of AlGaAs heterostructure light-emitting diode used for transfer.

FIGS. 5A-5F show an example lithographic integration of silicon CMOS circuitry and AlGaAs heterostructure for optically-powered and optically-readout neuron sensors.

FIGS. 7A-7D shows optical images and performance of micron-scale example configurations including silicon MOSFETs, silicon photovoltaics, and AlGaAs LEDs fabricated on the same substrate.

FIGS. 10A-10D show examples of large-scale integration of micron-scale silicon and III-V electronics and optoelectronics for releasable devices.

FIGS. 11A-11F show an example integrated circuit of GaAs LED and silicon MOSFET.

FIG. 27 shows an example method for sensing a target subject.

DETAILED DESCRIPTION

Figure 1A:
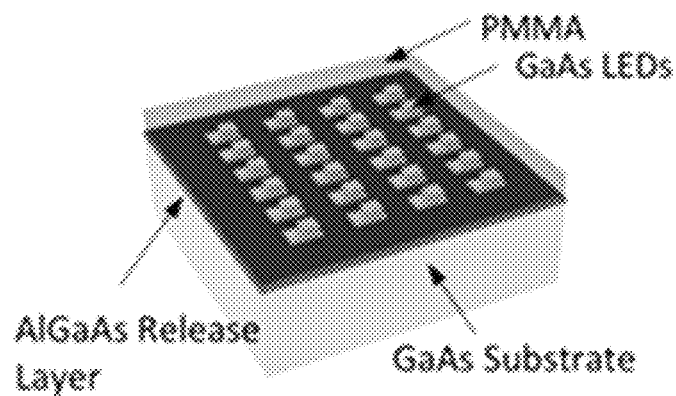
FIGS. 1A-1E show a method of polymer-assisted transfer of AlGaAs system heterostructures to other substrates.

Wireless devices for sensing, actuation, and identification are increasingly desired for smart packaging, medical sensors, and tracking. Some existing implementations of wireless systems are primarily powered by and communicate with RF coils or ultrasound. Size-scale requirements for such power sources fundamentally limit the size at which they can be produced. Furthermore, in some implementations, the techniques to construct such wireless sensors typically involve using dicing saws to dice materials, manually or serially stacking the material systems, and/or establishing electrical interconnects with wire-bonding or flip-chip bonding or using solder microbumps. These techniques can limit the size-scales and parallel production of devices and it is difficult to use such techniques to produce compact devices, such as those significantly smaller than 1 mm$^3$.

The disclosed technology in this patent document can be used to construct wireless sensors or/and wireless devices with opto-electronic circuitry that converts light into electricity for powering the devices and also generates output light that is modulated to carry information from the sensor operation so that such a sensor device is not linked to any physical connection outside the sensor device (e.g., a wire or cable) for versatile sensing and identification applications using wire-free devices. For example, in some embodiments of the disclosed technology, a wireless method for monitoring electrical and chemical signals at the individual cell level would allow for uses of wire-free devices with opto-electronic circuitry to provide wireless optical output of various sensor measurements ranging from mapping neural activity in the brain to detecting the release of neurotransmitters. Examples are disclosed for a transfer method, substrate, and devices enabling wireless, inorganic cell-scaled sensor systems that are optically powered, optically readout, and capable of monitoring electrical and chemical signals.

Recording neural activity in live animals in vivo poses several challenges. Electrical techniques typically require electrodes to be tethered to the outside world directly via a wire, or indirectly via an RF Coil, which is much larger than the electrodes themselves. Tethered implants result in residual motion between neurons and electrodes as the brain moves and limit our ability to measure from peripheral nerves in moving animals, especially in smaller organisms such as zebra fish or fruit flies. On the other hand, various implementations of optical techniques, which are becoming increasingly powerful, are nonetheless often limited to subsets of neurons in any given organism, impeded by scattering of the excitation light and emitted fluorescence, and limited to low temporal resolution. This patent document discloses examples of designs of the electronics for an untethered electrode unit, powered by, and communicating through a microscale optical interface, combining many benefits of optical techniques with high temporal-resolution recording of electrical signals.

Some embodiments of the disclosed technology can be used to transfer and adhere AlGaAs system heterostructures to other substrates with one or more of the following unique features. Firstly, the disclosed technology can be used for transferring AlGaAs material system heterostructures to a wider variety of substrates. In addition to substrates such as silicon, glass, III-Vs, metals, flexible materials (PET, PDMS), etc., the disclosed technology can be used to transfer high-curvature objections like micron-scale needles, optical-fibers, microlens, etc. to desired final substrates. Secondly, unlike various other transfer methods that require that mesa structures be of the same or similar shape and size for each transfer, the disclosed method of polymer-assisted transfer of AlGaAs system heterostructures to other substrates may transfer a plurality of heterostructures of arbitrary shapes in varying sizes (e.g., from nanometers to 1 millimeter) in the same transfer process. Thirdly, unlike some implementations of transfer printing, which is a widely-used method for the transfer of micro-LEDs and other optical heterostructures, there is no need to tune the speed of delamination of a transfer stamp for pick-up and transfer in implementing the transfer under the disclosed technology in this patent document. The tuning of these parameters for consistent results and high-yield can be difficult. In addition, it can also be very difficult to transfer optical heterostructures of thickness less than 1 micron or those of non-rectangular shapes, such as parabolically shaped micro LEDs. The disclosed example for the polymer-assisted transfer method of AlGaAs system heterostructures may enable the transfer of such optical heterostructures in thin structures, including structures as thin as 900 nm, for example. Furthermore, optical heterostructures are adhered to silicon and other substrates using conformal dielectrics. These dielectrics can be thinner than many adhesive materials, and silicon dioxide, silicon nitride, and other dielectrics can be deposited at a nanometer scale and precision using atomic layer deposition, for example. These dielectrics also are stable at high temperatures (e.g., hundreds of degrees Celsius). These unique features contrast those of thick epoxies which are not compatible with high temperature processing standard to many semiconductor processes.

Some embodiments of the disclosed technology can be implemented to provide a substrate and fabrication method that enable the integration of silicon electronics (MOSFETs, photovoltaics, resistors, capacitors, JFETs, BJTs, etc.) and aforementioned transferred AlGaAs heterostructures at the micron-scale for releasable, wireless cell-scaled devices. The substrate and fabrication method can be implemented with one or more of the following unique features. Firstly, a PN-junction or PNP-junction is made and activated in the device layer of a silicon on insulator substrate prior to transfer of optical heterostructures. This avoids incompatibilities in thermal budgets that typically make standard silicon electronic fabrication methods incompatible with the AlGaAs system. This also enables high-performance, nanometer- or micron-scaled silicon electronics to be patterned in alignment to AlGaAs heterostructures in the same fabrication process. Secondly, the substrate and fabrication method disclosed in this patent document allows for the AlGaAs heterostructures to be separately optimized from the silicon fabrication process. An integration process of devices using gallium-arsenide grown on silicon are not as efficient as AlGaAs systems separately optimized and grown, and the performance of the two components typically suffers. Moreover, the methods based on the disclosed technology can provide technical solutions to fabrication issues that are difficult to solve by using various known fabrication techniques or processes such as those for releasing fabricated structures or devices. Thirdly, it is possible to transfer III-V heterostructures onto silicon CMOS devices to make integrated devices with better performance, but the method of polymer-assisted transfer of AlGaAs system heterostructures is superior to existing methods because the polymer-assisted transfer of AlGaAs system heterostructures can be made in a manner that enables a releasable device at cell-scale. Moreover, the designs for various sensor and/or identification devices disclosed in this patent document may be formed using many different designs integrating silicon and AlGaAs systems with tens of thousands of integrated circuits (ICs) on every chip.

Some embodiments of the disclosed technology can be implemented to provide wireless, optically powered inorganic optoelectronics for cell-scaled devices that can receive information optically and optically communicate information out. The optically powered devices implemented based on some embodiments of the disclosed technology may be enabled by the aforementioned methods and substrates. The optically powered devices may be structured to include one or more unique features including the followings. For example, the optically powered devices implemented based on some embodiments of the disclosed technology can be wireless, inorganic cell-scaled devices with optical-power using micron-scale photovoltaics. These devices can also be structures to convert electrical signals into an optically readout signals using micro-LEDs (or other optical heterostructures). Furthermore, the optically powered, wireless, inorganic cell-scaled devices can be configured to allow untethered, wireless optical-communications using encoded light read and using micron-scale photovoltaics. In some implementations, the optically powered, wireless, inorganic systems based on the disclosed technology can be made at the cell-scale or other desirable scales suitable for specific applications. The cell-scale or miniaturized scales can be used to enable injection of the device while causing little to no tissue damage if intended for biological systems. The optically powered devices also allow for high-speed (greater than kHz) detection of signals optically using a wireless system that can be made at the cell-scale. This feature is in contrast to other imaging techniques, for example, calcium imaging of cells. By using the fabrication methods disclosed in this patent document, thousands to millions of devices can be implanted at arbitrary locations without fixed relative distances to one another. In addition, signal multiplexing in time of the communication out and optical carrier wavelength of the output signal allows for monitoring of potentially a large number of sensor and/or identification devices (e.g., more than a thousand of sensor devices) simultaneously, thus achieving parallel sensor measurements and processing.

Some methods based on the disclosed technology for millimeter-scaled, untethered sensors and identifications may implement a suitable power technology, including, for example, the RF-coil power, on-board batteries, or ultrasonic-powering using piezo-electronics. The disclosed technology can be used to integrate micron-scale photovoltaics with LEDs as a method of enabling an optically powered, optically readout sensor made at the cell-scale. This aspect of the disclosed technology enables several features such as: power to be supplied externally using light; information to be supplied to the sensor using light; and for the device to communicate out information via light. By using electromagnetic radiation, an immense amount of power can be concentrated into an extremely small, down to the nanoscale, volume, and communication can be achieved at the fastest speeds possible. In addition, the devices, their communication, and their powering can be electrically decoupled from the system if desirable.

Sensor and/or identification devices based on the disclosed technology can be used to enable optically powered, optically controlled, optically readout current sources, voltages source, voltage sensors, and current sensors to be integrated into the same releasable system. The disclosed technology enables cyclic-voltammetry (fast-scan cyclic voltammetry, ultramicroelectrode voltammetry, etc.) that can be performed in a cell-sized volume of fluid with the sensor system within the fluid. This enables uses such as neurotransmitter detection at the individual cell-scale. Additionally, by detecting chemical species in small volumes, a small-sample can provide enough material for a larger multitude of tests in cases. This may be of great use in cases where sample volume is limited. The disclosed technology also provides cell-scale voltage sensors that can be made to detect electrical signals from individual neurons, cardiac cells, etc. The disclosed technology can be further implemented to detect cell-scale ionic currents through cell-membranes, nano-constrictions, or microfluidic channels. The disclosed technology may also enable voltages and currents to be applied to solutions to stimulate cells or neurons using cell-scaled systems.

Examples of the Transfer Method in Fabrication

Materials used for efficient light-emitting structures are often not the same as those materials used for high-performance electronic devices. In an embodiment of the disclosed technology, silicon may be used to construct high-performance transistors (e.g., MOSFETs, BJTs, JFETs, etc.) that form the structures implemented based on some embodiments of the disclosed technology. The indirect band gap of silicon, however, may make it inefficient as a material for emitting light. In another embodiment of the disclosed technology, AlGaAs light-emitting diode heterostructure can be used for transfer. Although the AlGaAs system is not typically used to produce transistors in modern electronics, they may be used to produce high-efficiency light-emitting diodes (LEDs) and lasers. Embodiments could also include, more specifically, resonant cavity LEDs (RCLEDs) and vertical-cavity surface-emitting laser (VCSELs).

The disclosed heterostructures may be implemented by combining two material systems such as silicon and AlGaAs at the micron-scale to enable hybrid optoelectronics utilizing high-performance electronics and efficient light-emitting components. Many methods including transfer printing, wafer bonding, ball-bonding, and epitaxial liftoff exist to attempt to address this desired goal. Each method for transfer comes with its own advantages and disadvantages over the alternatives. Various implementations of these existing techniques have not been able to construct wireless sensors at the cellular-scale.

Figure 1B:
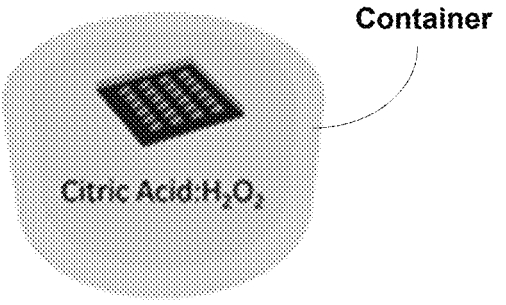

Various embodiments of the disclosed technology provide a novel method of transferring AlGaAs system heterostructures to other substrates as shown schematically in FIGS. 1A-1E. FIGS. 1A-1E show an example method of polymer-assisted transfer of AlGaAs system heterostructures to other substrates. In an implementation of the disclosed technology, a method of transferring AlGaAs systems (or any other sufficiently GaAs lattice-matched systems, such as AlGaAs, AlGaInP, GaP, and GaAsP) to various substrates starts with patterned or un-patterned heterostructures composed of various AlGaAs layers on a release layer of $Al_yGa_{1-y}As$, where y is between 0 and 1 and such that the release layer can be etch with sufficient selectivity against etching of the devices to be transferred and is sufficiently selective against the etching of the substrate. FIG. 1A illustrates a film of polymer (e.g., polymethyl methacrylate: PMMA) is spun and cured, covering the devices to be transferred. FIG. 1B illustrates the GaAs substrate is etched in a mixture of citric acid and hydrogen peroxide at a ratio that selectively etches the GaAs substrate more rapidly than the $Al_yGa_{1-y}As$ release layer.

Figure 1C:
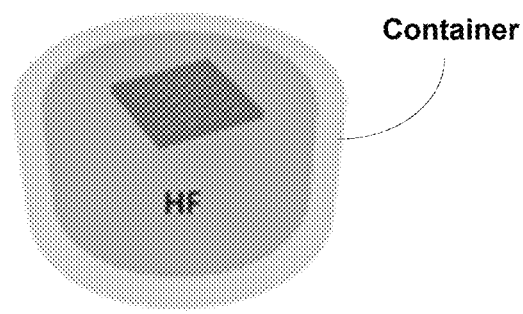
Figure 1D:
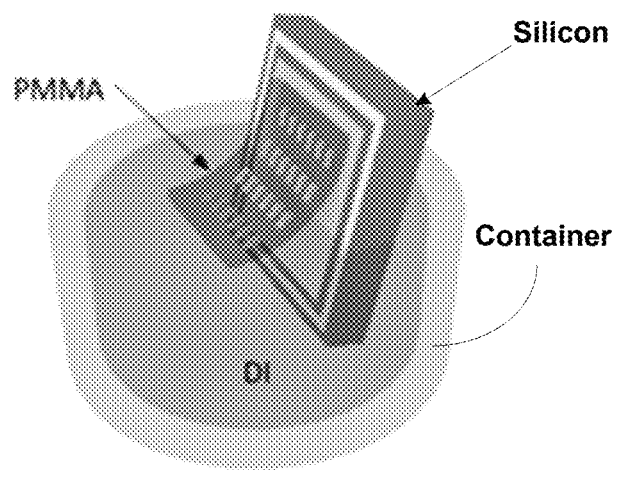
Figure 1E:
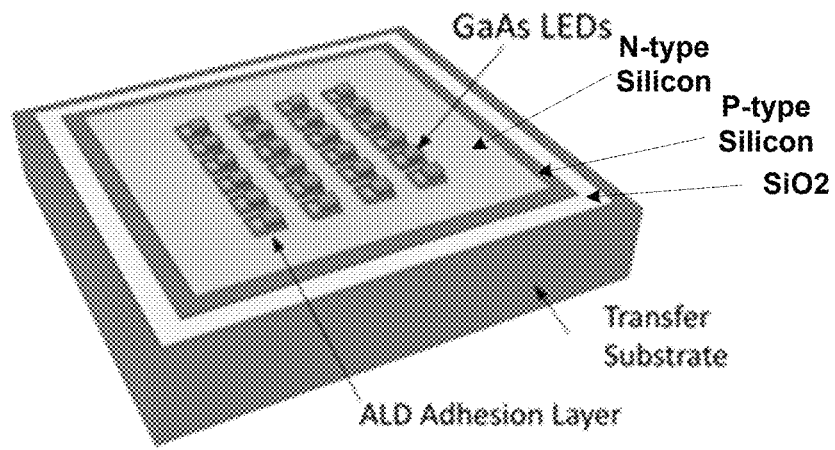

The release layer and polymer protect the devices to be transferred from being etched. FIG. 1C shows the release layer is then etched in a dilute mixture of hydrofluoric acid (HF) which is selective against etching the AlGaAs heterostructures. FIG. 1D illustrates, after transferring the polymer-encased devices through a DI bath to remove any contaminants, the polymer film can be transferred to a new substrate. If needed, as shown in FIG. 1E, the polymer can then be removed with a dry etch such as reactive ion etching using oxygen plasma. For adhesion to the substrate, conformal dielectrics such as SiO2 can be deposited. In another embodiment, the $Al_yGa_{1-y}As$ release layer can be selectivity etched (with, e.g., HF) without need to etch the GaAs substrate. This may have benefits for particular applications with the GaAs substrate is desired for reuse.

FIGS. 2A-2B show examples of AlGaAs heterostructure light-emitting diode used for transfer. Specifically, FIG. 2A shows a table detailing material, thickness, dopant, and concentration of AlGaAs system layers used to produce light-emitting diodes. Some embodiments of the disclosed technology can be used to transfer AlGaAs system heterostructures (light-emitting diodes, lasers, transistors, etc.) to arbitrary substrates (silicon, glass, PET, optical fibers, etc.). By way of example and not by limitation, the disclosed technology can be used to transfer AlGaAs micro-LEDs to a silicon substrate.

FIG. 2B shows cross-section of the layers of the AlGaAs light-emitting diode on the intermediate release layer and GaAs substrate implemented based on some embodiments of the disclosed technology. To begin, an AlGaAs heterostructure is grown by a metalorganic chemical vapor deposition (MOCVD). The series of layers can be broken into three fundamental portions, including substrate, release layer, and heterostructure. In an implementation, the substrate is a thick, few-hundred-micron, wafer of intrinsic GaAs, and the release layer is a thin, few-hundred nanometer, layer of $Al_{0.9}Ga_{0.1}As$. In an implementation, the heterostructure is a series of layers grown on top of the release layer composed of contact layers, cladding layers, and an emission region where electron-hole pairs combine to emit light. In this case, the optical heterostructure is an LED with multiple quantum wells for increased efficiency of electron-hole recombination.

After growth of the optical heterostructure on the release layer, the AlGaAs heterostructures are then pattern into micron-scaled LEDs (micro-LEDs) of various sizes and shapes with metal contacts for electrical interconnects to the anode and cathode. A thin layer of polymer is spun onto the micro-LEDs and cured using standard photolithography techniques. In an embodiment of the disclosed technology, a 1.5 micron thick layer of poly (methyl methacrylate) (PMMA) is spun onto the topside of the substrate, covering the micro-LEDs. At this stage of the fabrication, there is an array of micro-LEDs patterned on top of the $Al_{0.9}Ga_{0.1}As$ release layer, coated with a thin layer of polymer as shown in FIG. 1A. The thin polymer layer serves to protect the micro-LEDs during the etch steps to follow and provide a frame fixing the relative location of the micro-LEDs.

In some embodiments of the disclosed technology, the next step utilizes the varying etch rates of different compositions of $Al_xGa_{1-x}As$ with x between 0 and 1. Depending on the composition of the $Al_xGa_{1-x}As$, the etch rate in different chemical solutions can vary by orders of magnitude. For example, $Al_{0.9}Ga_{0.1}As$ etches much slower in 4:1 citric acid:hydrogen peroxide than GaAs, whereas in hydrofluoric acid $Al_{0.9}Ga_{0.1}As$ etches much more rapidly than GaAs. A PMMA covered substrate is placed in a mixture of 4:1 citric acid:hydrogen peroxide for an extended period (e.g., about 20 hours for 500 micron thick substrates). The etch is so selective for GaAs and against $Al_{0.9}Ga_{0.1}As$ that in the time needed to etch the entire substrate, most of the $Al_{0.9}Ga_{0.1}As$ layer remains. This step is shown schematically in FIG. 1B. Both the $Al_{0.9}Ga_{0.1}As$ release layer and the PMMA serve to protect the AlGaAs optical heterostructure during this etch.

As shown in FIG. 1C, following the etch of the GaAs substrate, the remaining PMMA/heterostructure/release layer system is transferred to a dilute hydrofluoric acid (HF):deionized water (DI) mixture (50:1 HF:DI). This selectively etches the $Al_{0.9}Ga_{0.1}As$ release layer at a much higher rate than the micro-LEDs allowing for the release layer to be removed completely before the micro-LEDs have been etch any appreciable amount.

The remaining PMMA film containing the micro-LEDs is then passed through a cleaning process using, e.g., deionized (DI) water to remove contaminants before being transferred to a silicon substrate as shown in FIG. 1D. In this case, the transfer substrate is the PN-junction-containing silicon on insulator substrate described in the proceeding text. The sample is then dried in air on at a slightly elevated temperature on a hotplate.

Figure 3:
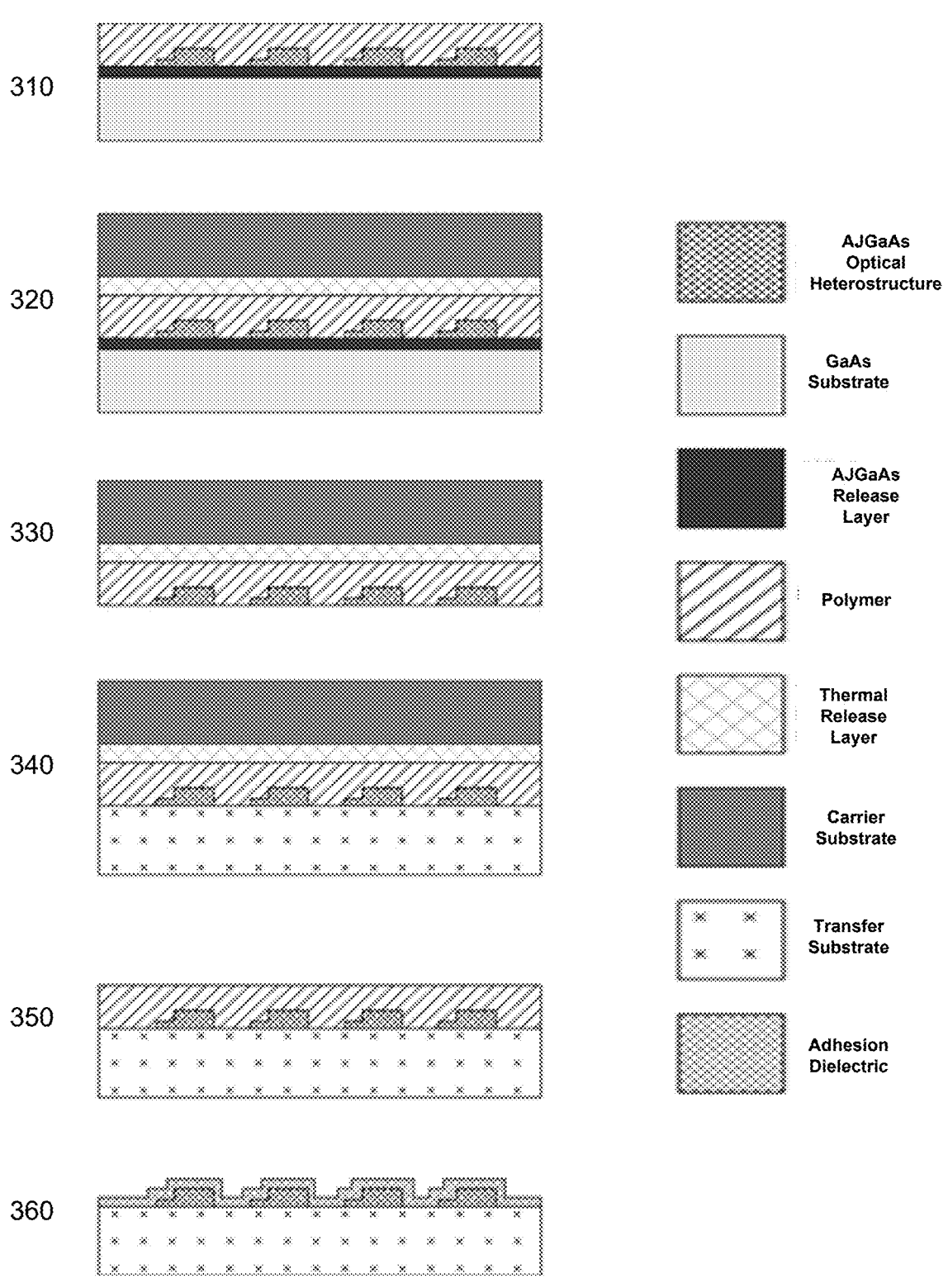
FIG. 3 illustrates an example planar alignment method of polymer-assisted transfer of AlGaAs system heterostructures to other substrates.

FIG. 3 illustrates an example alignment method of polymer-assisted transfer of AlGaAs system heterostructures to other substrates. If alignment of the AlGaAs heterostructures to the transfer substrate is needed, the transfer method can be adapted to aligned transfer. In one embodiment, a polymer, e.g. PMMA, is spun onto the AlGaAs optical heterostructures and cured (310). The AlGaAs optical heterostructures are on an AlGaAs release layer grown on a GaAs substrate as discussed above. A thermal release layer is spun onto the PMMA and used to bond the GaAs substrate to a carrier substrate (320). The carrier substrate can be any rigid structure partially transparent to visible or IR light. The thermal release layer is chosen such that the material can be removed at temperatures that do not remove or melt the PMMA. Examples of such materials include polypropylene carbonate (PPC) which can be removed at temperatures well below PMMA's melting point of 160 degrees Celsius. In another embodiment, this thermal releaser layer can be modified to be replaced by a thermal or ultra-violet (UV) release tape often using for semiconductor wafer dicing processes. Such tapes also reduce their adhesion force after being exposed to heat or UV light. The bonded substrates are placed in the wet etches described above to remove the GaAs substrate and AlGaAs release layer (330). Using the rigid carrier substrate, the AlGaAs optical heterostructures in PMMA can be aligned and bonded to the desired transfer substrate (340). By heating the system to a high enough temperature following alignment, the thermal release layer is removed allowing for the removal of the carrier substrate without removing the PMMA or AlGaAs optical heterostructures (350).

At this point in the process, the polymer can be removed completely or patterned by standard dry or wet etching techniques (360). For example, reactive-ion etching using an oxygen plasma can serve to remove PMMA without damaging the micro-LEDs. Using a dry etch technique allows for the micro-LEDs to remain with their relative locations, adhered to the substrate by van der Waals interactions.

If further adhesion is needed, a conformal layer of insulation material can be deposited adhering the micro-LEDs to the substrate (360), as also shown schematically in FIG. 1E. In one embodiment, atomic-layer deposition (ALD) can be performed using dielectrics such as silicon dioxide to adhere the micro-LEDs to the substrate. In another embodiment, plasma enhanced chemical vapor deposition (PECVD) can be performed to produce dielectrics such as silicon dioxide and silicon nitride.

If even further adhesion is desired, a thin layer of SU8 (can be deposited below 10 micron thickness), can be deposited and patterned prior to transfer. Either as deposited or under small amounts of heat, the SU8 layer can serve as a bonding layer between the light-emitting element and the substrate.

In another embodiment, if further adhesion is desired, low melting-temperature metals such as Rose's metal, or metals with strong bonding properties to AlGaAs such as palladium can be used to promote adhesion.

Figure 4:
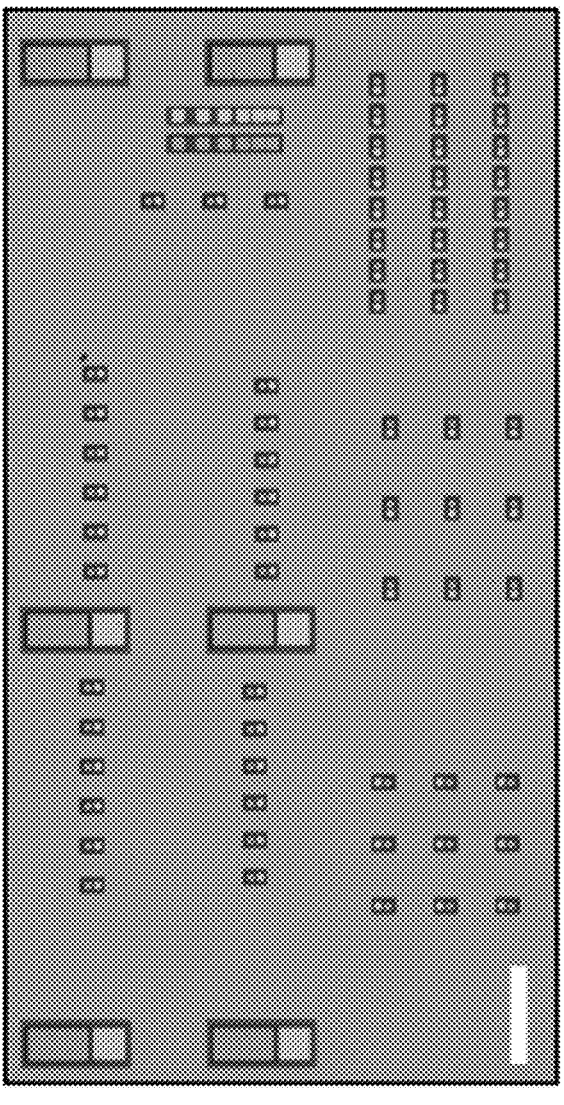
FIG. 4 shows an example of AlGaAs light-emitting diodes transferred to silicon substrate and adhered to the surface using a thin, conformal oxide.

FIG. 4 shows an example of AlGaAs light-emitting diodes transferred to silicon substrate and adhered to the surface using a thin, conformal oxide. LEDs of various sizes and shapes were transferred during the same transfer. Scale-bar, shown bottom-left, is 200 microns. Micro-LEDs shown are 900 nm in thickness and a variety of shapes and sizes. The method described above can be used to transfer micro-LEDs to various substrates including silicon, glass, metal, plastics, polymers, and micron-scale needles. Micro-LEDs of various sizes can be transferred to a silicon substrate and adhered using ALD silicon dioxide.

Figure 5A:
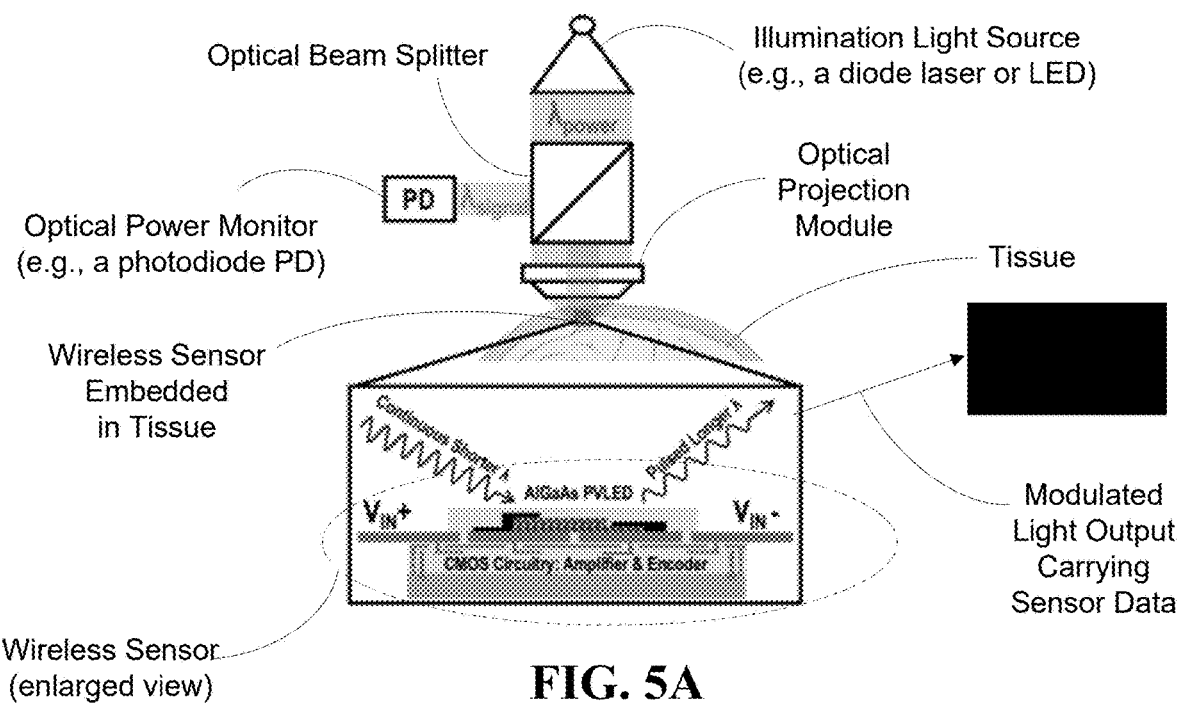

FIGS. 5A-5F show an example integration of silicon CMOS circuitry and AlGaAs heterostructure for optically-powered and optically-readout neuron sensors. Specifically, FIG. 5A illustrates schematic of a possible application enabled by the methods discussed above. The sensor device in FIG. 5A is shown as being embedded in an organ or tissue without wire attached and, as illustrated in the enlarged view, includes a photovoltaic module for receiving illumination light for converting the received illumination light into electricity to power the CMOS senor circuitry with one or more amplifiers and a signal encoder, and an optical transmitter for generating the optical output that is modulated to carry sensor data. An optical illumination light source is placed outside the tissue to illuminate the area of the tissue where the sensor device is located. In this specific example, an optical beam splitter is provided in the optical path between the tissue and the illumination light source to split the illumination light into a monitor beam to an optical monitor such as a photodiode (PD) and an illumination beam to the tissue. The optical monitor is used to adjust the intensity of the illumination light based on the monitor beam, thereby adjusting the intensity of the light illuminated on the photovoltaic module in the sensor device. The illumination beam output from the optical beam splitter is directed to the tissue using an optical projection module located between the optical beam splitter and the tissue. The photovoltaic module in the sensor device converts received illumination light into electricity that is used to energize various components in the sensor device, including, for example, a sensor that interacts with the tissue to obtain desired measurements in form of a sensor signal, a signal encoder that is used in encoding the sensor signal into a proper form for being modulated onto the output light generated by the optical transmitter. The sensor can optically send out the output light, which is modulated to carry the sensor signal, from the tissue so that an optical detection module outside the tissue can detect the sensor signal. In an implementation, the illumination light may include a continuous wave with a wavelength that is shorter than that of the output light. Some embodiments of the disclosed technology can be implemented to provide a cell-scale sensor that is capable of monitoring electrical signals from neurons by being injected into the tissue of the brain, optically powered via one wavelength and optically-readout using another wavelength. The particular GaAs heterostructure implemented based on some embodiments of the disclosed technology is capable of being a dual-purpose photovoltaic and LED (PVLED). Hence, once integrated, the photovoltaic provides power, the silicon circuitry measures, amplifies, and encodes the signal, and finally, the signal is optically communicated out using the LED functionality of the PVLED.

Figure 5B:
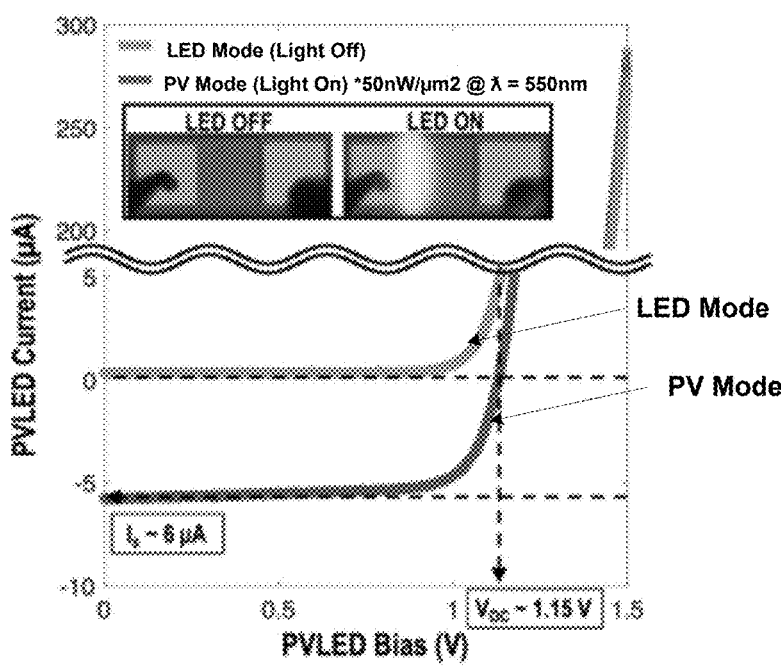

FIG. 5B shows performance of the dual-purpose PVLED, with I-V curves of a custom, dual-functioning AlGaAs photovoltaic/light emitting diode (PVLED) unit in its PV and LED modes. When mounted on top of a CMOS die, about 98% of the time, the PVLED acts as a power source, transducing incoming light into electrical power, providing at least 1 µA at ~0.9V. During the remaining 2% of the time, the PVLED acts as an optical transmitter, emitting optical pulses to transmit the measured data to an external receiver at a longer wavelength. This allows the system to be more compact than the previously reported RF and ultrasonic approaches.

Figure 5E:
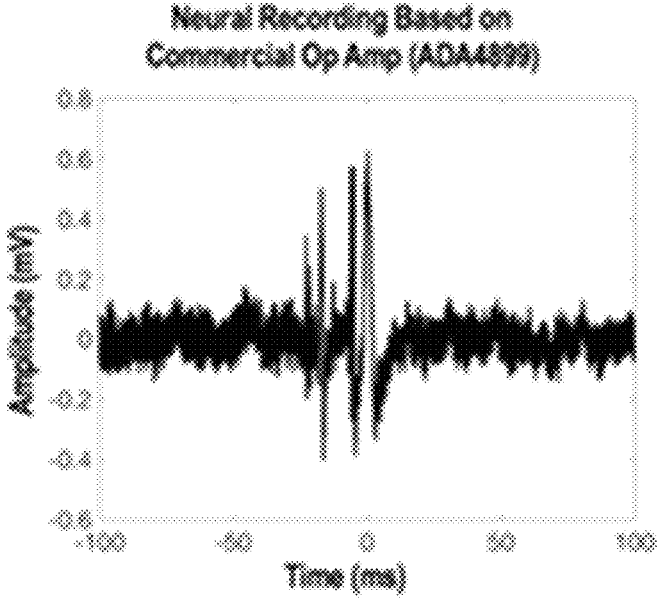
Figure 5F:
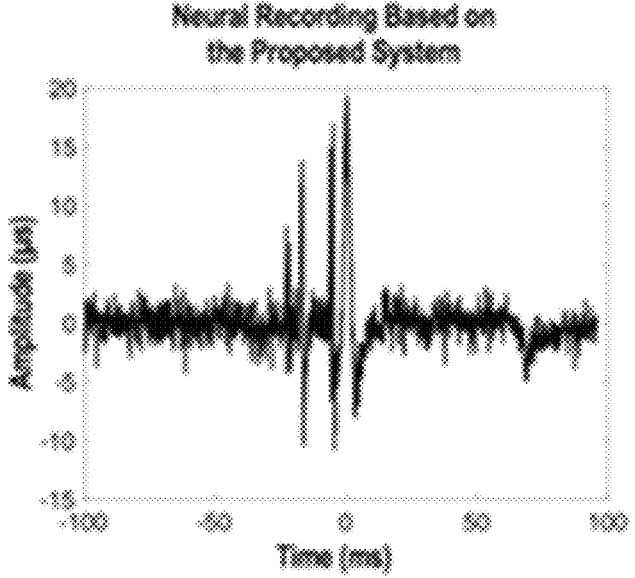

FIG. 5C shows an optical image of an integrated device with the AlGaAs PVLED transferred on top of electrical interconnects of a silicon CMOS circuit, depicting the integration of the PVLED on 180 nm CMOS where the underlying CMOS circuitry incorporates recording electrodes, amplification, pulse-position encoding, and a PVLED interface to arbitrate power and communications. The dual-purpose PVLED implemented based on some embodiments of the disclosed technology includes an AlGaAs photovoltaic/light emitting diode, an anode and a cathode of the AlGaAs photovoltaic/light emitting diode, and plus and minus inputs of CMOS circuitry formed on the CMOS die. In some embodiments of the disclosed technology, metal interconnects are patterned to electrically connect the anode and cathode of the AlGaAs photovoltaic/light emitting diode to the corresponding connections of the CMOS circuitry. Notably, the metal interconnects can be photolithographically formed such that the metal interconnects can have a smallest dimension under 10 microns and distances between electrodes are less than 40 microns. The dual-purpose PVLED implemented based on some embodiments of the disclosed technology can be formed by transferring AlGaAs optical heterostructure to CMOS circuitry using the disclosed methods. Since neural tissue is primarily scattering (as opposed to absorbing), such a system can, in principle, function at depths greatly exceeding that of imaging, but without the tethers required by most electrodes. The device is then connected electrically using standard photolithography. FIG. 5D shows layout of the CMOS circuitry underneath the top metal contacts including components such as inputs VIN− and VIN+, an amplifier, circuitry generating a proportional to absolute temperature current PTAT, circuitry for start-up STARTUP, a pulse generator PULSE GEN, MOS capacitors MOS CAP, an LED driver LED DRIVER, and encoding circuitry ENCODER. FIGS. 5E and 5F show comparison performance of a commercial amplifier to the silicon-PVLED system wired together.

As another illustration of the scope of use for this transfer method, this patent document provides an example where a dual-purpose photovoltaic/light-emitting diode (PVLED) is aligned, transferred, and integrated into a complex silicon complementary metal-oxide-semiconductor (CMOS) circuit shown in FIGS. 5C and 5D. The integrated device, enabled by this transfer method, is the first example of a wireless, optically powered and optically-readout inorganic cell-scaled sensor capable of monitoring neural activities.

The transfer of AlGaAs heterostructures transferred to both unpattern silicon and full CMOS silicon substrates is discussed in this patent document by way of example and not by limitation, and thus the method of transfer allows for many different embodiments. Using the same transfer method, both the type of heterostructure and the substrate can be varied. The possibilities for heterostructures that are capable of transferring using this method include, but are not limited to, light-emitting diodes, lasers, photovoltaics, and transistors. Some examples of transferrable heterostructures include: near-infrared GaAs lasers; red AlInP light-emitting diodes; AlGaAs photovoltaics; infrared InP lasers; and AlGaAs/GaAs high-electron-mobility transistors (HEMTs).

The substrate to which AlGaAs heterostructures can be transferred can also be varied. The possibilities for substrates to which the AlGaAs heterostructures can be transferred to using this method include, but are not limited to: semiconductors (silicon, AlGaAs, silicon carbide, sapphire, etc.); metals (gold, platinum, aluminum, etc.); dielectrics (silicon dioxide, aluminum oxide, silicon nitride, etc.); flexible substrates (PMMA, Polydimethylsiloxane, Polyethylene terephthalate, etc.); and high-curvature objects (microneedles, optical fibers, microlens, etc.)

Although the above disclosed examples of fabrication methods are for the AlGaAs material system, the methods disclosed can be adapted to device fabrication with other III-V semiconductor material systems such as GaN and InGaN. The above methods are implemented by using a material that can be used as the release layer which (1) is sufficiently lattice matched to the material system to be grown on it and (2) is selectively etchable with respect to the optical heterostructures layer in contact with it. In the example disclosed above, the $Al_{0.9}Ga_{0.1}As$ served as the latticed matched release layer and was etched selectively with hydrofluoric acid with respect to the n-type GaAs in contact with the $Al_{0.9}Ga_{0.1}As$. In another embodiment, GaN or InGaN optical heterostructures could be grown on (111) silicon release layer which can be selectively etched using potassium hydroxide. In another embodiment, GaN or InGaN optical heterostructures could be grown on heavily doped GaN layer with an electric bias applied to it allowing for selective etching in oxalic acid or other electrolyte solutions such as potassium hydroxide or hydrochloric acid. The disclosed methods hence enable fabrication of optoelectronic circuitry to include light emitting modules using III-V material systems including, e.g., GaAs, AlGaAs, GaP, InGaP, InGaAsP, GaN, AlGaN, or InGaN.

Examples of Substrates Used in Fabrication

Examples of a substrate and fabrication method integrating AlGaAs optical heterostructures and silicon electronics, enabling wireless, optically powered inorganic optoelectronics for cell-scaled sensors will be discussed below. The optical images and data from example sensors fabricated using some embodiments of the disclosed technology will also be discussed below.

There are three primary challenges to integrating AlGaAs optical heterostructures and silicon electronics at the micron-scale for wireless, optically powered inorganic optoelectronics for cell-scaled sensors. First, the two materials systems, silicon and AlGaAs, are not lattice-matched and hence high-efficiency optical heterostructures and high-performance silicon electronics cannot be readily grown on the same substrate. Secondly, the elevated temperature typically required for silicon electronics would damage most AlGaAs optical heterostructures. The second challenge is most notable when considering dopant activation for dopants in silicon. In modern silicon electronics, both n-type and p-type dopants are implanted into a silicon substrate using various techniques including ion-implantation and diffusion. Following the implantation of these dopants, the dopants typically must be activated at temperatures above 1000 degrees Celsius. Although materials like the silicon dioxide and silicon can withstand these elevated temperatures without damage, AlGaAs optical heterostructures often degrade at such temperatures. For example, at temperatures above 600° C., diffusion can occur in our AlGaAs micro-LEDs that damages the quantum wells in the emission region, reducing efficiency. There is no established method by which one could make wireless, cell-scale, integrated optoelectronic circuits on a typical silicon and AlGaAs substrate that can be released from the substrate.

A solution to the first challenge has been addressed in this patent document, including the transfer method that allows for the growth of the AlGaAs optical heterostructure on a separate GaAs (or similarly lattice-matched) substrate before transfer to another substrate. The second and third challenges can also be overcome by using a substrate that allows for high-performance silicon electronics but requires no additional anneals at temperatures above 600 degrees Celsius after the transfer of AlGaAs optical heterostructures. Furthermore, the substrate and fabrication method can enable the final integrated, cell-scale devices to be released from the handle substrate.

In one embodiment of the substrate, we begin with a silicon on insulator (SOI) substrate consisting of a thick 500 micron silicon handle, a thin 500 nanometer buried oxide (BOX), and a 2 micron-thin p-type silicon device layer. A thin, 500 nanometer, layer of phosphosilicate glass (PSG) is deposited on the silicon device layer and then the substrate is annealed at 1050° C. for approximately 5 minutes. This anneal both drives in the phosphorus dopants partially through the silicon device layer and activates them. The remaining PSG glass is then removed in a buffered oxide etch (BOE). At the point the substrate consists of a SOI wafer with a PN-junction formed in the silicon device layer.

Using the transfer method disclosed above, AlGaAs heterostructures can be transferred and adhered to the PN-junction-containing SOI wafer. Because the PN-junction has been formed everywhere on the surface of the substrate, the surface of the substrate is horizontally symmetric and hence no aligned transfer is needed to the substrate.

Figure 6:
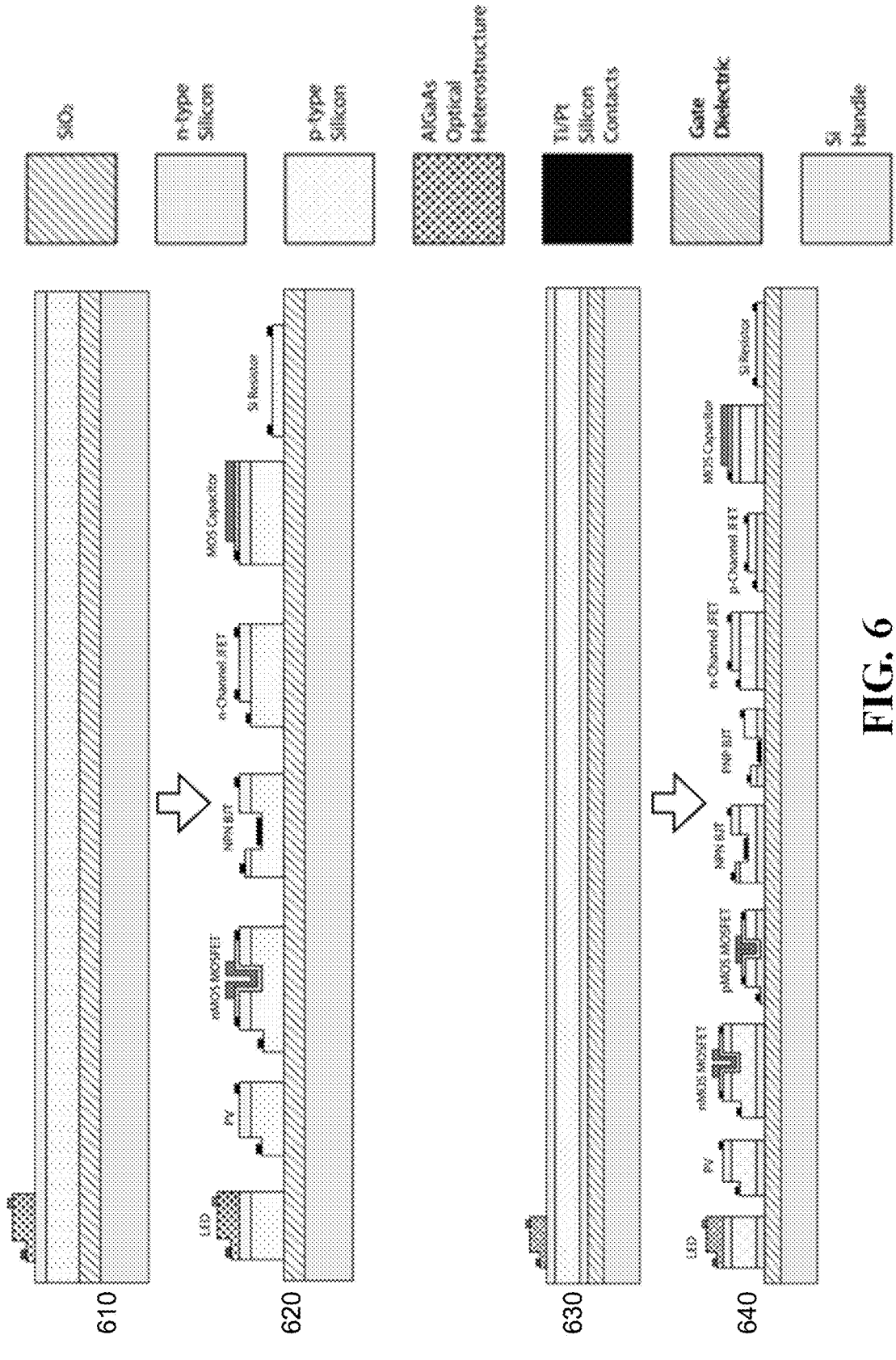
FIG. 6 shows substrate and example fabrication enabling integration of releasable silicon and AlGaAs heterostructures.

FIG. 6 shows substrate and example fabrication enabling integration of releasable silicon and AlGaAs heterostructures, including: PN-junction SOI wafer with AlGaAs heterostructure before etching and metal contacts (610); PN-junction SOI wafer with AlGaAs heterostructures and silicon electronics after etching and metal contacts (620) (example silicon electronics possible shown include photovoltaics (PVs), nMOS MOSFETs, NPN BJTs, n-channel JFETs, MOS capacitors, and silicon resistors; NPN-junction SOI wafer with AlGaAs heterostructure before etching and metal contacts (630); and NPN-junction SOI wafer with AlGaAs heterostructures and silicon electronics after etching and metal contacts (640) (example silicon electronics possible shown include photovoltaics (PVs), nMOS MOS-FETs, pMOS MOSFETs, NPN BJTs, PNP BJTs, n-channel JFETs, p-channel JFETs, MOS capacitors, and silicon resistors).

Following the transfer and adhering of the AlGaAs heterostructures to the PN-junction containing SOI wafer, various silicon electronics can be fabricated aligned to the AlGaAs heterostructures down to the nanoscale by etching the silicon device layer to the desired depth and making electrical contact to the n-type and/or p-type silicon within the device layer. As shown in FIG. 6, the silicon devices that can be integrated with AlGaAs heterostructures include, but are not limited to, photovoltaics, nMOS MOSFETs, n-channel JFETs, NPN BJTs, MOS capacitors, and thin-film resistors (610, 620). More generally, an embodiment of the substrate with a NPN-junction in the silicon device layer additionally enables pMOS MOSFETs, p-channel JFETs, and PNP BJTs, which are components useful for more advanced CMOS devices. The above would not be possible with standard CMOS manufacturing methods after the transfer of AlGaAs heterostructures without damage to the AlGaAs heterostructures (630, 640).

Since the PN-junction, or PNP-junction is formed and dopants are activated prior to the transfer of the AlGaAs heterostructures, the AlGaAs is not exposed to those elevated temperatures, addressing the second challenge discussed above.

Figure 7A:
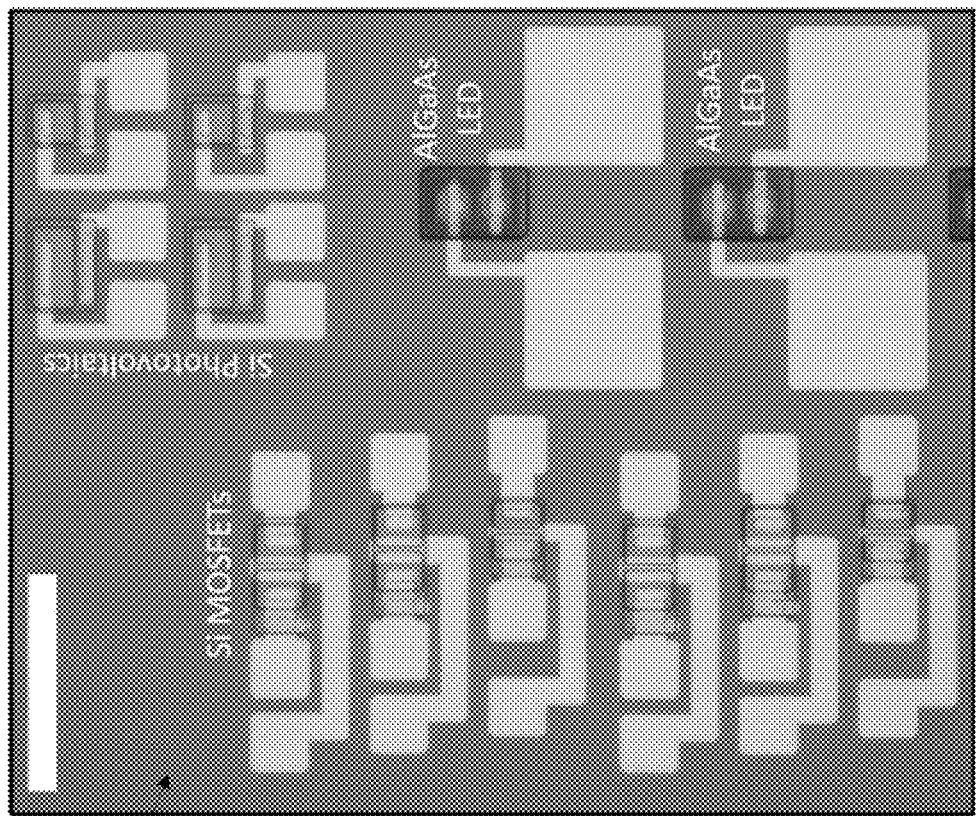

FIG. 7A shows an example configuration including silicon MOSFETs, silicon photovoltaics, and AlGaAs LEDs fabricated on the substrate using the methods implemented based on some embodiments of the disclosed technology. Scale-bar in the upper-left corner is 100 microns. The example configuration also includes metal interconnects electrically connecting silicon MOSFETs, silicon photovoltaics, and AlGaAs LEDs to each other and/or to other components not shown in FIG. 7A. In some embodiments of the disclosed technology, the metal interconnects can be photolithographically formed such that the metal interconnects can have a smallest dimension under 10 microns and distances between electrodes are less than 40 microns. FIG. 7B shows optical image and performance of micron-scale of silicon nMOS MOSFET, FIG. 7C shows optical image and performance of micron-scale of silicon photovoltaic, and FIG. 7D shows optical image and performance of micron-scale of AlGaAs LED. In performance plots, uA is used as an abbreviation for microamps.

To address the remaining third challenge of releasing integrated devices, this patent document presents a fabrication method that uses the above substrate to produce wireless, optically powered inorganic optoelectronics for cell-scaled sensors.

Figure 8:
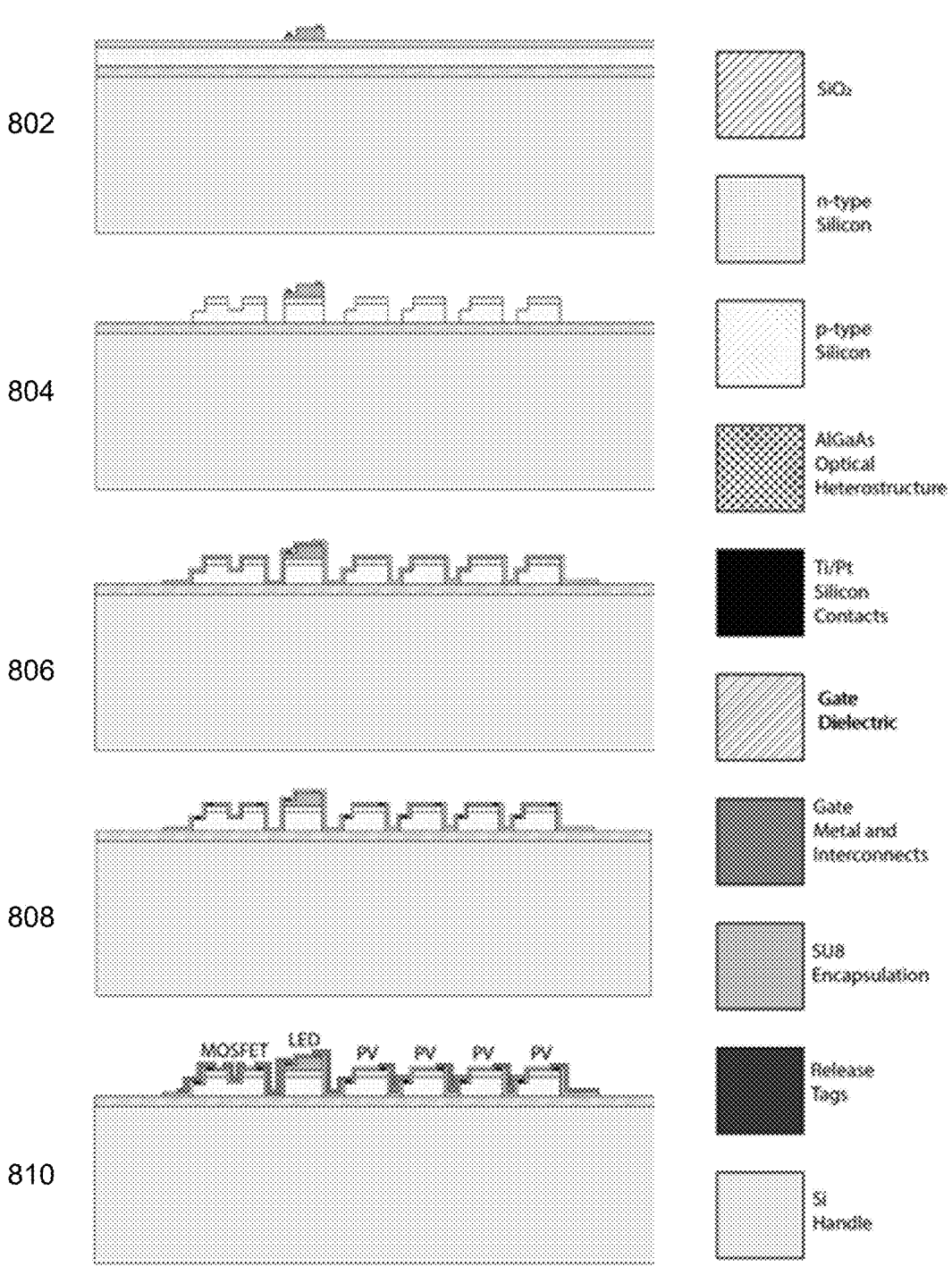
FIG. 8 shows example substrate and fabrication method schematics.
Figure 8:
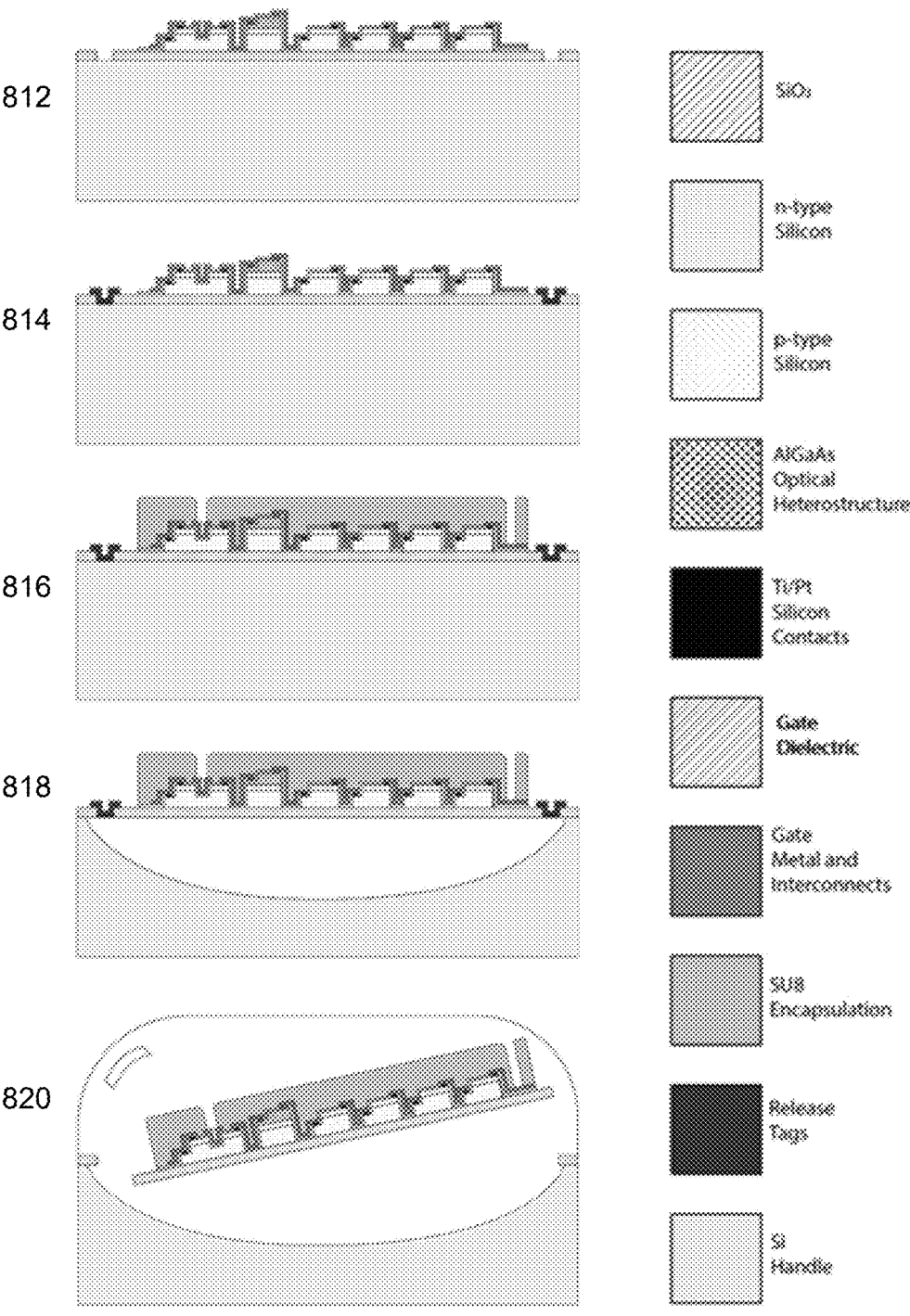

FIG. 8 shows example substrate and fabrication method schematics. At 802, AlGaAs optical heterostructures transferred to the PN-junction containing SOI wafer using the disclosed transfer method. At 804, the silicon device layer is etched to various depths with inductively coupled plasma (ICP) based reactive ion etching using hydrogen bromide (HBr). This step forms the mesa structures for the silicon nMOS MOSFETs and photovoltaics. At 806, a thin dielectric is deposited using ALD serving as both an insulating layer and the gate dielectric. This material can be silicon dioxide, high-k dielectrics like hafnium oxide, or other desired dielectrics. At 808, metal contacts to the n- and p-type silicon are deposited (the oxide is removed in the contact openings prior to deposition). The device is then annealed at 350° C. in argon to form ohmic contacts to the silicon. Other metal or silicide contacts may be used as alternatives. At 810, gate metal and metal interconnects are deposited. For example, a series of layers including titanium (40 nanometers) and platinum (60 nanometers) are used as the gate metal. Other metals including, but not limited to, gold, chrome, aluminum, and copper may be used as alternatives. Other semiconductor materials can be used for the gate including, but not limited to, polysilicon and amorphous silicon.

At 812, openings in the BOX of the SOI wafer are etched using reactive ion etching. At 814, release tags are deposited. These tags, which can be materials such as aluminum or photoresist, will serve to suspend the device and hold it in place until release of the devices is desired. At 816, an SU8 photoresist layer is patterned to serve as an encapsulation layer. Openings can be made to expose metal or other materials where desired, for sensing purposing or otherwise. Materials such as silicon dioxide, parylene, or other insulators could be used as alternative encapsulation layers. At 818, the silicon handle underneath the device is etched away using xenon difluoride (XeF2). This isotropic etch is very selective for silicon over any of the other materials exposed (platinum, SU8, and silicon dioxide). In this step, the encapsulated device is suspended in air, held in place only by the small aluminum release tags. Other dry etches like SF6/O2 or wet etches such as potassium hydroxide could be used as alternatives. At 820, the device is released in an etchant selective for the tags. In one embodiment with aluminum release tags, a dilute acid etch, such as hydrochloric acid (HCl) or another solution etchant, such as tetramethylammonium hydroxide (TMAH), can be used which selectively etches the aluminum release tags but does not etch the other exposed materials by any substantial amount. In another embodiment with exposed photoresist release tags, either a dilute base or acetone can be used to release the devices without etching the other exposed materials. The solution can then be exchanged to deionized water then to any other desired solution.

Figure 9A:
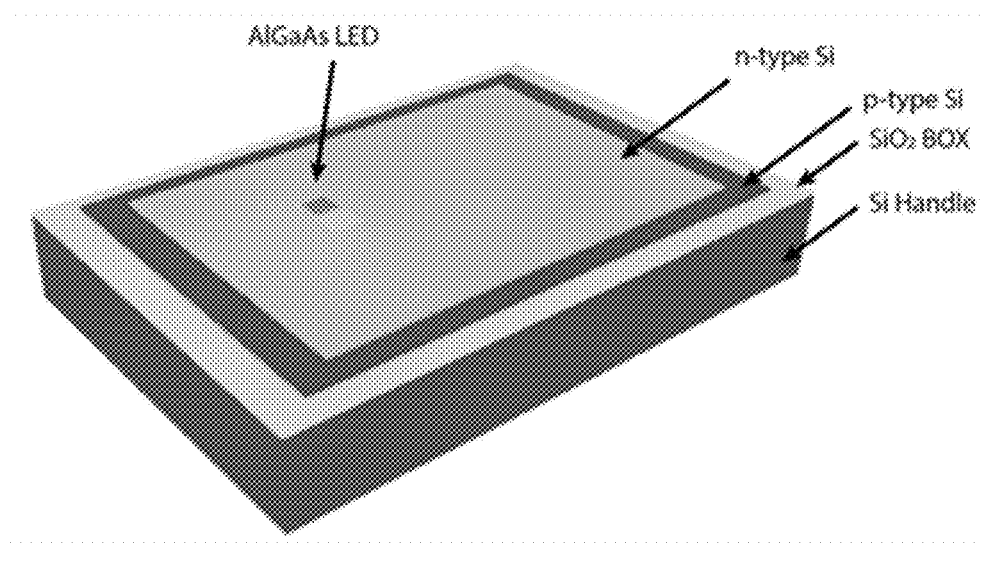
FIGS. 9A-9D show example substrate and fabrication method schematics illustrating a perspective view for releasable, sub-mm$^3$ devices.
Figure 9B:
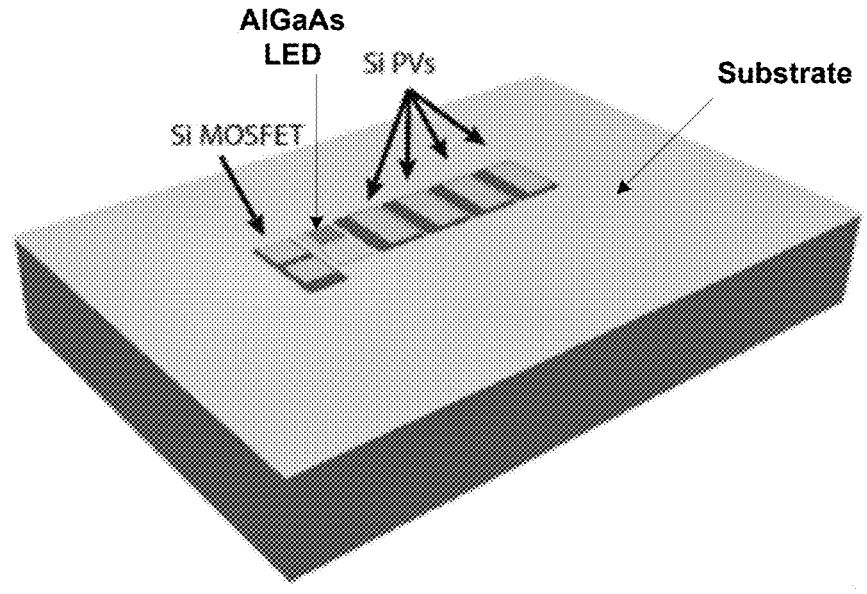
Figure 9C:
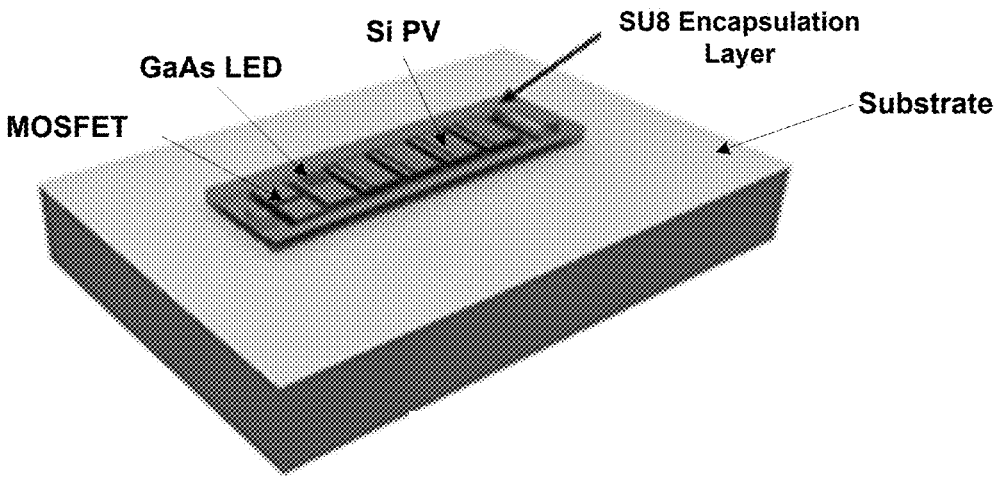
Figure 9D:
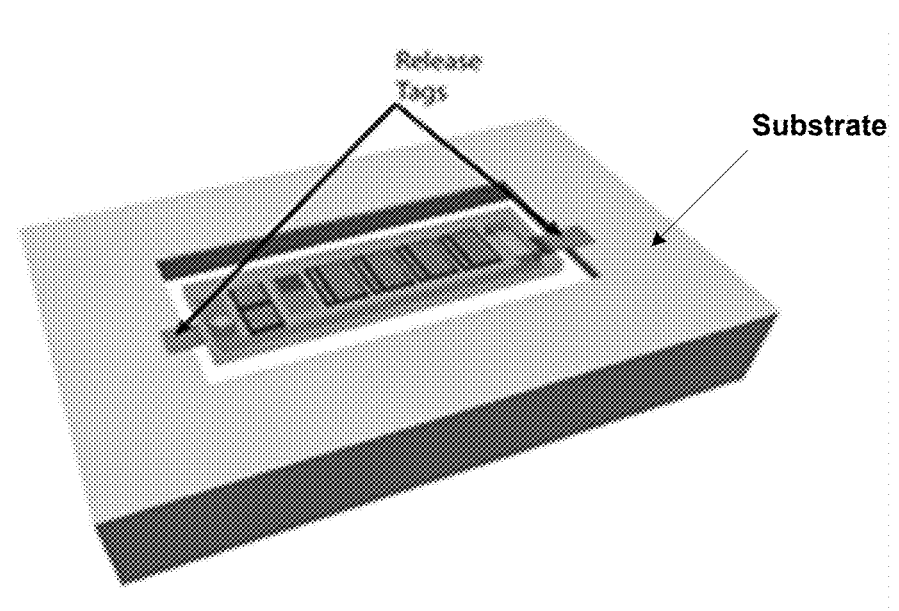

FIGS. 9A-9D show example substrate and fabrication method schematics illustrating a perspective view. FIG. 9A shows an AlGaAs LED formed on a Si substrate including n-type and p-type doped region with an SiO2 box surrounding the n-type and p-type doped region, and Si handle located underneath the AlGaAs LED, n-type and p-type doped region and the SiO2 box. FIG. 9B shows a Si MOSFET, an AlGaAs LED, Si photovoltaics disposed on a substrate. FIG. 9C shows an example without release tags, and FIG. 9D shows another example with release tags. The disclosed substrate and fabrication method, allows for the massive, parallel release of wireless, optically powered cell-scaled sensor or identification devices. The sensor and identification devices can be formed out of any desired configuration of standard silicon electronics, AlGaAs optical heterostructures, and other compatible materials, including, but not limited to, 2D materials (graphene, MoS2, etc.), carbon nanotubes, and transition metal dichalcogenides. In the section that follows, we detail devices enabled by the above disclosure.

In light of the above, the disclosed technology can be implemented to provide a device with opto-electronic circuitry to include a substrate; a photovoltaic module engaged to the substrate and structured to convert light into electricity; and a sensor module engaged to the substrate and coupled to receive power from the electricity generated by the photovoltaic module, the sensor module structured to include a sensing element that is responsive to a target substance to produce a response. The sensor module is further configured to generate, based on the response from the sensing element, an electrical sensor signal indicative of a property of the target substance. This device includes a light-emitting module engaged to the substrate and coupled to receive power from the electricity generated by the photovoltaic module and to receive the electrical sensor signal from the sensor module. The light-emitting module is structured to produce output light that is modulated to carry the electrical sensor signal to wirelessly and optically transmit the electrical sensor signal out of the device. In implementation, the sensing element can be in various configurations, including one or more sensing electrodes, one or more resistors such as a silicon resistor or a nanotube resistor, or other sensing element designs.

The disclosed technology may be implemented to provide a method of making lithographically-formed wireless sensors and devices, wherein integration, packaging, and assembly is carried out in massive parallel through planar photolithography or electron beam lithography. Prior methods for making of wireless devices bulky or serial techniques for 1) integration of dissimilar materials, 2) device isolation, 3) packaging, and 4) assembly. Examples of these prior techniques that are not enabling of the disclosed technology include; wire-bonding, flip-chip bonding, solder bumps, dicing, dice-before-grind, pick-and-place, stacking, and dip coating for encapsulation. Unlike such prior methods, the methods disclosed in this document enable the making of a device comprising a (i) light emitting element module, (ii) a photovoltaic module, and (iii) a sensing or identification module, wherein all components have lithographically-formed electrical interconnects. Additionally, the methods enable the parallel production of devices comprising a (i) light emitting element module, (ii) a photovoltaic module, and (iii) a sensing or identification module.

Based on the disclosed technology, the photolithographic or e-beam lithographic formation of electrical contacts allows for size scales and dimensions of electrical interconnects that would otherwise be unattainable. In some embodiments, the wireless optoelectronic devices enabled could have electrical interconnects with one dimension at or below 40 microns, 30 microns, 20 microns, 15 microns, 10 microns, 5 microns, 3 microns, or 1 micron. In other embodiments, the pitch between electrical interconnects connecting dissimilar materials could be at or below 40 microns, 30 microns, 20 microns, 10 microns, 5 microns, or 3 microns.

Based on the disclosed technology, the use of all planar techniques for (i) lithographic integration, (ii) interconnects, (iii) assembly, (iii) packaging, and (iv) release of the devices from the substrate on which they were built, allows for size scales and dimensions of the fully-integrated, stand-alone device that would otherwise be unattainable. In some embodiments, the wireless optoelectronic devices enabled could have dimensions below 1 mm$^3$, (500 μm)$^3$, (400 μm)$^3$, (300 μm)$^3$, (200 μm)$^3$, or (100 μm)$^3$.

Based on the disclosed technology, sensing a target subject by implanting a sensor on the target subject without having a physical connection to the sensor can be achieved. In this method; illumination light is directed onto the sensor implanted on the target subject to cause a photovoltaic module in the sensor generate electric power for operating the sensor so that the generated electric power powers (1) a sensor module which performs a sensing operation on the target subject to generate an electrical sensor signal indicative of a property of the target subject, and (2) a light-emitting module coupled to receive the electrical sensor signal from the sensor module and operable to produce output light that is modulated to carry the electrical sensor signal. The output light is used to wirelessly and optically transmit the electrical sensor signal out of the device.

In another embodiment of the disclosed technology, a device with opto-electronic circuitry includes a substrate, a photovoltaic module engaged to the substrate and structured to convert light into electricity, an identification module engaged to the substrate and coupled to receive power from the electricity generated by the photovoltaic module, the identification module configured to generate an electrical identification signal indicative of an identity of the device, and a light-emitting module engaged to the substrate and coupled to receive power from the electricity generated by the photovoltaic module and to receive the electrical identification signal from the identification module, the light-emitting module structured to produce output light that is modulated to carry the electrical identification signal to wirelessly and optically transmit the electrical identification signal out of the device.

In some embodiments of the disclosed technology, the output light can be modulated using a pulsed-position modulation scheme. For example, the signal measured from the sensor module or the identification module is encoded in the timing between pulses.

Examples of Wireless, Self-Powered Sensor Devices

Figure 10C:
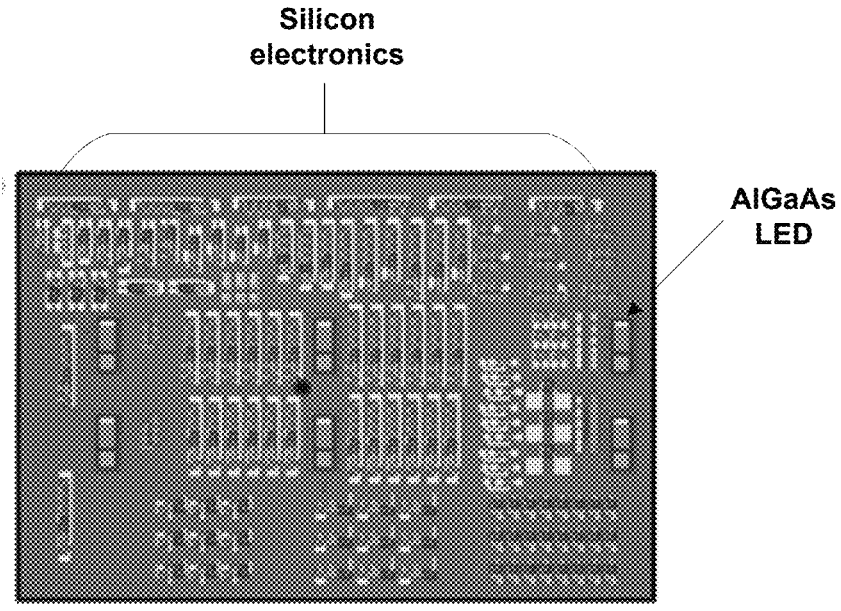
Figure 10D:
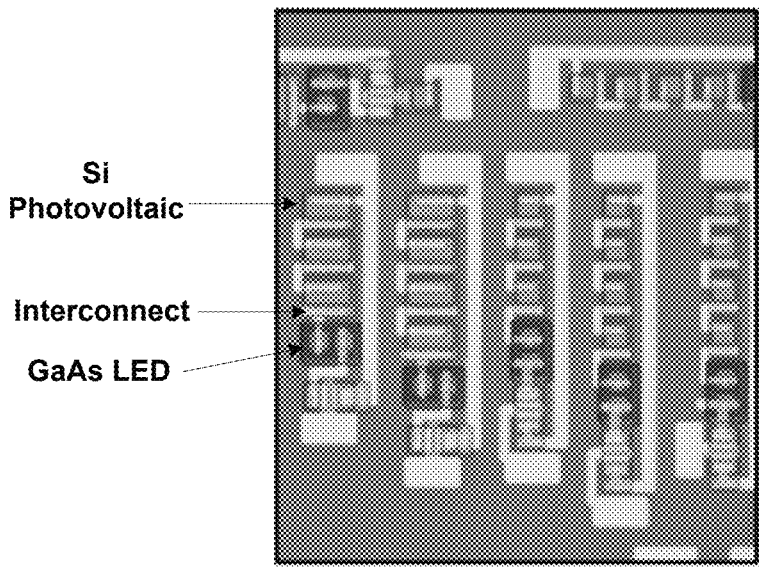

FIGS. 10A-10D show examples of large-scale integration of micron-scale silicon and III-V electronics and optoelectronics for releasable devices. Specifically, FIG. 10A shows an optical image of an 18 by 18-millimeter chip where thousands of GaAs micro-LEDs have been transferred to a silicon-on-insulator substrate with a PN-junction formed in the silicon handle. Silicon electronics were then fabricated aligned to the GaAs micro-LEDs. An example die on the chip is shown in FIG. 10B after transfer of GaAs LEDs, but before silicon electronics are fabricated. FIG. 10C shows an example die after silicon electronics have been integrated. Devices shown in FIG. 10D includes micron-scale voltage sensors that are optically powered with silicon photovoltaics and are optically readout with GaAs micro-LEDs.

Using the above disclosed transfer method, substrate, and fabrication methods, we regularly produce optoelectronic integrated circuits (ICs) that are capable of being released from the silicon handle. FIG. 10A shows an example on an 18 millimeter chip where AlGaAs micro-LEDs and silicon electronics have been integrated, including optically powered, cell-scale sensor and identification systems. On such a chip, there are about 50 different IC designs and thousands of individual ICs. In some embodiments of the disclosed technology, the AlGaAs micro-LEDs and silicon electronics integrated on the chip are electrically connected to each other through metal interconnects that are photolithographically formed such that the metal interconnects can have a smallest dimension under 10 microns and distances between electrodes of the AlGaAs micro-LEDs are less than 40 microns.

Figure 11C:
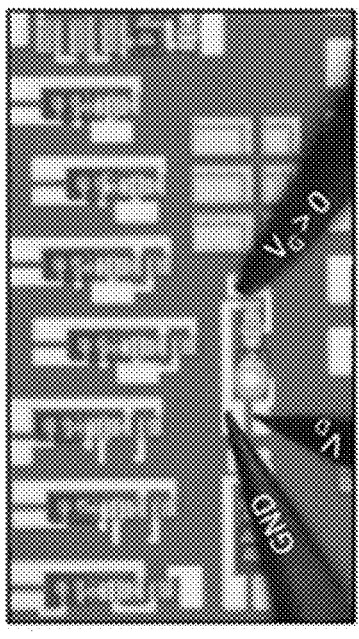
Figure 11B:
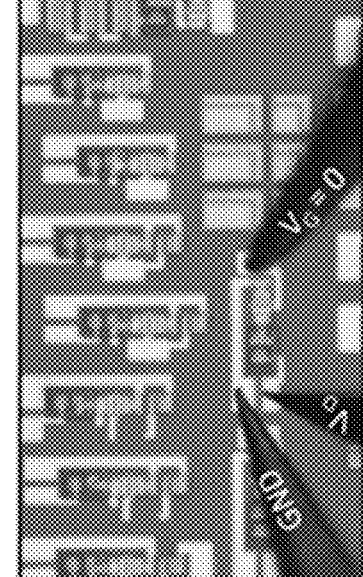
Figure 11A:
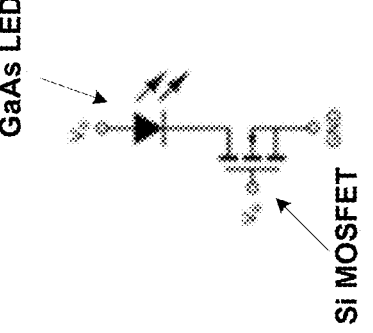
Figure 11F:
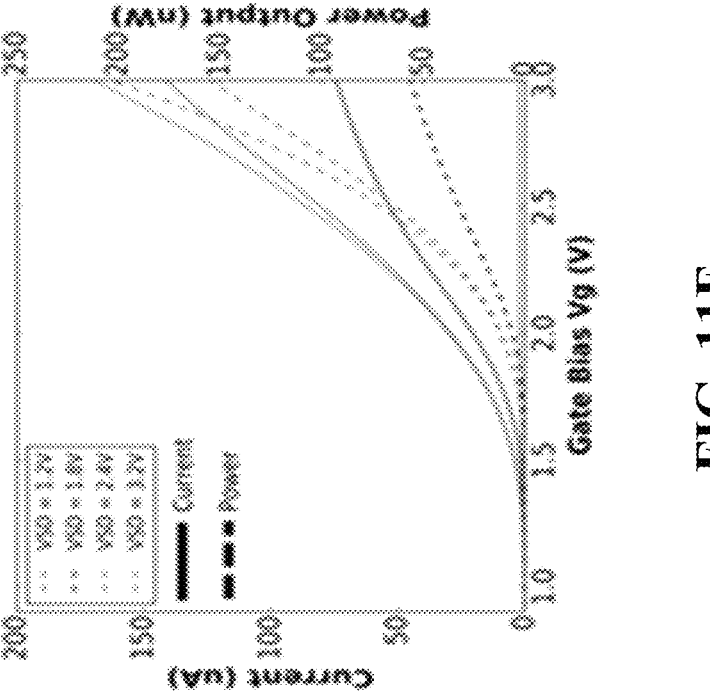
Figure 11E:
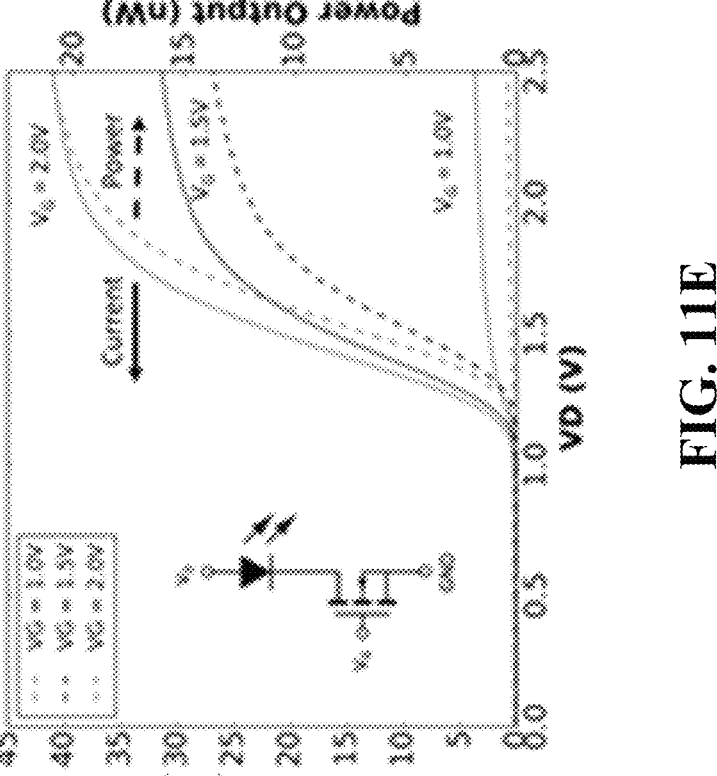

FIGS. 11A-11F show an example integrated circuit of GaAs LED and silicon MOSFET. Specifically, FIG. 11A shows a circuit schematic of integrated device with a GaAs LED in series with a Si MOSFET. FIG. 11B shows an optical image taken with a CCD camera, capable of monitoring near-infrared light, of the integrated LED/MOSFET system under no gate-source bias. The silicon MOSFET shown, as well as all other silicon electronics shown in the image, was fabricated after transfer of the GaAs LED. FIG. 11C shows an optical image of the same device with a positive gate-source bias applied showing light being emitted from the LED. FIG. 11D shows optical images 1102, 1104, 1106 taken at higher magnification of the integrated device in order of increasing gate-source bias from 1102 to 1106. For scale, channel length of the silicon MOSFET is approximately 2 microns. FIGS. 11E and 11F show performance of the integrated LED/MOSFET system. As one example of the integration of AlGaAs micro-LEDs and silicon electronics, FIGS. 11A-11F show optical images and data from a AlGaAs LED and a silicon nMOS MOSFET connected in series. The electric signal input into the gate of the MOSFET is converted into an optical signal out of the micro-LED that can be readout using a CCD camera or other photodetector.

Figure 12C:
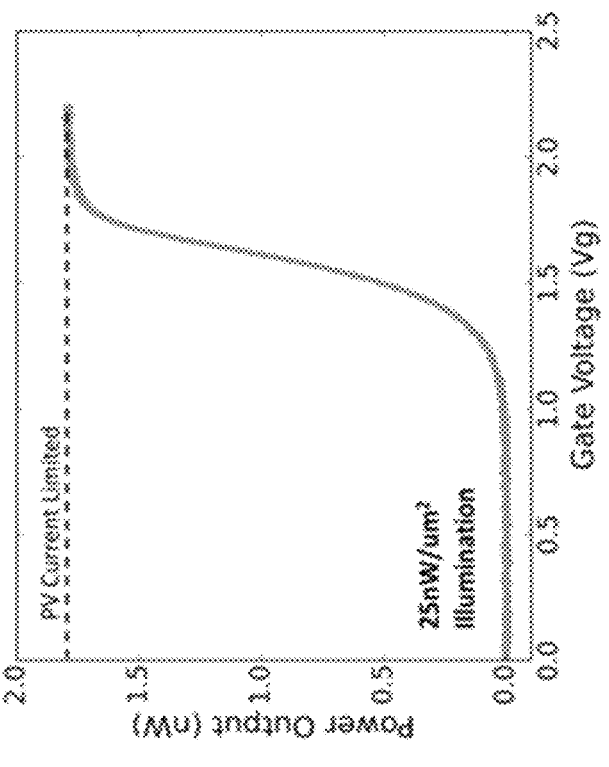
FIGS. 12A-12F show examples of optically powered voltage sensor fabrication on a release-compatible substrate.
Figure 12B:
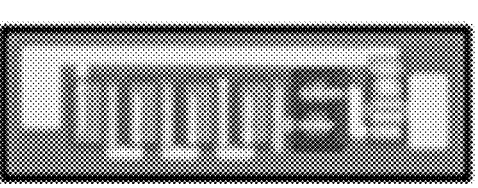
Figure 12A:
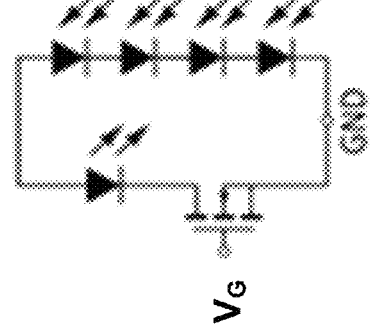
Figures 12D, 12E, 12F:
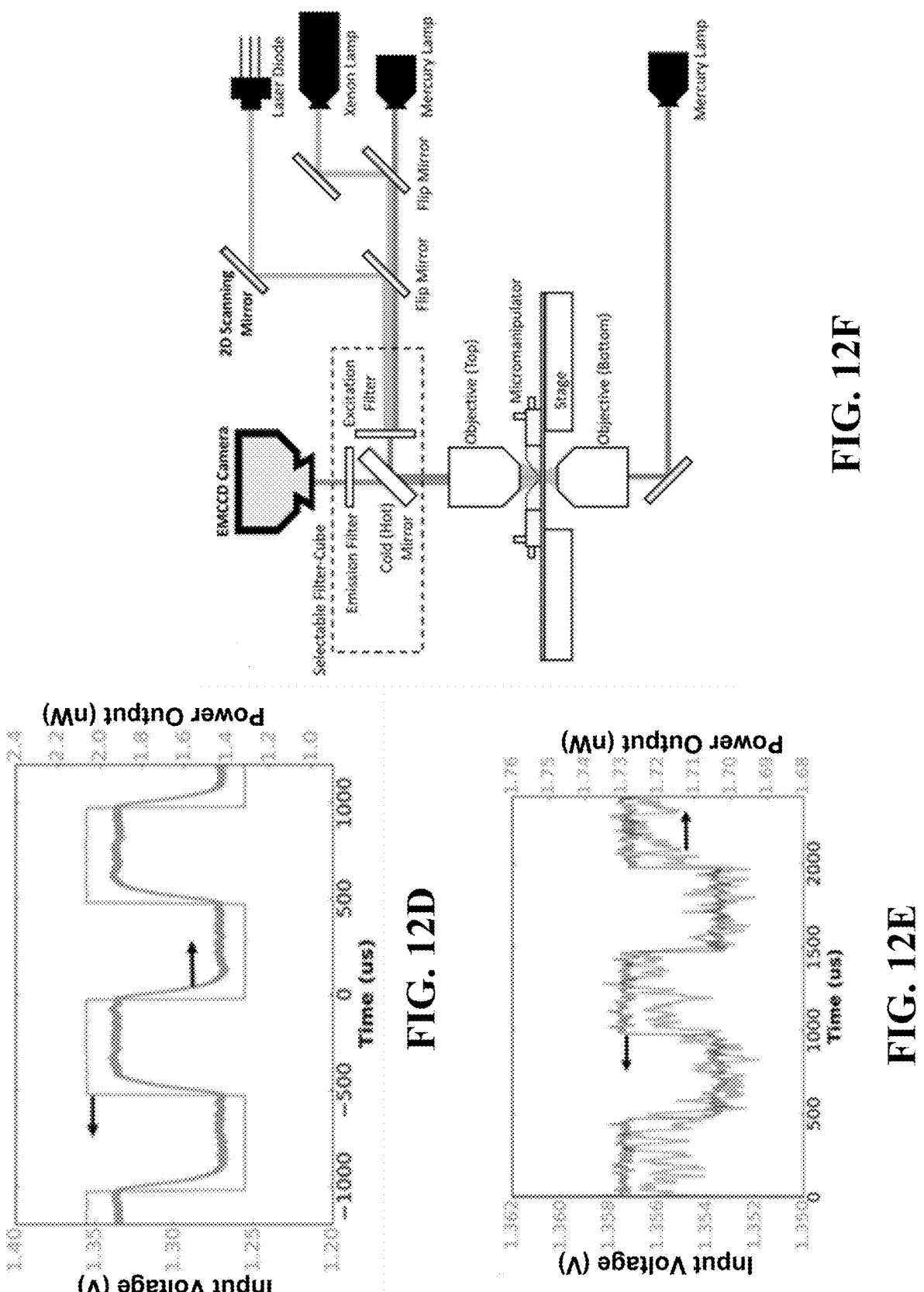

FIGS. 12A-12F show examples of optically powered voltage sensor fabrication on a release-compatible substrate. Specifically, FIG. 12A shows a circuit schematic of the optically powered, wireless, cell-scaled voltage sensor. FIG. 12B shows an optical image of device on a release-compatible substrate. FIG. 12C shows a power output of the micro-LED as a function of gate voltage. The device is under 25 nanowatts per micron squared illumination, providing the power to the circuit. FIGS. 12D-12E show power outputs of the micro-LED and input voltage signal for different input voltage pulses. These plots illustrate the conversion of the input electrical signal to an optical signal out. FIG. 12F shows an example measurement setup for powering and monitoring the optically powered, voltage sensor.

The voltage sensor implemented based on some embodiments of the disclosed technology may include silicon photovoltaics, a silicon MOSFET, and a AlGaAs micro-LED. In an implementation, the approximately 50-micron by 200-micron voltage sensor is capable of detecting changes in voltage in its surroundings and then communicating out those changes optically using the integrated micro-LED. In this embodiment, the signal is encoded in changes in intensity of the LED. More complex embodiments can have additional features to reduce noise and encode the output signal using other encoding schemes as shown in FIGS. 5A-5F where the voltage sensor is sensitive to approximately 10 nanovolts/Hz$^{1/2}$ and the signal is communicated out through pulse position modulation. Both wireless, optically powered, cell-scale sensors could be used for applications such as recording neural activities at the individual cell level.

Figure 13A:
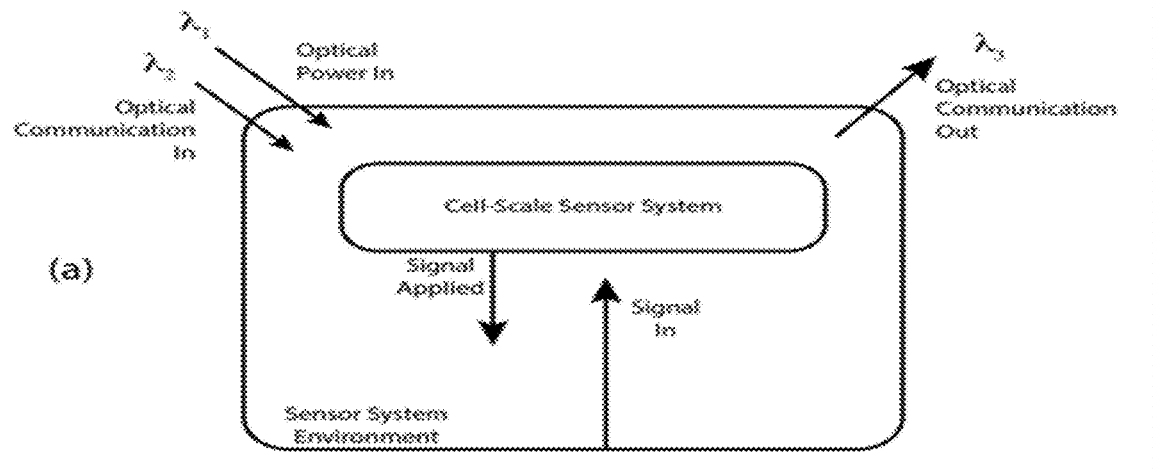
FIGS. 13A-13E show example wireless, optically powered, cell-scale sensor systems and applications.

FIGS. 13A-13E show example wireless, optically powered, cell-scale sensor systems and applications. Specifically, FIG. 13A shows schematic of a wireless, optically-powered cell-scale sensor system under use. The same techniques used to produce the voltage sensor described above can enable various embodiments of wireless, optically-powered cell-scale sensor systems. A general schematic of such a sensor system is shown in FIG. 13A. Optical power, $\lambda 1$, is supplied to the system along with any optical communication in, $\lambda 2$. Using the power supplied and any communication in, the cell-scaled sensor system can apply a signal if desired. Signal in from the sensor system environment is then communicated out optically, $\lambda 3$. The sensor systems can make using of voltage sources, current sources, sensors that measure voltages, and sensors that measure currents.

Figure 13B:
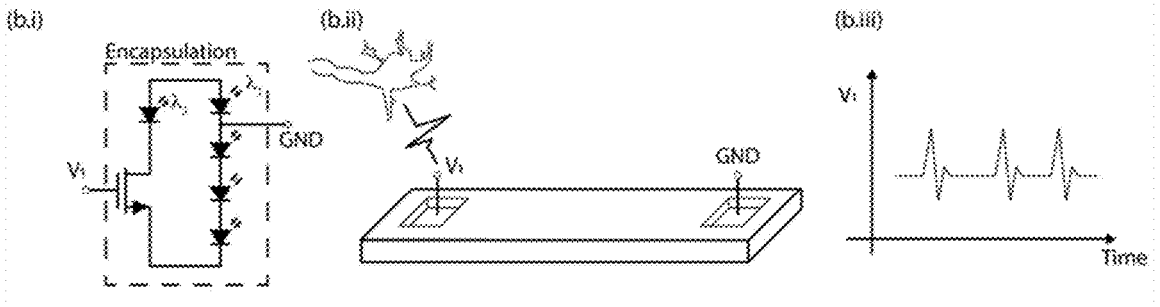
Figure 13C:
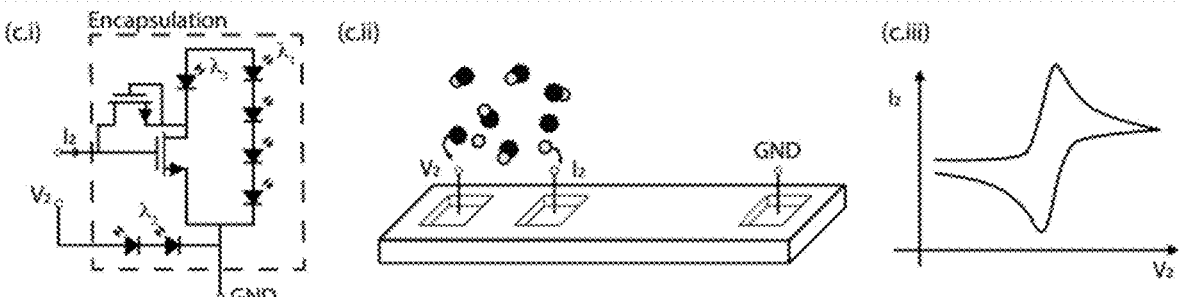

FIGS. 13B-13E detail example wireless, optically-powered, cell-scaled sensor system embodiments and applications enabled by the present disclosure. FIG. 13B shows, as an example application for a voltage sensor, a device capable of measuring the electrical signals from an individual neuron, including schematics of (b.i) circuit, (b.ii) example application of detecting neuron activity, and (b.iii) signal in reconstructed from $\lambda 3$. FIG. 13C shows, as an example application for a current sensor with voltage source controlled with $\lambda 2$, a device capable of performing and measuring cyclic-voltammetry in a small volume of fluid to, for example, determine the presence of dopamine released from a cell including schematics of (c.i) circuit, (c.ii) example application of performing cyclic-voltammetry, and (c.iii)

Figure 13D:
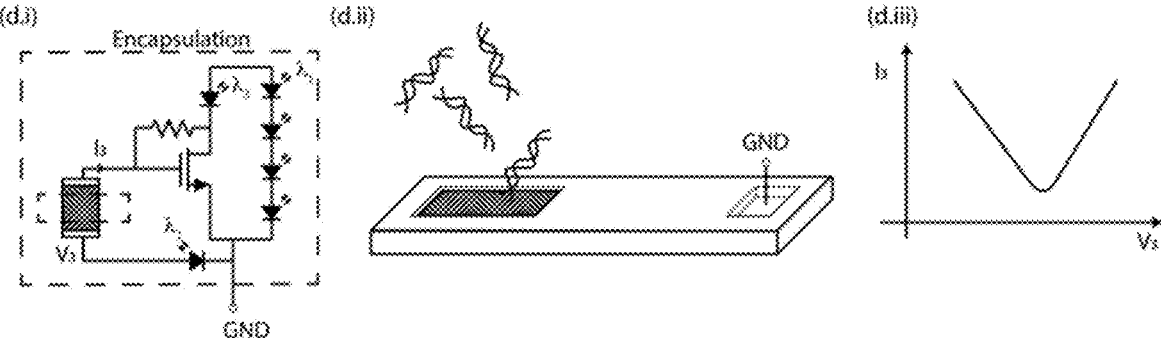
Figure 13E:
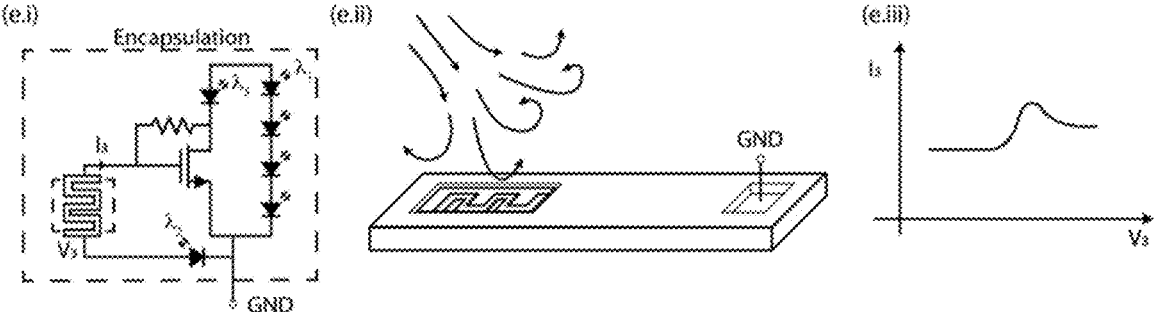

21 cyclic voltammogram reconstructed from λ3. FIG. 13D shows, as an example application for a graphene sensor with voltage source controlled with λ2, a device capable of measuring the response of graphene or carbon nanotubes to the presence of DNA, including schematics of (d.i) circuit, (d.ii) example application of detection DNA, and (d.iii) signal in reconstructed from λ3. FIG. 13E shows, as an example application for a silicon sensor with voltage source controlled with λ2, a device capable of measuring the response of a silicon resistor to changes in temperature allowing for monitoring of flow and turbulence in fluids, including schematics of (e.i) circuit, (e.ii) example application of detection of fluid flow or temperature change, and (e.iii) signal in reconstructed from λ3.

The disclosed technology in this patent document can be used for monitoring electrical and chemical signals at the cellular-scale. Examples of the monitoring method can include monitoring electrical signals from neurons, nerve cells, cardiomyocytes, and other biological systems. In some implementations, many devices in parallel may be used for brain mapping of neural activity. Examples of the monitoring method also include monitoring chemical signals or chemical composition of, or near, cells or other biological systems. Here, many devices in parallel may be used for mapping of chemical release in the brain (or mapping changes in chemical composition). Examples of the monitoring method include the chemical detection of glucose levels, oxygen content, A1C testing, PH, pregnancy, infectious disease, and drug-of-abuse. Examples of the monitoring method include monitoring changes in electrical signals from nanoscale materials (metal electrodes, tunnel junctions, carbon nanotubes, graphene, other 2D materials, etc.) that are sensitive to particular chemical species in solution. Examples of the monitoring method also include monitoring electrical signals, chemical signals, temperature, or flow in nanoscale or microscale fluid channels. Many devices in parallel could be used for mapping flow, turbulence, or solution conductivity in microfluidic channels. Examples of the monitoring method include the transfer method may be used to make micro-shanks with integrated AlGaAs LEDs for optogenetics.

Example of Alternative Methods Used in Fabrication

Figure 14:
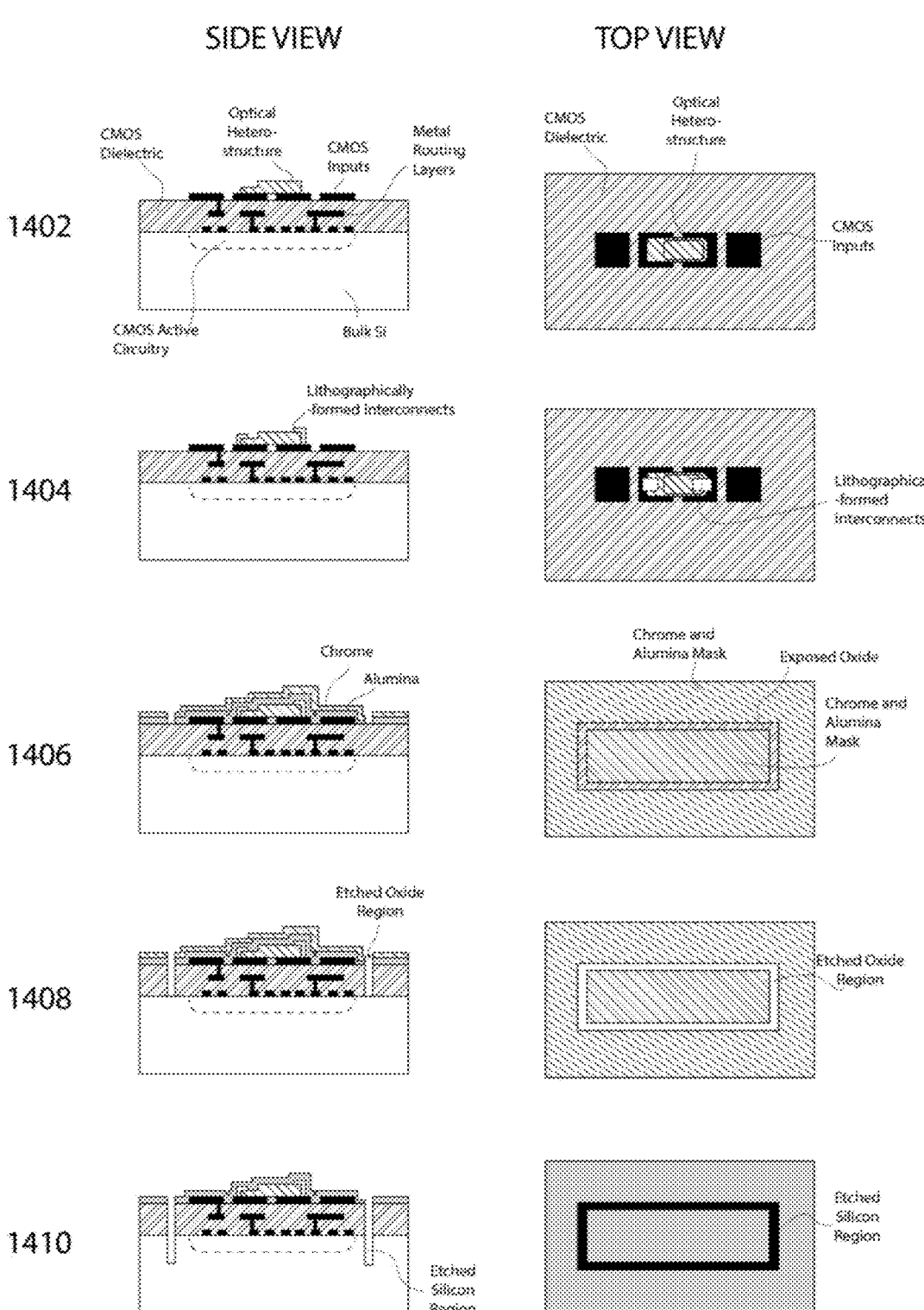
FIG. 14 shows an example alternative release method for integrated CMOS and AlGaAs heterostructure cell-scale sensors.
Figure 14:
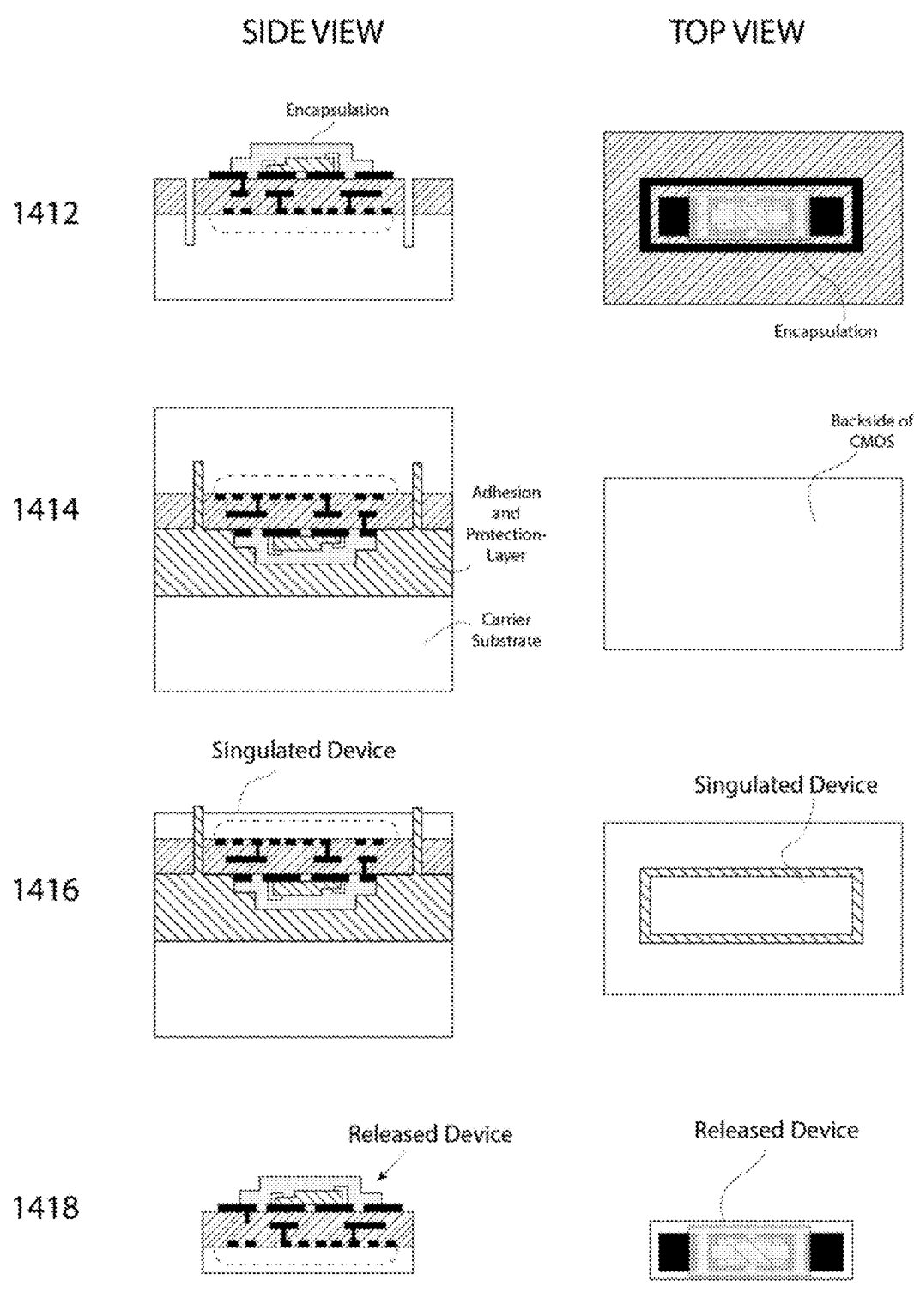

FIG. 14 shows an example alternative release method for integrated CMOS and AlGaAs heterostructure cell-scale sensors. At 1402, AlGaAs optical heterostructure is transferred and adhered to CMOS circuitry using the disclosed methods. At 1404, metal interconnects are patterned to electrically connect the anode and cathode of the AlGaAs optical heterostructure to the corresponding connections of the CMOS circuit through the CMOS inputs. At 1406 dual chrome and alumina masking layers are deposited and patterned to protect the circuitry and optical heterostructure during etches through the CMOS dielectric layers and the underlying bulk silicon substrate. Other masking layers can be used as long as they are selective enough for the subsequent etches. Other such combinations can include combinations of photoresist, alumina, tantalum oxide, titanium dioxide, chrome, and nickel. At 1408, reactive-ion etching (RIE) through the CMOS dielectric is used to etch the desired size and shape of the released, cell-scale device. An example RIE chemistry suitable for such etching is inductively coupled plasma RIE consisting of $CHF_3$ and $O_2$. At 1410, the chrome is selectively removed in chrome etchant and the remaining alumina is used to mask the circuitry and the optical heterostructure during deep reactive ion etching (DRIE) into the silicon. The etch depth into the silicon is used to determine the eventual thickness of the singulated device or die. At 1412, the alumina is selectively removed in, e.g., a $BCl_3$ RIE chemistry, and a conformal encapsulation layer coats the device and is then opened at the desired inputs of the CMOS circuitry. SU8, parylene, silicon dioxide, and other insulating materials can be used as an encapsulation layer. At 1416, for both protection and adhesion, the device is bonded, device-side down to a transfer substrate. The adhesion/protection layer is chosen so that it can be selectively etched with respect to the other exposed materials. Examples of the materials that could be used for this layer include, but are not limited to, photoresist, PMMA, and dicing saw tape. A silicon, sapphire, or other substrate could be used for the transfer substrate. At 1416, deep reactive-ion etching (DRIE) or wafer grinding is used to etch down to the desired device thickness. At this point the device is only held to the transfer substrate via the adhesion/protection layer. At 1418, the device can then be release by using a wet or dry etches selective for the adhesion/protection layer.

In one embodiment, UV dicing saw tape can be used for the adhesion/protection layer. The device can then be released by flood exposing the tape to UV light.

In one embodiment, silicon dioxide can be used as the encapsulation layer, photoresist can be used as the adhesion/protection layer, and the release of the device can be accomplished using an acetone solution. This alternative method enables the release of cell-scale devices from both SOI substrates or standard CMOS substrates.

The examples of fabrication methods described represent a novel method for singulation of dies or devices over some other dicing methods. Some implementations of those other dicing techniques for die singulation tend to be limited in one or more aspects, including, for example: (1) dicing may not be a fully parallel process, (2) the thickness of the dicing saw may dictate the smallest size of the trench or cut made, and (3) the available shapes may be geometrically limited by the size and direction of the blade. The above methods do not suffer from any of these limitations. With respect to (1), the processes listed above can be achieved fully in parallel through planar lithographic methods. A full wafer can be processed in a single process, reducing time and cost of singulation. With respect to (2), the thickness of the etch is only limited by lithography and the aspect ratios possible with the RIE techniques used. Trenches with dimensions at or below 40 microns, 30 microns, 20 microns, 10 microns, 5 microns, 2 microns, and 1 micron are attainable using the disclosed methods. With respect to (3) the geometric shapes are only limited to what shapes can be lithographically produced on the substrates. Each individual die can have its own arbitrary shape on the same wafer.

Although methods disclosed here can be used for wireless optoelectronic device singulation, these methods may also be used for singulation of CMOS or other semiconductor dies with much less space etched between devices, or kerf, lost during process. Size scales of kerf possible with the disclosed techniques represent a departure from what is achievable through prior techniques. For example, on a CMOS process, if dies are to be singulated into 200 μm dies using a dicing saw with 40 micron thickness, approximately 40 percent of the wafer would be lost to dicing. In comparison, if dies are to be singulated into 200 μm dies using 2 micron trenches as achievable with the disclosed methods, only approximately 2 percent of the wafer would be lost during singulation.

Additional Sensor Examples

Figure 15B:
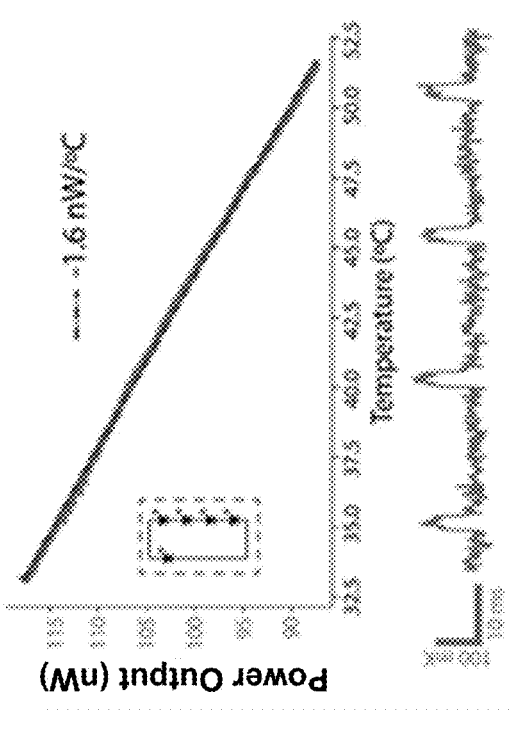
FIGS. 15A-15D illustrate examples of sensors made by using large-scale integration of micron-scale silicon and III-V electronic and optoelectronics for releasable devices.
Figure 15A:
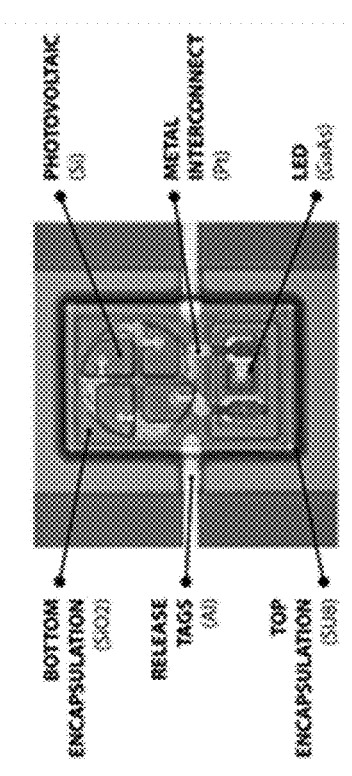
Figure 15D:
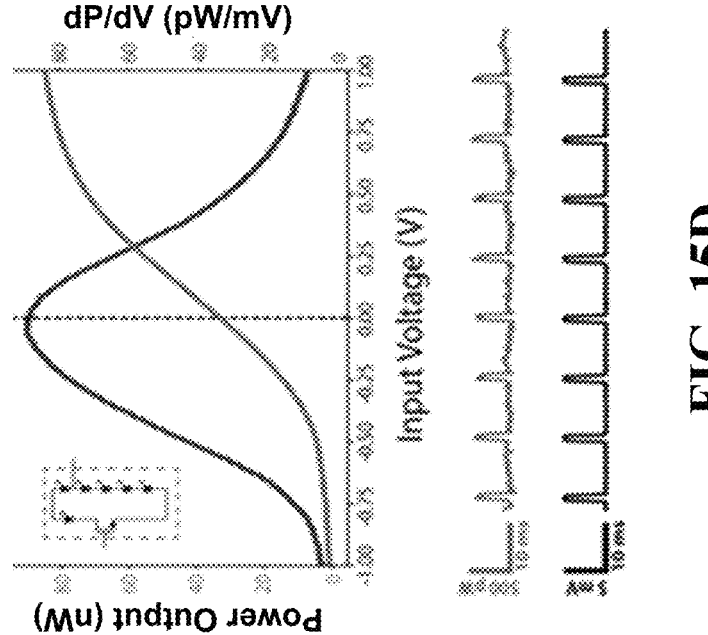
Figure 15C:
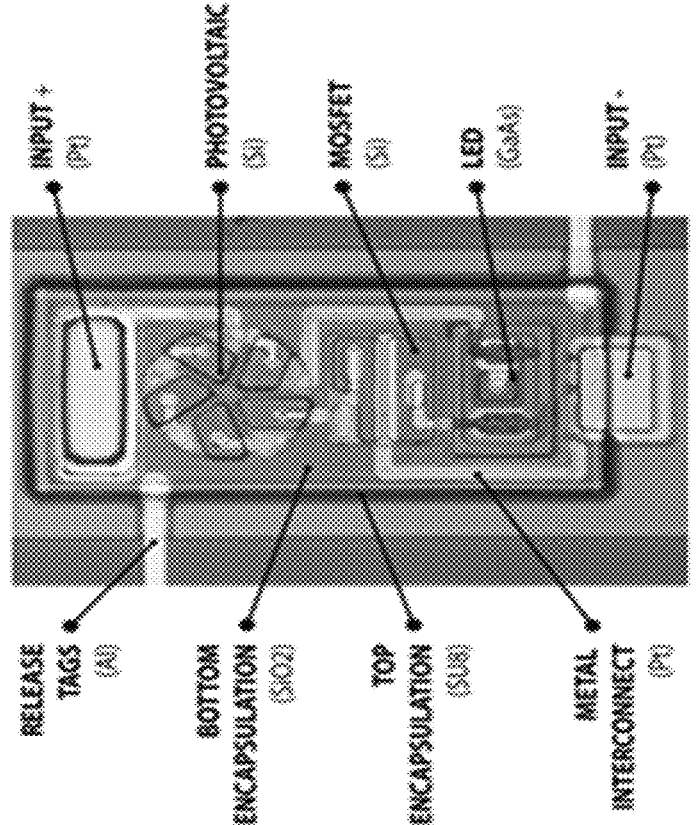

FIGS. 15A-15D illustrate examples of sensors made by using large-scale integration of micron-scale silicon and III-V electronic and optoelectronics for releasable devices. Specifically, FIG. 15A shows a temperature sensor having silicon photovoltaics and AlGaAs micro-LED. FIG. 15B shows sample characteristics of the temperature sensing of the temperature sensor in FIG. 15A showing a linear optical response as a function of temperature (top), a circuit schematic of the temperature sensor (insert) and high-speed temperature sensing of pulsing heating using a resistive element next to the temperature sensor (bottom). FIG. 15C shows a voltage sensor having silicon photovoltaics, a silicon MOSFET, AlGaAs micro-LED, and input electrodes. FIG. 15D shows sample voltage sensor characteristics represented by the power output as a function of input voltage of the sensor in FIG. 15C (top) and high-speed voltage sensing data from the optical voltage sensor (bottom). Devices shown here are capable of release from the substrate and encapsulated. Interconnects for the GaAs micro-LEDs were made using photolithography as opposed to wire-bond or flip-chip methods.

Figure 16B:
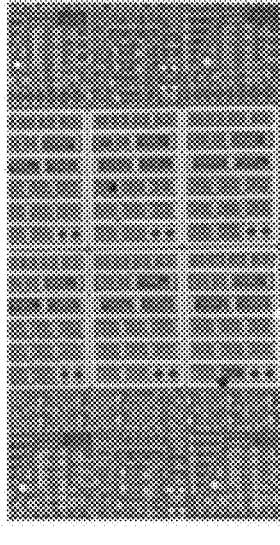
FIGS. 16A-16G show examples of wireless, optically powered optoelectronic cell-scale sensors.
Figure 16D:
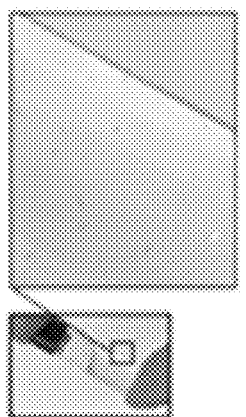
Figure 16A:
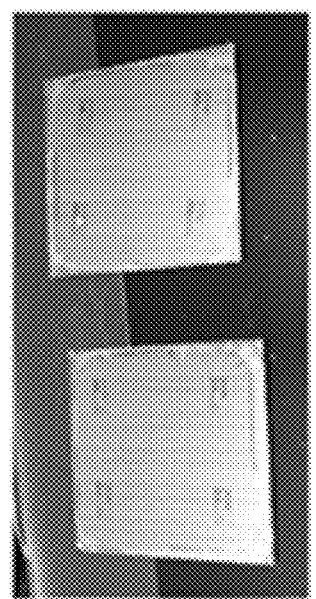
Figure 16C:
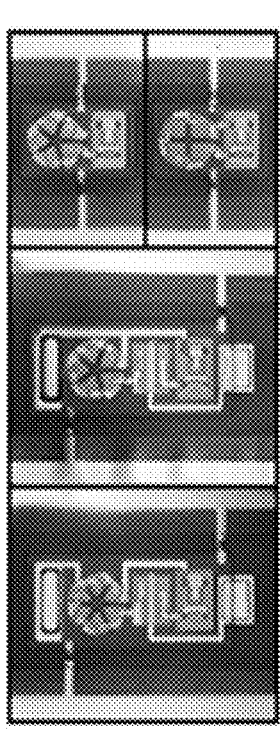
Figures 16E, 16F, 16G:
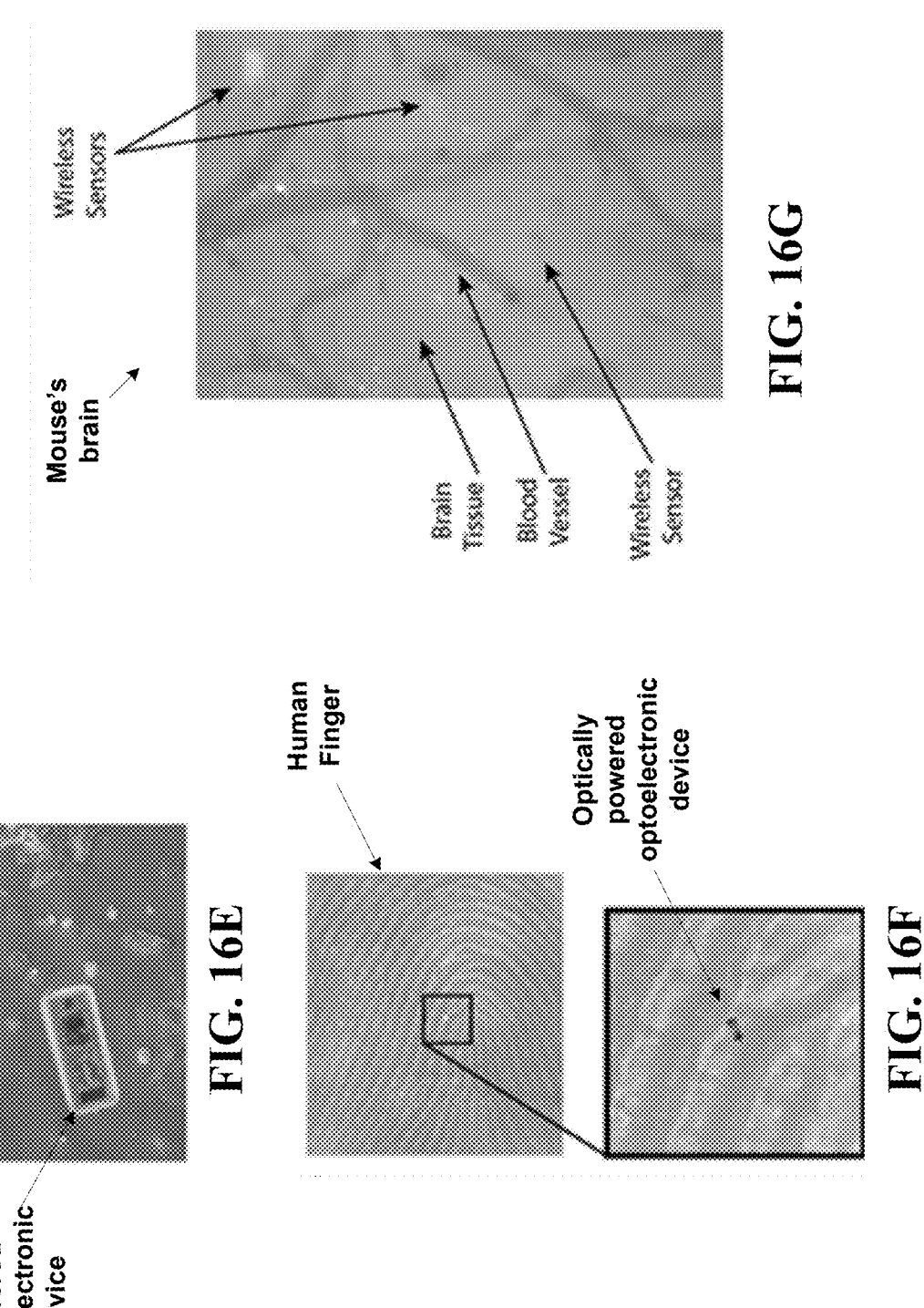

FIGS. 16A-16G show examples of wireless, optically powered optoelectronic cell-scale sensors. Specifically, FIG. 16A shows 18 mm by 18 mm chips containing thousands of releasable wireless, optically-powered optoelectronic cell-sized sensors that were integrated with photolithographically defined interconnects. FIG. 16B shows an example die showing the release structure of the devices. FIG. 16C shows optically powered, wireless optoelectronic voltage and temperature sensors that are suspended over a trench as described in the above materials. FIG. 16D shows wireless devices released into solution by selective chemical etching of the release tags. FIG. 16E shows released wireless optically powered optoelectronic device next to cardiac cells. FIG. 16F shows released wireless optically powered optoelectronic device on a ridge of a human finger. FIG. 16G shows wireless optically powered optoelectronic temperature sensors implanted in-vivo to a mouse's brain.

The above and other technical features as disclosed can be used to construct optically powered, wireless sensors at small scales of 10,000 times smaller in volume than some mm-scale sensors by integrating optical components (such as light-emitting diodes) with interconnects that are photolithographically defined while avoiding bulky wire-bond or flip-chip bonding for forming interconnects of greater than 40 μm pitch. By using photolithographically defined interconnects, the disclosed technology in this document can be used achieve smaller size integration, e.g., with all electrical interconnect having a dimension less than 10 microns.

In some example applications, a method of transferring AlGaAs system heterostructures may include: producing AlGaAs system heterostructures on a substrate with an "intermediate selective etch layer" between heterostructures and the substrate; depositing a layer of polymer on the optical heterostructures; etching the substrate in a chemical mixture (citric acid and hydrogen peroxide); etching the intermediate selective etch layer in a distinct chemical mixture (diluted HF); transferring the polymer/optical heterostructure system to a transfer substrate. In an embodiment, a method of transferring AlGaAs system heterostructures may include removing the polymer via a dry etching method; adhering the devices to the transfer substrate by deposition a conformal insulating material (ALD, PECVD, etc.). In an alternative embodiment, a method of transferring AlGaAs system heterostructures may include: producing AlGaAs system optical heterostructures on a substrate with an "intermediate selective etch layer" between optical heterostructures and the substrate; depositing a layer of polymer on the optical heterostructures, etching the intermediate selective etch layer in a distinct chemical mixture (diluted HF); and transferring the polymer/optical heterostructure system to a transfer substrate.

As an example substrate implemented based on some embodiments of the disclosed technology, a substrate for the integration of silicon electronics and AlGaAs system optical heterostructures may include: an optical heterostructure transferred to a silicon-on-insulator substrate with; a silicon handle with thickness less than 100 microns. A pn-junction has been formed in the silicon handle with dopants activated; the silicon device layer has been etched; electrical contact has been made to at least one area of n-type silicon; and electrical contact has been made to at least one area of p-type silicon.

As an example device implemented based on some embodiments of the disclosed technology, an electronic and optical device may include: a substrate; and a device comprising; at least one micron-scale AlGaAs system optical heterostructure; at least one transistor; at least one photovoltaic. The three components are connected with electrical interconnects in a configuration such that under illumination of electromagnetic radiation, electric current passes through the three components, changes in voltage or current in connections made to the transistor result in modulations in current passing through the AlGaAs optical heterostructure, and modulation of said electric current causes changes in the amount of the light emitted from the AlGaAs system optical heterostructure. All dimensions of the components of the device is less than 1000 microns.

In the disclosed examples, "wireless" is used to describe a device that does not have electrical interconnects emanating from the device. The electrical interconnects are internal to the device. If a device is said to be a wireless with all dimensions less than 100 microns, there are no electrical interconnects extending outside of the 100 micron boundary bounding the device. "cell-scaled," "cellular-scale," and "cell-sized" are used interchangeably to describe an object that has all dimensions less than 500 microns on every side. The term "micro-LED" is used to describe a light-emitting diode that has all dimensions less than 1 millimeter on every side. The term "heterostructure" is used to describe any series of layers of materials grown on a substrate to produce an optical or electronic device. The term "optical heterostructure" is used to describe structures or layers of materials grown on a substrate that have the capability to emitting or absorbing light. This would include light-emitting diodes, lasers, photovoltaics, as well as other optical elements. The terms "AlGaAs material system," "AlGaAs system," "AlGaAs," "AlGaAs/GaAs," and "AlGaAs/GaAs system" are used interchangeably to describe any material or layers of materials that are sufficiently lattice-matched to GaAs to allow for optical heterostructures to be produced. This would include material systems such as GaAs, AlGaAs, AlGaInP, GaAsP, AlInP, and/or GaP which can all be grown on the same substrate to produce optical heterostructures. The term "AlGaAs heterostructure" is used to describe a heterostructure or optical heterostructure made of materials from the AlGaAs system. "Fabrication," "micro-fabrication," and "nano-fabrication" are used interchangeably to describe fabrication or production of devices at the nanometer to millimeter scale. "Light" and "electromagnetic radiation" are used interchangeably. "BJT" is an abbreviation for bipolar junction transistor. "JFET" is an abbreviation for junction gate field-effect transistor.

In some embodiments of the disclosed technology, the photovoltaic provides power, the silicon circuitry measures, amplifies, and encodes the signal, and finally, the signal is optically communicated out using the LED functionality of the PVLED.

Figures 17A, 17B:
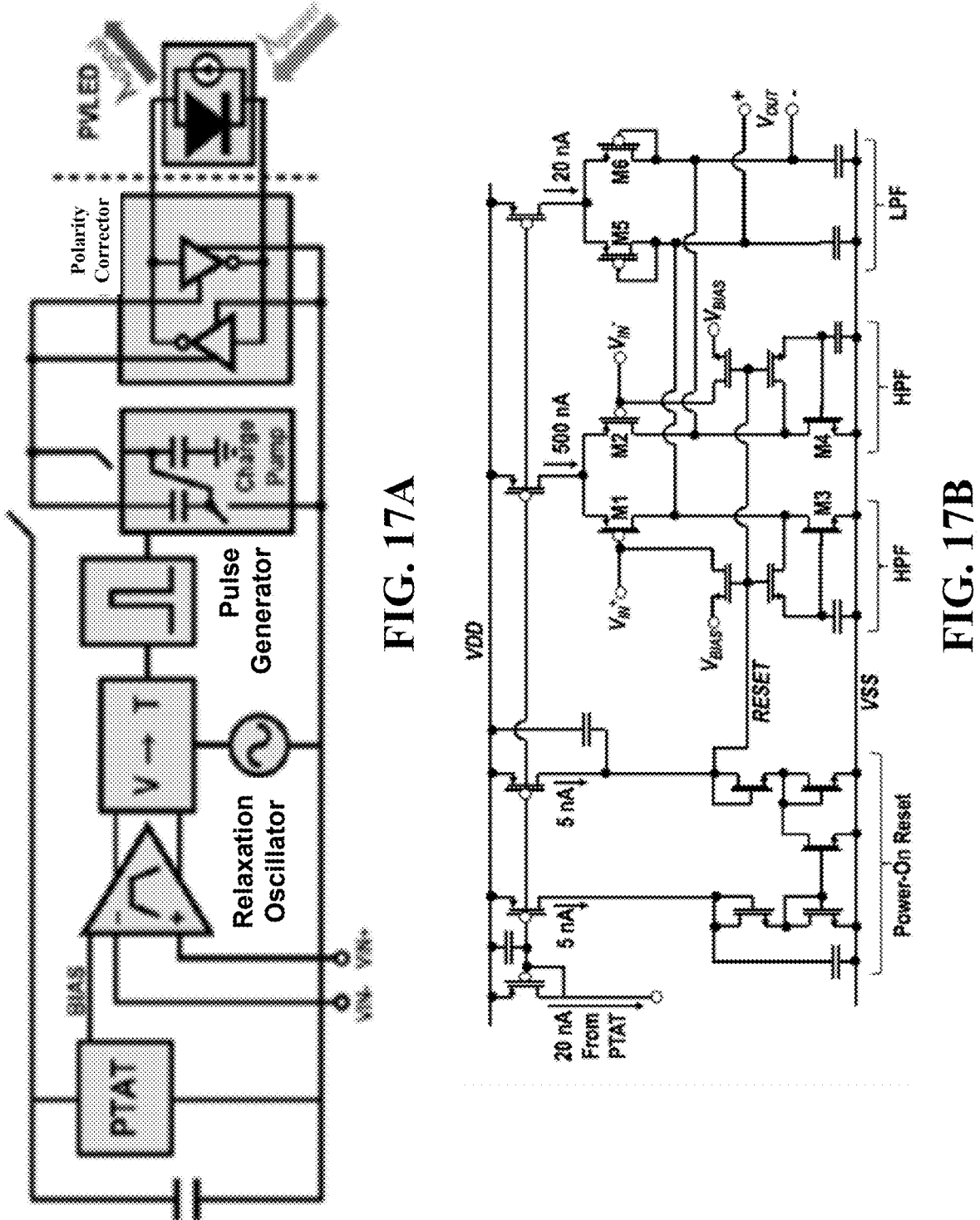
FIGS. 17A-17B show a block diagram of the system and a schematic of the amplifier that boosts the differential signal between the two sensing electrodes that are spaced ~150 μm apart to sample the electric fields generated by nearby neurons.

FIGS. 17A-17B show a block diagram of the system and a schematic of the amplifier that boosts the differential signal between the two sensing electrodes that are spaced ~150 μm apart to sample the electric fields generated by nearby neurons. Specifically, FIG. 17A shows a block diagram of the system implemented based on some embodiments of the disclosed technology. FIG. 17B shows schematic of an amplifier including a startup circuit and a filtering circuit. Approximately one half of the total current from the PVLED (500 nA of 1 μA) is used to provide the low noise amplification through the input differential pair (M1 & M2). A pair of NFETs (M3 & M4) act as high-pass active loads: the amplifier output is fed back to the gates from through transistors acting as pseudo resistors and shunted by MOS capacitors. Thus, M3 and M4 provide a low impedance at low frequencies (<<1 Hz) but a high resistance in the neural band of interest (>10 Hz). Finally, a pair of diode-connected PFETs (M5 & M6) provide a matched load for a controlled mid-band gain, with parallel MOS capacitors setting a low-pass corner at about 10 KHz to suppress higher-order aliasing terms. Because the high-pass load would lead to a prohibitively long start-up time while illumination may be transitory, the high-pass resistors are briefly set to a low resistance state at VDD startup, to rapidly calibrate out DC offsets and bias state before switching to their normal high-resistance state. The amplifier and all other circuits are biased from a supply-invariant PTAT-like current source to provide immunity to variations in VDD during illumination fluctuation or output optical pulse generation.

Figure 18A:
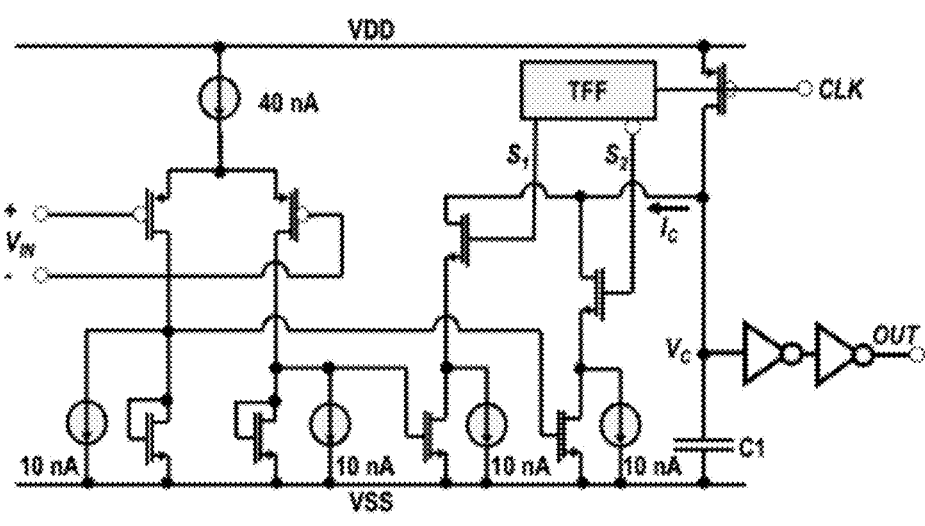
FIGS. 18A-18D show that the amplifier drives the pulse-position encoder, while a 10 KHz relaxation oscillator generates a periodic pulse, which charges capacitor C1 to VDD.
Figure 18B:
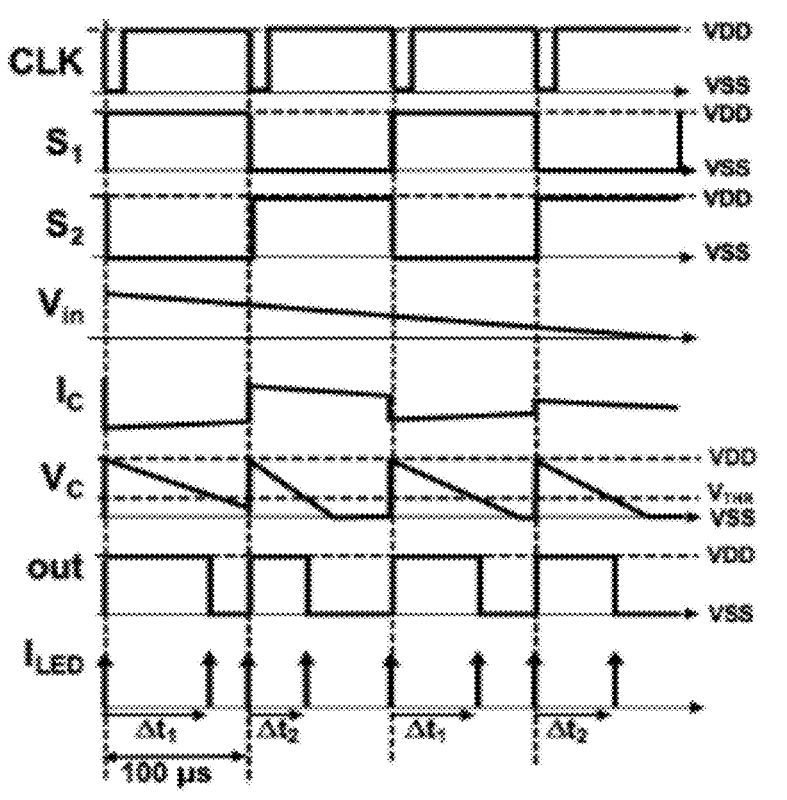
Figure 18C:
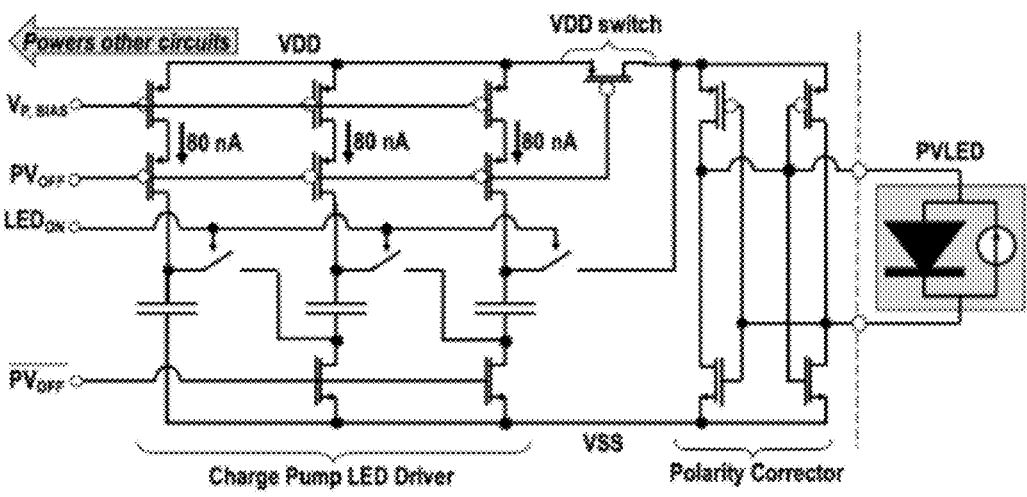
Figure 18D:
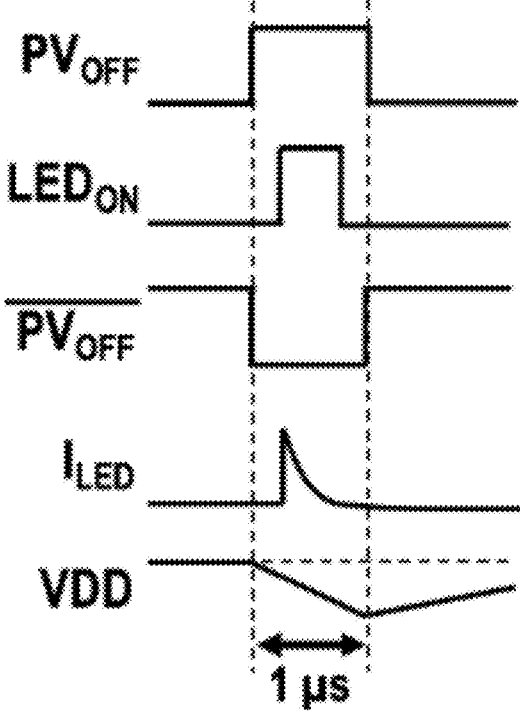

Some embodiments of the disclosed technology can use a pulse position modulation (PPM) for signal encoding for its high information per photon efficiency. FIGS. 18A-18D show that the amplifier drives the pulse-position encoder, while a 10 KHz relaxation oscillator generates a periodic pulse, which charges capacitor C1 to VDD. Specifically, FIGS. 18A and 18B show the PPM encoder and associated timing diagram, and FIGS. 18C and 18D show the pulse generator and its associated timing diagram. After this reset, the capacitor is discharged by one of two differential currents generated from the output of the amplifier. The result is a square-wave whose duty cycle reflects the inverse of the measured voltage. Fixed currents bound the duty cycle to a range between 20% and 80%. A T-flip-flop selects which of the two complementary currents discharges the capacitor, alternating between clock cycles, chopping like this allows separation of signal from fluctuations due to slow-changing light level. The resulting square-wave is passed through a delay-line of current-starved inverters, and edges are combined to generate pulses on both the rising and falling edges of the square wave. The timing of these signals is illustrated in FIGS. 18B and 18D. A wider pulse disconnects VDD from the PVLED for 1 μs, and two other pulses switch a 3-capacitor (1.2 pF each) charge pump, switching from a parallel configuration to a series configuration, and connecting to the PVLED to deliver a sharp (<100 ns) current pulse. Each cycle of the relaxation oscillator generates two light pulses through the PVLED, one at the beginning of the cycle, and the other between 20 μs and 80 μs later, where this time difference denotes the input voltage. To ensure that the VDD does not drop excessively during the pulsing events (when it is disconnected from the PVLED), 16 pF of decoupling capacitance is installed. In addition, because the PVLED can only supply a finite amount of instantaneous current, and to avoid an excessive supply ripple, the charge pump capacitors are recharged slowly over about 10 μs. A 20 μs minimum pulse spacing ensures that the charge pump is fully charged before each pulse. Finally, to ease the assembly of PVLED and CMOS, a cross-coupled rectifier (polarity corrector) is implemented to ensure the system functionality regardless of the polarity of the PVLED on its pads.

Figures 19A, 19B:
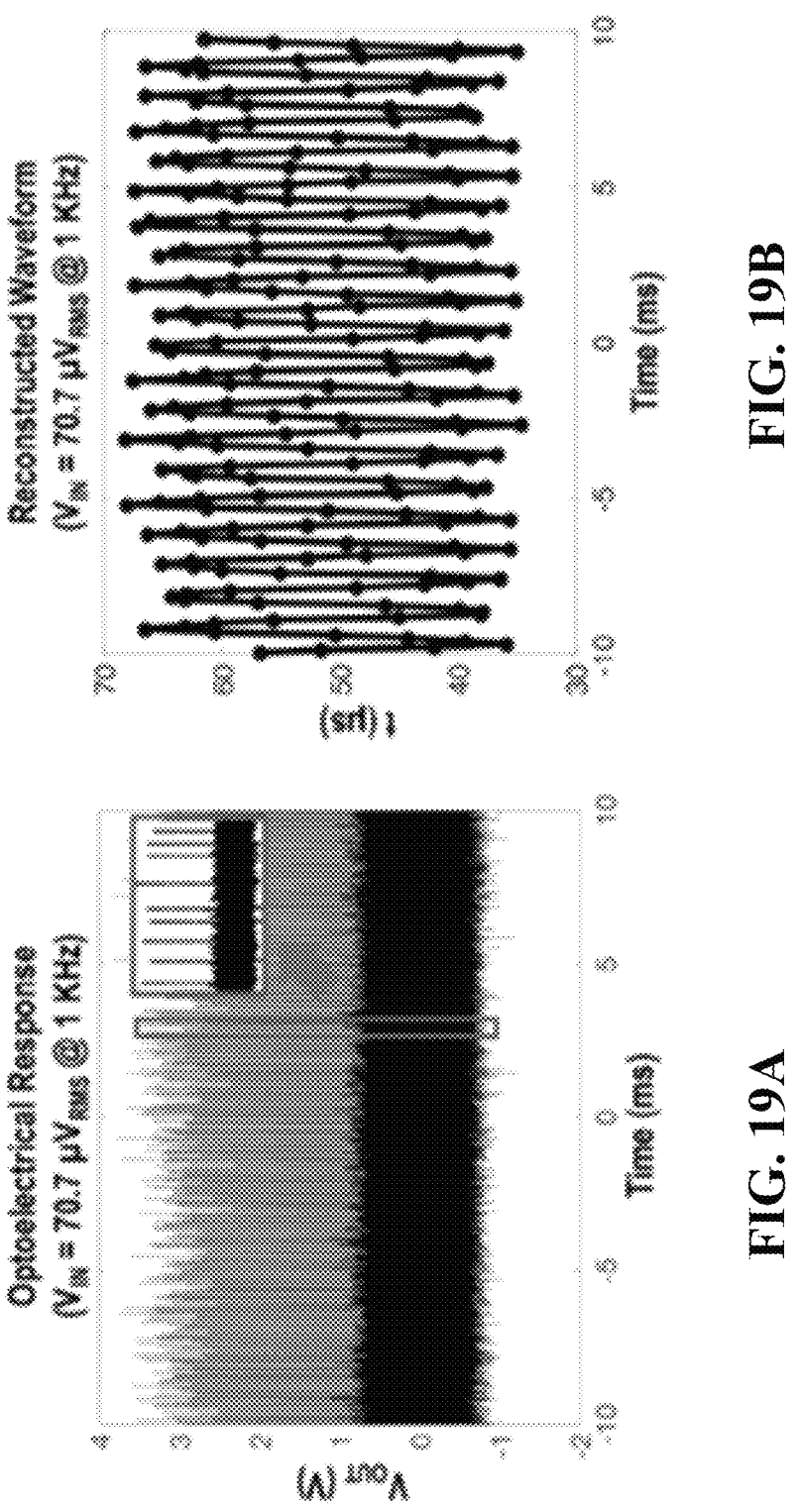
FIGS. 19A-19B show example measurement of optical output pulse (FIG. 19A), and associated reconstructed 1 KHz waveform (FIG. 19B).
Figures 19C, 19D:
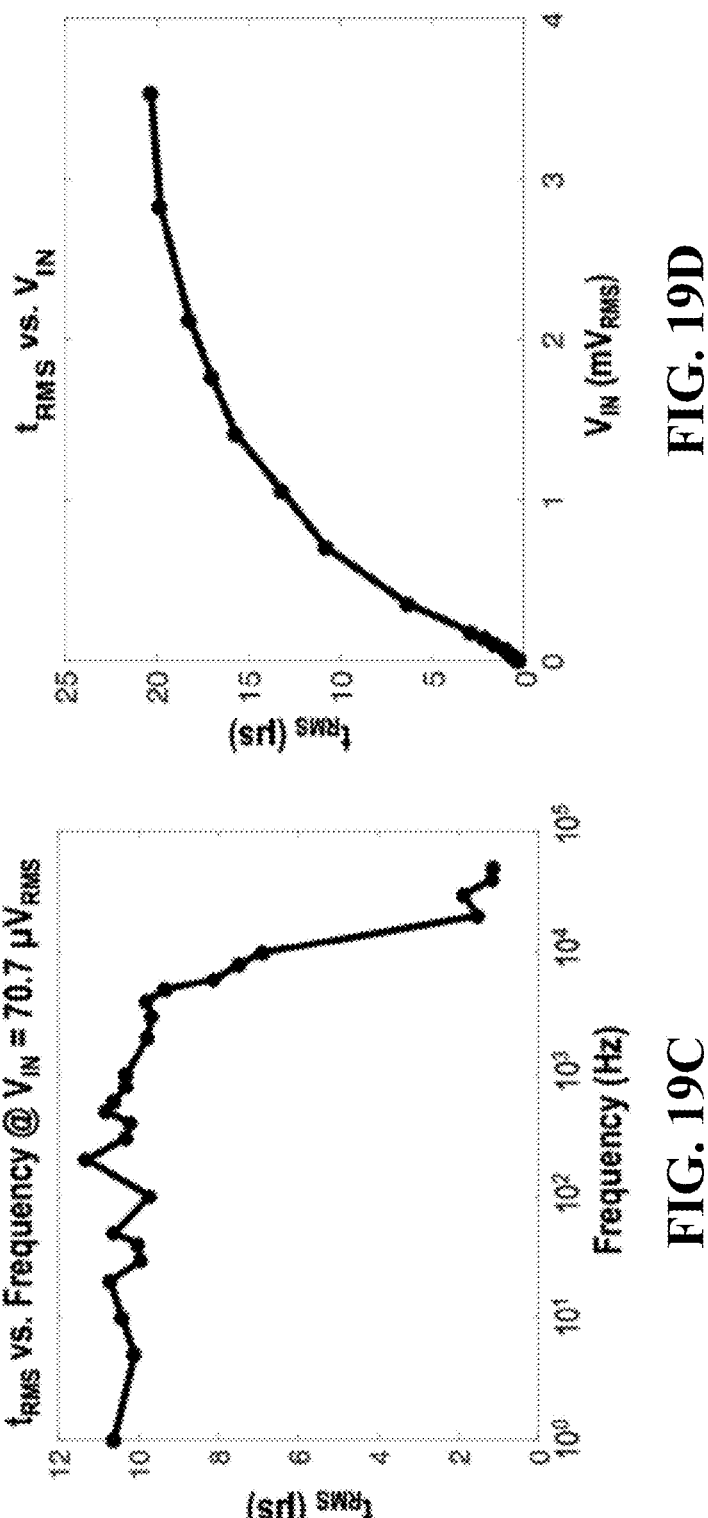
FIGS. 19C-19D show signal gain as a function of frequency (FIG. 19C) and amplitude (FIG. 19D).

FIGS. 19A-19B show example measurement of optical output pulse (FIG. 19A), and associated reconstructed 1 KHz waveform (FIG. 19B). FIGS. 19C-19D show signal gain as a function of frequency (FIG. 19C) and amplitude (FIG. 19D). The CMOS circuit is fabricated in 180 nm CMOS, with an active area of 210 μmx90 μm. For testing, the CMOS may be bonded to a PVLED. When illuminated with about 50 nW/μm2 of band-passed white light (380 nm-720 nm), which is about ⅛th of the safe limit for brain tissue, light pulses are measured as expected as shown in FIG. 19A. Driving the input electrodes with voltage signals modulates the timing of the pulses, from which the input is successfully reconstructed as shown here for a 1 KHz test signal. The system has a transduction gain of 140 ns/μ V across 1 Hz-10 KHz and the gain compresses for larger inputs>3 mVPP (1.1 VRMS) whereas the input referred noise floor of is about 21 μVRMS. The wake-up characteristics of the system for its potential use in pulse-powered environment (as opposed to continuous exposure as shown in FIG. 5A) may allow the system to wake up in under 1 ms.

FIG. 19A also shows an example of the device communicating near 20 kHz, but at a specific frequency that can be precisely measured to many decimal places, e.g. 19,857.12 Hz. This information provides the identity of the individual sensor. Small manufacturing differences between devices results in slightly different clock cycles. Hence an example device operating with a clock cycle of 19,857.12 Hz can be distinguished from a device with a 18,354.47 Hz clock cycle. This feature of the system imbues the device with a unique identity communicated optically and wirelessly.

Figure 28:
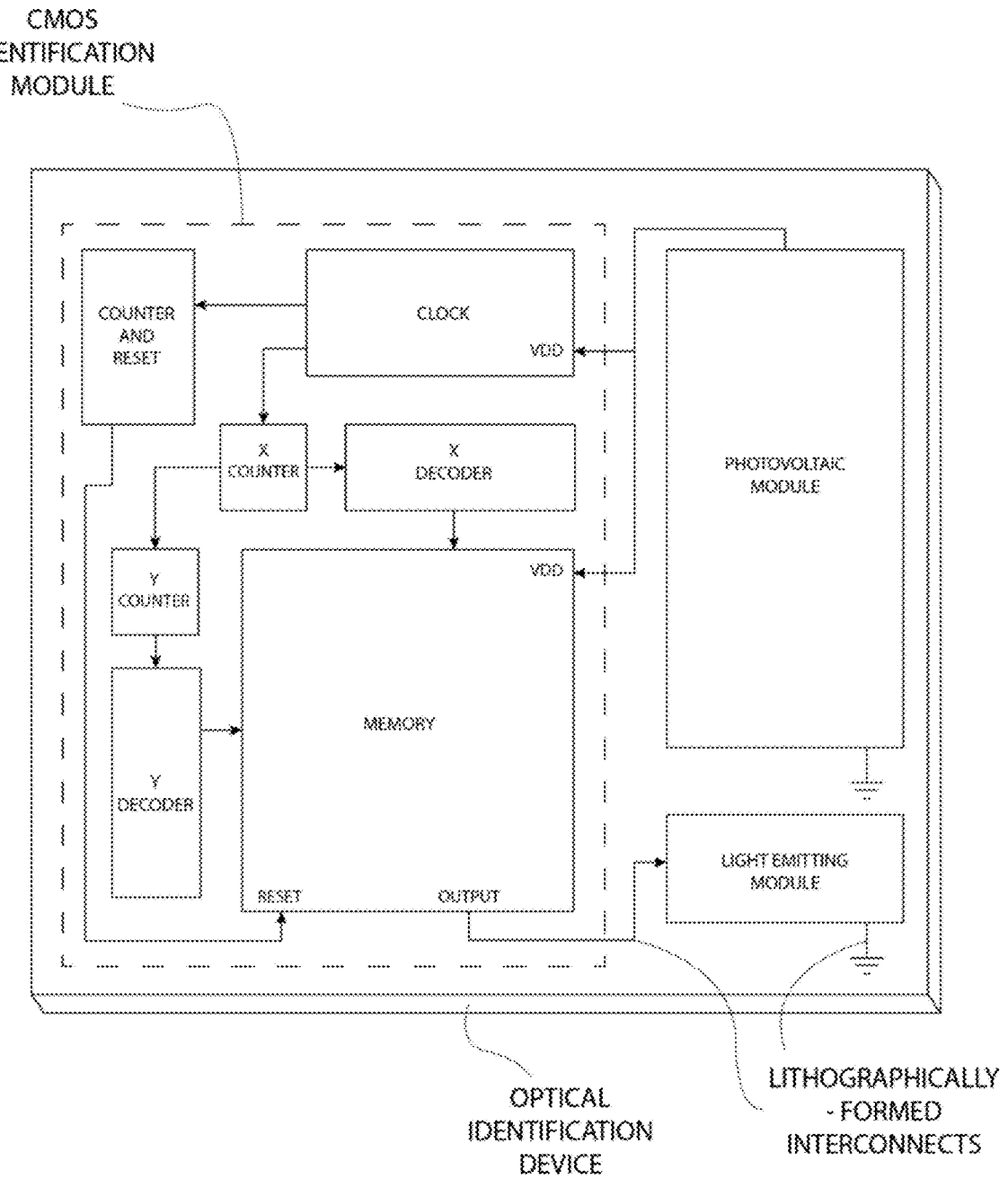
FIG. 28 shows an example layout and implementation of a wireless optical identification device based on the disclosed technology.

FIG. 28 shows one embodiment of a fully-integrated, stand-alone wireless optical device configured to generate a predetermined electrical identification signal indicative of an identity of the device. A photovoltaic module is configured to power the identification module with a supply voltage VDD. This power turns on a relaxation oscillator (e.g., a clock generator labeled CLOCK) which provides a periodic pulse to serve as the clock of the circuit. A set of counters, e.g. ring counter, labeled X COUNTER and Y COUNTER, provide an electric signal to a set of decoders, labeled X DECODER and Y DECODER, which are fed into a memory element (e.g., a memory labeled MEMORY). The output of the memory element is a sequence of voltages at either a low voltage, ground, or a high voltage VDD. The output of the memory element is configured to modulate the output light of the light emitting module, to carry the electrical identification signal to wirelessly and optically transmit the electrical identification signal out of the device. In one embodiment the timing of the output pulses of light from the light emitting module transmit the identity of the device. In another embodiment the sequence of light pulses from the light emitting module, labeled LIGHT EMITTING MODULE, transmits the identity of the device. The identification module is further configured to have a counter and reset (e.g., functional block labeled COUNTER AND RESET) which resets the memory of device, discharging any memory elements.

Figures 20A, 20B, 20C, 20D:
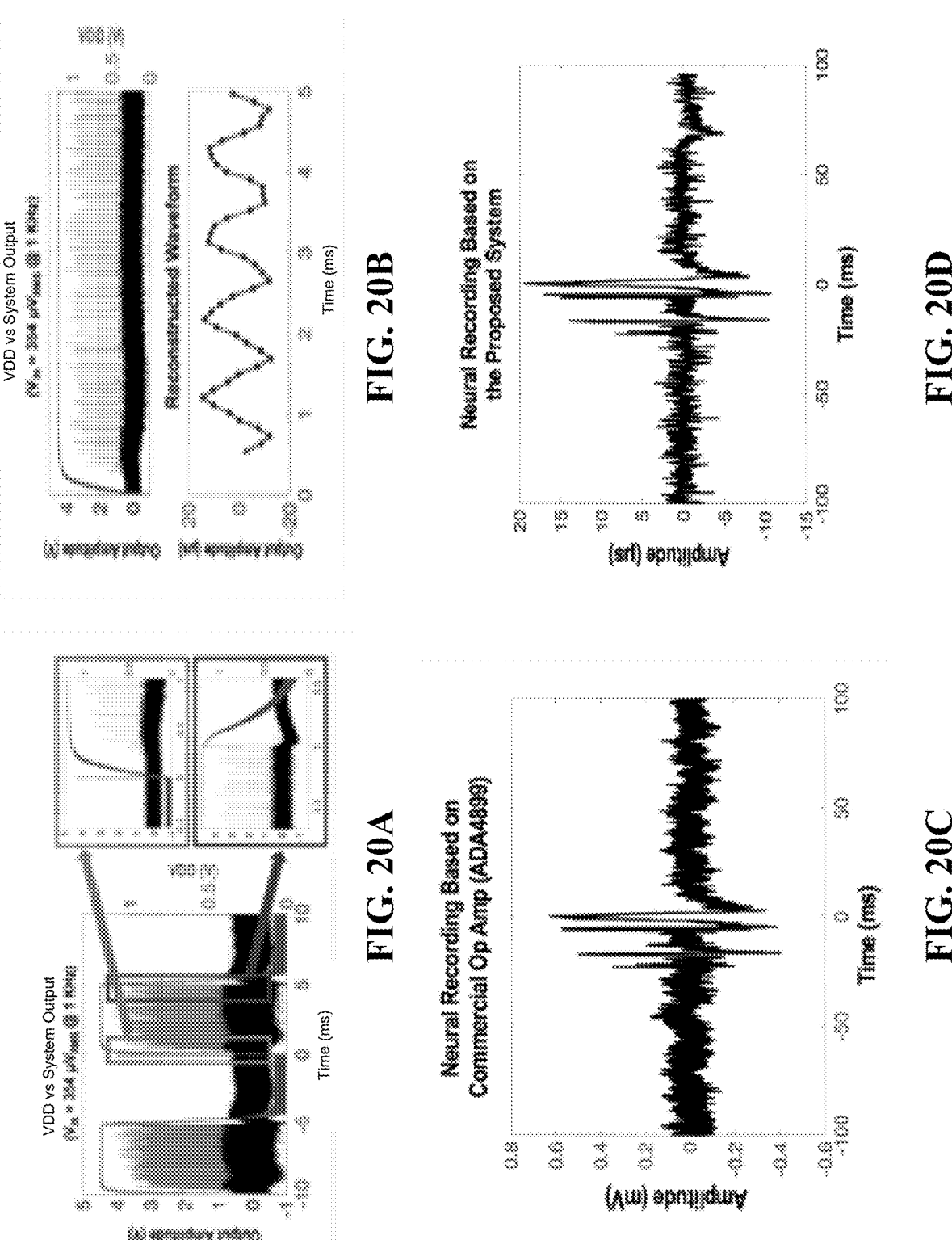
FIGS. 20A-20B show start-up, showing onset of optical pulses (FIG. 20A) and decoded signal (FIG. 20B).
FIGS. 20C-20D show neural recording on an earthworm ventral nerve upon mechanical stimulation measured in parallel through a commercial amplifier to provide baseline (FIG. 20C) and using the presented system, powered and communicating optically (FIG. 20D).

FIGS. 20A-20B show start-up, showing onset of optical pulses (FIG. 20A) and decoded signal (FIG. 20B). FIGS. 20C-20S show neural recording on an earthworm ventral nerve upon mechanical stimulation measured in parallel through a commercial amplifier to provide baseline (FIG. 20C) and using the presented system, powered and communicating optically (FIG. 20D). To demonstrate the system's capability to encode real neural signals, the input electrodes may be connected to the ventral nerve cord of an earthworm using probes, with a commercial neural amplifier connected in parallel to provide a reference baseline. FIGS. 20C-20S clearly show that the composite spikes have been accurately encoded in the output optical pulses, even when communication and power are purely optical.

Figure 21:
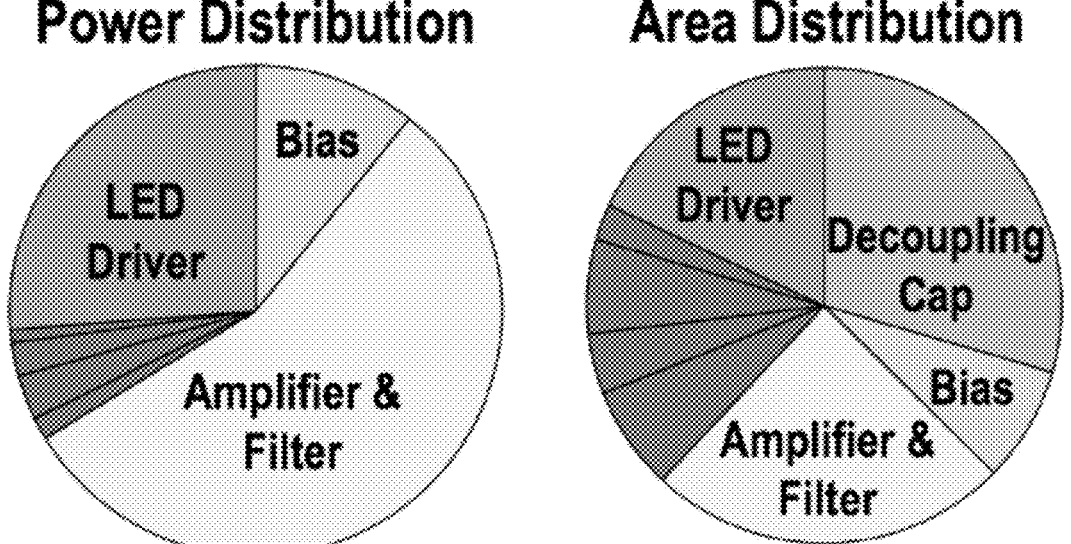
FIG. 21 shows a breakdown of the design by power consumption and by Si area.

FIG. 21 shows a breakdown of the design by power consumption (top-left) and by Si area (top-right). As emphasized earlier, the power consumption is dominated by the main amplifier and the charge pump. Area is dominated by the amplifier (for lower flicker noise), LED driver, and decoupling. The bottom of the FIG. 6 shows a table of comparison against prior art.

Figure 22:
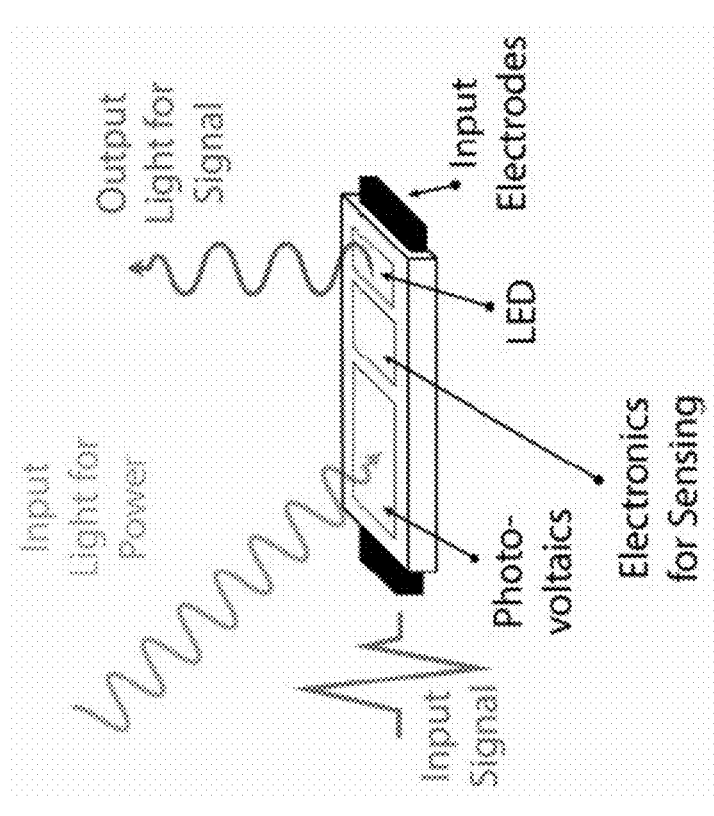
FIG. 22 shows an example of the optical wireless integrated circuit sensor implemented based on some embodiments of the disclosed technology.

FIG. 22 shows an example of the optical wireless integrated circuit sensor implemented based on some embodiments of the disclosed technology. As discussed above, such optical wireless integrated circuit sensors can be used for implantable medical diagnostics for neural activity, temperature monitoring for cancer cell growth or others. Various embodiments of the disclosed technology can be used to implement systems monitoring in micron-scale systems or materials, such as microfluidics, lab-on-a-chip, thermal properties of small samples materials.

Figure 23:
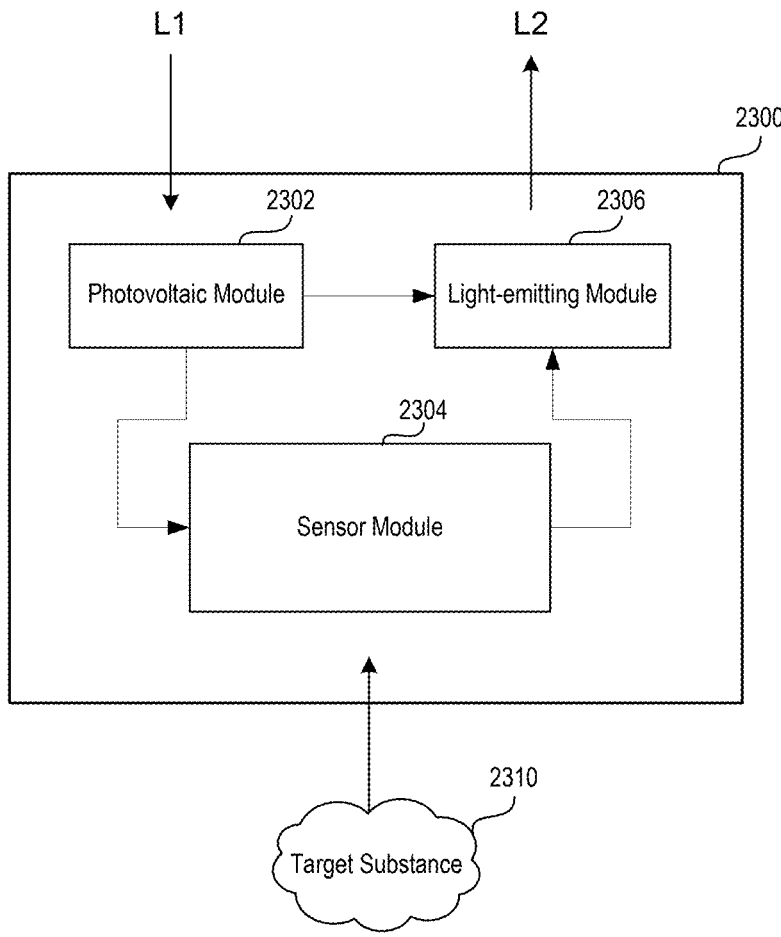
FIG. 23 shows an example of the optical wireless sensor device implemented based on some embodiments of the disclosed technology.

FIG. 23 shows an example of the optical wireless sensor device 2300 implemented based on some embodiments of the disclosed technology. The optical wireless sensor device 2300 may include a photovoltaic module 2302, a sensor module 2304, and a light-emitting module 2306. The photovoltaic module 2302 is structured to convert light L1 into electricity. The sensor module 2304 is coupled to photovoltaic module 2302 to receive power from the electricity generated by the photovoltaic module 2302. The sensor module 2304 is structured to include a sensing element that is responsive to a target substance 2310 to produce a response. The sensor module 2304 may also generate, based on the response from the sensing element, an electrical sensor signal indicative of a property of the target substance 2310. The light-emitting module 2306 is coupled to receive power from the electricity generated by the photovoltaic module 2302 and to receive the electrical sensor signal from the sensor module 2304. The light-emitting module 2306 may also produce output light L2 that is modulated to carry the electrical sensor signal to wirelessly and optically transmit the electrical sensor signal out of the device.

Figure 24:
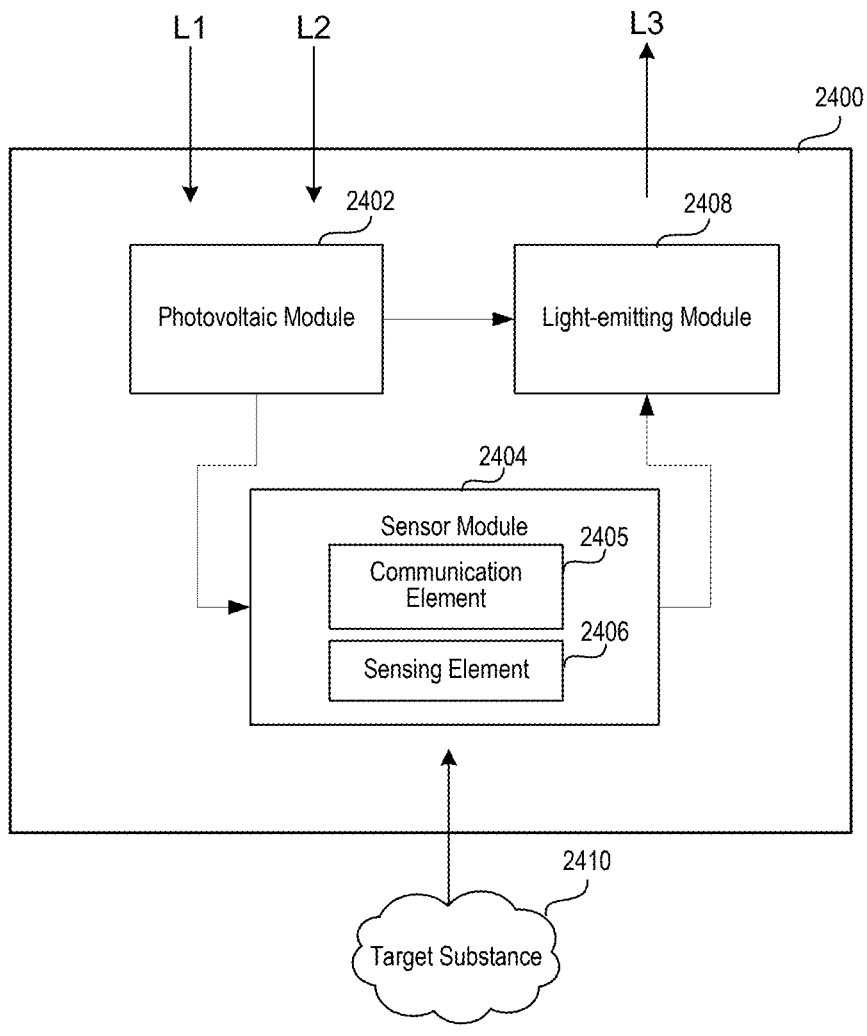
FIG. 24 shows an example of the optical wireless sensor device implemented based on some embodiments of the disclosed technology.

FIG. 24 shows an example of the optical wireless sensor device 2400 implemented based on some embodiments of the disclosed technology. The optical wireless sensor device 2400 includes a photovoltaic module 2402 structured to convert electromagnetic radiation L1 and L2 into electricity. The optical wireless integrated circuit sensor 2400 also includes a sensor module 2404 coupled to the photovoltaic to receive the electricity generated by the photovoltaic module. The sensor module 2404 includes a sensing element 2406 and a communication element 2405. The sensing element 2406 is responsive to a target substance 2410 to produce a response, and the communication element 2405 is structured to generate, based on the response from the sensing element 2406, an electrical sensor signal indicative of a property of the target substance 2410. The optical wireless sensor device 2400 also includes a light-emitting module 2408 coupled to the photovoltaic module 2402 to receive the electricity and coupled to the communication element 2305 of the sensor module 2404 to receive the electrical sensor signal and convert the electrical sensor signal to output electromagnetic radiation L3 indicative of the property of the target substance 2410. The electricity generated by the photovoltaic module is used to supply power to the sensor module 2404 and the light-emitting module 2408. In an embodiment of the disclosed technology, the electricity generated by the photovoltaic module may also be used to generate electrical control signals for controlling the sensor module 2404 and the light-emitting module 2408. In an embodiment of the disclosed technology, the radiation L1 is converted into power for operating the sensor module 2404 and the light-emitting module 2408, and the radiation L2 is converted into information associated with operations of the sensor module 2404 and/or the light-emitting module 2408 such as instructions for controlling the sensor module 2404 and/or the light-emitting module 2408. Here, the optical wavelength of the radiation L2 may be different from that of the radiation L1.

Figure 25:
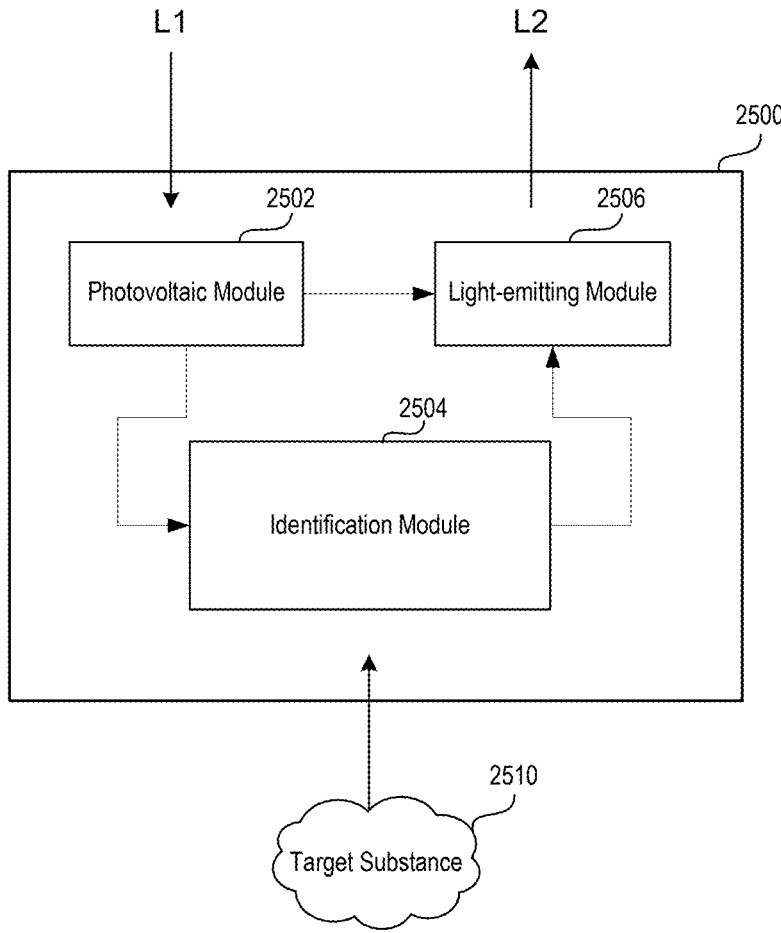
FIG. 25 shows an example of the optical wireless identification device implemented based on some embodiments of the disclosed technology.

FIG. 25 shows an example of the optical wireless identification device 2500 implemented based on some embodiments of the disclosed technology. The optical wireless identification device 2500 may include a photovoltaic module 2502, an identification module 2504, and a light-emitting module 2506. The photovoltaic module 2502 is structured to convert light L1 into electricity. The identification module 2504 is coupled to photovoltaic module 2502 to receive power from the electricity generated by the photovoltaic module 2502. The identification module 2504 configured to generate an electrical identification signal indicative of an identity of the device. The light-emitting module 2506 may also produce output light L2 that is modulated to carry the electrical identification signal to wirelessly and optically transmit the electrical identification signal out of the device.

Figure 26:
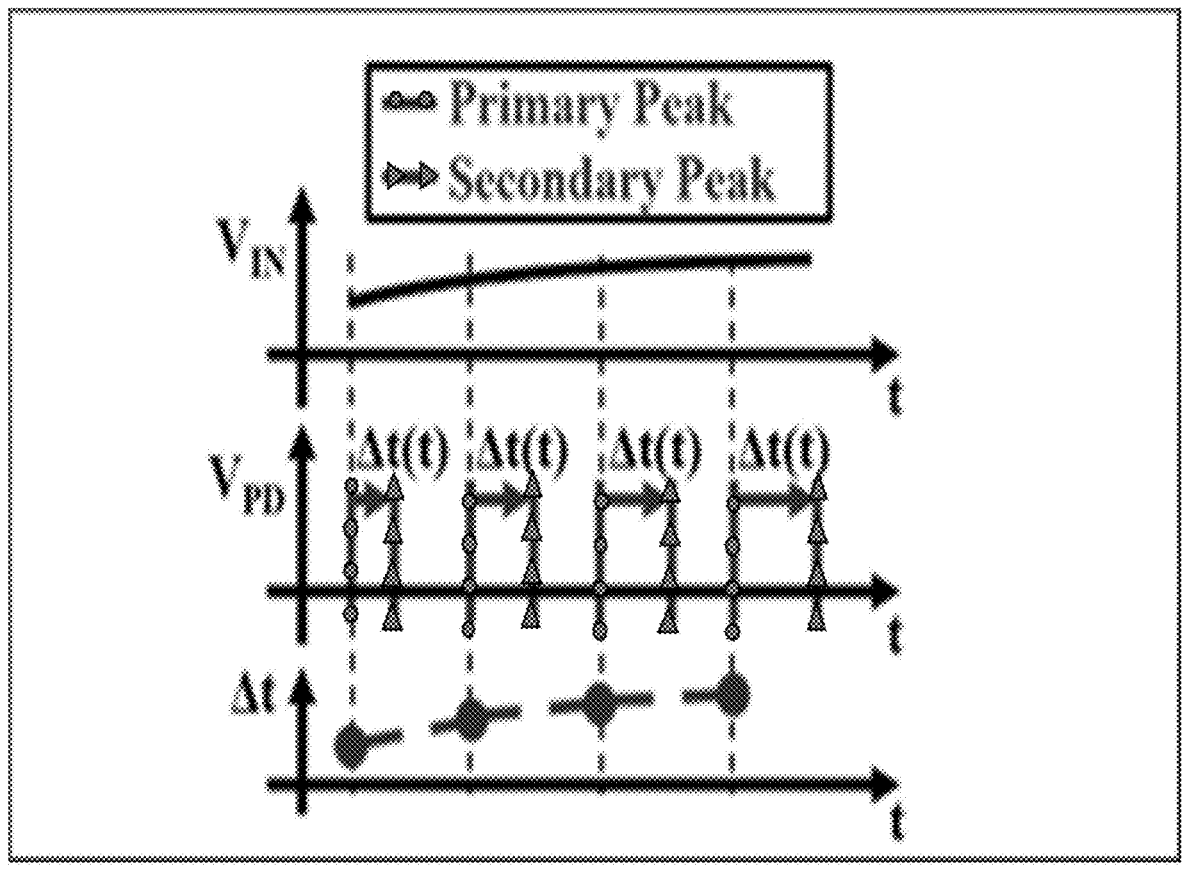
FIG. 26 shows an example of pulsed-position modulation (PPM) encoding

FIG. 26 shows an example of pulsed-position modulation (PPM) encoding where VPD and Δt denotes photodetector output and pulse spacing (between the primary and secondary), respectively. In some embodiments of the disclosed technology, the output light can be modulated using a pulsed-position modulation scheme. For example, the signal measured from the sensor module or the identification module is encoded in the timing between pulses as shown in FIG. 26. One set of pulses, "primary peak." occurs at some regular frequency. Another set of pulses (every other pulse), "secondary peak," encodes the input signal. In this implementation, the time between pulses encodes the voltage. In this way, the output light can be modulated to carry the electrical sensor signal or the electrical identification signal to wirelessly and optically transmit the electrical sensor signal out of the device.

FIG. 27 shows an example method for sensing a target subject. The method includes, at 2702, implanting a sensor on a target subject without having a physical connection to the sensor, at 2704, directing illumination light onto the sensor implanted on the target subject to cause a photovoltaic module in the sensor to generate electric power for operating the sensor so that the generated electric power powers (1) a sensor module which performs a sensing operation on the target subject to generate an electrical sensor signal indicative of a property of the target subject, and (2) a light-emitting module coupled to receive the electrical sensor signal from the sensor module and operable to produce output light that is modulated to carry the electrical sensor signal, and, at 2706, receiving information indicative of the property of the target subject by using the output light to wirelessly and optically transmit the electrical sensor signal out of the device.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

We claim:

1. A device with opto-electronic circuitry, comprising:
a substrate;
a photovoltaic module on the substrate and structured to convert incident light into electricity;
an identification module on the substrate and coupled to receive power from the electricity generated by the photovoltaic module and to generate an electrical identification signal indicative of a unique identity of the device that uniquely identifies the device from other devices;
a light-emitting module on the substrate and coupled to receive power from the electricity generated by the photovoltaic module and to receive the electrical identification signal from the identification module and operable to produce output light that is modulated to carry the electrical identification signal to wirelessly and optically transmit the electrical identification signal out of the device; and
electrical interconnects lithographically formed on the substrate and configured to electrically connect the light-emitting module, the photovoltaic module and the identification module, the electrical interconnects structured to have a dimension at or below 40 microns and a pitch below 40 microns between two adjacent electrical interconnects.

2. The device as in claim 1, wherein:
the dimension of the electrical interconnects is at or below 30 microns, 20 microns, 15 microns, or 10 microns; and
the pitch between two adjacent electrical interconnects is at or below 30 microns, 20 microns, or 10 microns.

3. The device as in claim 1, wherein:
the light-emitting module includes a plurality of semiconductor layers that are initially formed on a separate substrate, are transferred onto the substrate and are bonded to the substrate, and the light-emitting module.

4. The device as in claim 3, wherein each of the plurality of semiconductor layers of the light emitting module has a layer thickness in a range from under nanometers to several hundred nanometers.

5. The device as in claim 3, wherein the semiconductor layers include III-V semiconductor materials.

6. The device as in claim 5, wherein the substrate includes silicon.

7. The device as in claim 1, wherein the photovoltaic module includes a plurality of photovoltaic circuits electrically connected in series by lithographically formed electrical interconnects to provide an output voltage larger than an output voltage of each of photovoltaic circuits.

8. The device as in claim 1, wherein the identification module includes decoders to perform decoding in generating the electrical identification signal.

9. The device as in claim 1, wherein the identification module is configured to generate the electrical identification signal indicative of the entity of the device to enable use of signal multiplexing in time for monitoring a large number of different devices by uniquely identifying each device.

10. The device as in claim 1, wherein the identification module includes:
a clock circuit to generate a clock signal;
a counter circuit coupled to the clock circuit;
a decoder coupled to the counter circuit; and
a memory device coupled to the decoder circuit and further coupled to the light-emitting module, wherein the memory device is operable to output the electrical identification signal to the light-emitting module to cause the light-emitting module to produce that output light that is modulated to carry the electrical identification signal to wirelessly and optically transmit the electrical identification signal out of the device.

11. The device as in claim 10, wherein the identification module includes a counter and reset circuit coupled to the clock circuit and the memory device and operable to reset the memory device.

12. The device as in claim 1, wherein the light-emitting module is configured so that the produced output light is modulated to carry the electrical identification signal by timing information of output light pulses of the produced output light.

13. The device as in claim 1, wherein the light-emitting module is configured so that the produced output light is modulated to carry the electrical identification signal by a sequence of output light pulses of the produced output light.

14. The device as in claim 1, comprising a sensor module on the substrate and additional electrical interconnects lithographically formed on the substrate to electrically connect the sensor, the light-emitting module, and the photovoltaic module, wherein the additional electrical interconnects are structured to have a dimension at or below 40 microns and a pitch below 40 microns between two adjacent electrical interconnects, and the sensor module is coupled to receive power from the electricity generated by the photovoltaic module, the sensor module structured to include a sensing element that is responsive to a target substance to produce a response and to generate, based on the response from the sensing element, an electrical sensor signal indicative of a property of the target substance.

15. The device as in claim 14, wherein the light-emitting module is configured to receive the electrical sensor signal from the sensor module, in addition to receiving the electrical identification signal from the identification module, and is operable to produce the output light that is modulated to carry both the electrical sensor signal and the electrical identification signal to wirelessly and optically transmit the electrical sensor signal and the electrical identification signal out of the device.

16. The device as in claim 14, wherein the sensor module is structured to generate the electrical sensor signal indicative of a temperature of the target substance, a presence of a biological or chemical substance in the target substance, or an electrical property of the target substance.

17. A device with opto-electronic circuitry, comprising:
a substrate;
a photovoltaic module on the substrate and structured to convert input light into electricity;
a sensor module on the substrate and coupled to receive power from the electricity generated by the photovoltaic module, the sensor module structured to include a sensing element that is responsive to a target substance to produce a response, wherein the sensor module is further configured to generate, based on the response from the sensing element, an electrical sensor signal indicative of a property of the target substance;
a light-emitting module on the substrate and coupled to receive power from the electricity generated by the photovoltaic module and to receive the electrical sensor signal from the sensor module, the light-emitting module structured to produce output light that is modulated to carry the electrical sensor signal to wirelessly and optically transmit the electrical sensor signal out of the device; and
electrical interconnects lithographically formed on the substrate and configured to electrically connect the light-emitting module, the photovoltaic module and the sensor module, wherein the electrical interconnects are structured to have a dimension at or below 40 microns and a pitch below 40 microns between two adjacent electrical interconnects.

* * * * *